(12) United States Patent
Yuan

(10) Patent No.: US 10,346,973 B2
(45) Date of Patent: Jul. 9, 2019

(54) SCORING OF TUMOR INFILTRATION BY LYMPHOCYTES

(71) Applicant: THE INSTITUTE OF CANCER RESEARCH: ROYAL CANCER HOSPITAL, London (GB)

(72) Inventor: Yinyin Yuan, London (GB)

(73) Assignee: THE INSTITUTE OF CANCER RESEARCH: ROYAL CANCER HOS, London (GB)

( * ) Notice: Subject to any disclaimer, the term of this patent is extended or adjusted under 35 U.S.C. 154(b) by 24 days.

(21) Appl. No.: 15/527,284

(22) PCT Filed: Nov. 24, 2015

(86) PCT No.: PCT/GB2015/053571
§ 371 (c)(1),
(2) Date: May 16, 2017

(87) PCT Pub. No.: WO2016/083791
PCT Pub. Date: Jun. 2, 2016

(65) Prior Publication Data
US 2017/0365053 A1     Dec. 21, 2017

(30) Foreign Application Priority Data

Nov. 24, 2014 (GB) .................................. 1420859.9

(51) Int. Cl.
*G06T 7/00* (2017.01)
*G01N 33/574* (2006.01)

(52) U.S. Cl.
CPC ..... *G06T 7/0012* (2013.01); *G01N 33/57415* (2013.01); *G01N 2800/52* (2013.01);
(Continued)

(58) Field of Classification Search
CPC ......... G06T 7/0012; G06T 2207/30096; G06T 2207/30068; G01N 33/57415; G01N 2800/52
See application file for complete search history.

(56) References Cited

U.S. PATENT DOCUMENTS

| 7,042,639 B1 * | 5/2006 | McDowell ......... G02B 21/0004 359/368 |
| 2006/0036372 A1 * | 2/2006 | Yener .................. G06K 9/0014 702/19 |

(Continued)

FOREIGN PATENT DOCUMENTS

WO        2013154422       10/2013

OTHER PUBLICATIONS

Adams et al, (2014) "Prognostic Value of Tumor-Infiltrating Lymphocytes in Triple-Negative Breast Cancers From Two Phase III Randomized Adjuvant Breast Cancer Trials: ECOG 2197 and ECOG 1199", Journal of Clinical Oncology, vol. 32, No. 27, pp. 2959-2966.

(Continued)

*Primary Examiner* — Brenda C Bernardi
(74) *Attorney, Agent, or Firm* — Shweta Chandra; Bozicevic, Field & Francis LLP

(57) ABSTRACT

A method of providing a prognosis in a cancer patient comprising analyzing a tumor image to calculate a metric of immune infiltration for the tumor, and a method of analyzing a tumor image.

8 Claims, 28 Drawing Sheets

(52) U.S. Cl.
CPC .............. *G06T 2207/30068* (2013.01); *G06T 2207/30096* (2013.01)

(56) References Cited

U.S. PATENT DOCUMENTS

| | | | | |
|---|---|---|---|---|
| 2008/0026986 | A1* | 1/2008 | Wang | A61K 31/7042 514/1.1 |
| 2014/0003702 | A1 | 1/2014 | McCulloch et al. | |
| 2015/0290207 | A1* | 10/2015 | Kutok | A61K 31/495 424/134.1 |
| 2017/0139545 | A1* | 5/2017 | Tsurumi | G06T 7/73 |
| 2017/0334999 | A1* | 11/2017 | Sathyanarayanan | C07K 16/3023 |

OTHER PUBLICATIONS

Basavanhally et al, (2017) "Computerized image-based detection and grading of lymphocytic infiltration in HER2+ breast cancer histopathology", IEEE Transactionson on Biomedical Engineering, Vol. 57, No. 3,pp. 642-653.

Denkert et al, (2010) "Tumor-associated lymphocytes as an independent predictor of response to neoadjuvant chemotherapy in breast cancer", J. Clinical Oncology, vol. 28, pp. 105-113.

Feichtenbeiner et al, (2014) "Critical role of spatial interaction between CD8+ and Foxp3+ cells in human gastric cancer: the distance matters", Cancer Immunology, Immunotherapy, vol. 63 issue 2, pp. 111-119.

Galon et al, (2013) "Towards the introduction of the 'Immunoscore' in the classification of malignant tumours", Journal of Pathology, 232:199-209.

Galon et al, (2006) "Type, density, and location of immune cells within human colorectal tumors predict clinical outcome." Science 313(5795): 1960-1964.

Heindl et al, (2015) "Mapping spatial heterogeneity in the tumor microenvironment: a new era for digital pathology", Laboratory Investigation, vol. 95, No. 4, pp. 377-384.

Ibrahim et al, (2014) "The prognostic value of tumor-infiltrating lymphocytes in triple-negative breast cancer: a meta-analysis", Breast Cancer Research and Treatment, vol. 148,3, pp. 467-476.

Issa-Nummer et al, (2013) "Prospective Validation of Immunological Infiltrate for Prediction of Response to Neoadjuvant Chemotherapy in HER2-Negative Breast Cancer—A Substudy of the Neoadjuvant GeparQuinto Trial", PLOS ONE, vol. 8,12, pp. 1-7.

Janowczyk et al, (2013) "Quantifying local heterogeneity via morphologic scale: Distinguishing tumoral from stromal regions", J Pathol Inform, vol. 1, 8, p. 1-10.

Kruger et al, (2013) "Combat or surveillance? Evaluation of the heterogeneous inflammatory breast cancer microenvironment", The Journal of Pathology, vol. 229, No. 4, pp. 569-578.

Mulligan et al, (2012) "Tumoral Lymphocytic Infiltration and Expression of the Chemokine CXCL10 in Breast Cancers from the Ontario Familial Breast Cancer Registry" Clinical Cancer Research, vol. 19, No. 2, pp. 336-346.

Robert et al, (2011) "Ipilimumab plus Dacarbazine for Previously Untreated Metastatic Melanoma", The New England Journal of Medicine, pp. 1-10.

Salgardo et al, (2014) "Harmonization of the evaluation of tumour infiltration lymphocytes (TILs) in breast cancer: recommendations by an international TILs-Working" Annals of Oncology.

Yuan et al, (2012) "Quantitative Image Analysis of Cellular Heterogeneity in Breast Tumors Complements Genomic Profiling", Sci Transl Med, 4; pp. 1-10.

Yuan, (2014) "Modelling the spatial heterogeneity and molecular correlates of lymphocytic infiltration in triple-negative breast cancer". Nature, vol. 7, No. 7418, pp. 93-20141153.

* cited by examiner

SCORING OF TUMOR INFILTRATION BY LYMPHOCYTES

FIELD OF THE INVENTION

The present invention relates to tumour analysis, and to cancer prognosis. In particular, the present invention relates to methods of analysing tumours for determining a prognosis in cancer.

BACKGROUND

Cancer is a complex and dynamic disease, and many different ways of analysing and classifying tumours have been developed with the aims of determining the degree of tumour progression or invasiveness and the prognosis for the patient, and informing treatment decisions.

Methods of analysing tumours include the assessment of cell morphology in tumours (typically performed by pathologists), measurement of gene expression in tumours (e.g. by microarray analysis), determination of gene mutation status in tumour cells, and evaluating protein expression within tumours (e.g. by immunohistochemical assessment of tumour sections). These methods of analysing tumours are important not only for predicting clinical outcome, but also for informing decisions on patient therapy.

More recently, it has become apparent that the immunological status of tumours can yield useful prognostic information. Accumulating evidence supports the clinical significance of immune response in many cancer types (Galon et al. 2006, Denkert et al. 2010, Loi et al.). Consistent studies have reported associations between immune activity and disease outcome as well as treatment response (Galon et al. 2006, Denkert et al. 2010, Loi et al., Liu et al., Lee et al., DeNardo et al.).

Furthermore, increasing evidence from clinical trials supports the potential of therapies that target immune activity in certain types of cancer (Robert et al., Stagg et al.). This is perhaps best exemplified in late stage melanoma where recent clinical trials have shown an increased survival advantage in patients receiving the monoclonal antibody ipilimumab, which targets the CTLA4 protein receptor that is expressed on the surface of T cells (Robert et al.). This has led to the development of more standardised methods of characterising tumour immune infiltrate in cancers such as the "immunescore" that aims to quantify the in situ immune infiltrate in addition to standardised clinical parameters to aid prognostication and patient selection for immunotherapy in colorectal cancers (Galon et al. 2014).

However, to facilitate the standardisation and reproducibility of scoring immune infiltration, objective approaches are urgently needed (Galon et al. 2014). Furthermore, such approaches need to account for the complexity of immune infiltration into tumours. Abundance, spatial heterogeneity and type of immune cells are the key parameters of immune infiltration (Galon et al. 2014, Fridman et al.). For example, the spatial locations of immune cells have been shown to be useful in predicting the prognosis of colorectal cancer (Galon et al. 2006). Indeed the pathological "immunescore" is based on the numeration of two lymphocyte populations (CD8+ and CD45RO+ cells), both in the core of the tumour and in the invasive margin that maximises the prognostic power (Galon et al. 2014).

Similarly, large-scale studies of breast cancer have demonstrated that pathological assessment of tumour-infiltration lymphocytes based on Hematoxylin & Eosin (H&E) stained core biopsies is a significant predictor for response to neoadjuvant chemotherapy in 1,058 breast cancer samples (Denkert et al. 2010). Recently, a prospective study demonstrated that in HER2-negative breast cancer stromal lymphocytes can be an independent predictor of response to neoadjuvant chemotherapy (Issa-Nummer et al.). Thus, the spatial organisation of lymphocytic infiltration in the context of nearby cancer cells is an important clinicopathological feature of tumours.

In triple-negative breast cancer (TNBC) an active immune response has been associated with favourable prognosis (Loi et al., Liu et al., Denkert et al.). A large-scale immunohistochemistry study of 3,400 breast cancer samples has showed that TNBC is the only subtype of breast cancer to demonstrate a significant link between CD8-positive immune cells and a good prognosis (Liu et al.). Assessment of lymphocytic infiltration based on whole-tumour H&E sections has been associated with favourable outcome in 256 patients after anthracycline-based chemotherapy (Loi et al.). A recent prospective study showed that the presence of tumour-infiltrating lymphocytes in residual tumours after neoadjuvant chemotherapy is predictive of good prognosis in TNBC (Dieci et al.). Given the current lack of targeted molecular treatment and poor clinical outcome of TNBC, this may suggest new therapeutic opportunities for this aggressive tumour type (Stagg et al.). For instance, accumulating data suggest that anthracyclines mediate their action through activation of CD8+ T-cell responses, hence combination with certain immunotherapies could be especially effective for TNBC (Stagg et al.).

However, despite these advances in understanding of the importance of immune infiltration in cancer, there is a lack of reproducible approaches to objectively assess immune infiltration based on pathological sections.

SUMMARY OF THE INVENTION

Lymphocytic infiltration in tumours is often associated with a favourable prognosis and predicts response to chemotherapy in many cancer types. However, it is not well understood because the high levels of spatial and molecular heterogeneity within tumours make it difficult to analyse by traditional pathological assessment.

Identification of cell types by pathologists in the assessment of immune infiltration provides qualitative information on coarse ordinal scales. Such information is poorly suited to analysing large data collections, partly because the high amount human input required renders large scale studies time-consuming and expensive, partly because the subjective nature of the assessment causes an unacceptable degree of variability in the information, and partly because the qualitative data generated do not lend themselves to statistical analysis.

The inventor has devised a robust and reproducible method for objectively assessing immune infiltration in tumours. The method is performed on a tumour image in which lymphocytes and cancer cells have been identified.

The method may be performed on images of hematoxylin & eosin (H&E) stained tumour sections. H&E stained sections, and images of H&E stained sections, are often readily available as part of data sets collected for cancer study groups such as the METABRIC group (Curtis, 2012) and the Cancer Genome Atlas (TCGA) group (TCGA, 2012), which makes the methods of the present invention readily adaptable for use in analysing tumours from a variety of cancer types. The method may comprise a step of treating a tumour section with a stain, such as H&E, wherein the presence of subcellular structures such as nuclei creates complexes between the stain and the subcellular structure.

An aspect of the present invention provides a method of measuring immune infiltration in a tumour. In particular, there is provided a method of determining an objective measurement of immune infiltration in a tumour, referred to herein as the ITLR. The ITLR (Intra-Tumour Lymphocyte Ratio) is the ratio of intra-tumour lymphocytes to cancer cells in the tumour expressed as a decimal fraction. For example a ratio of 11 intra-tumour lymphocytes to 1000 cancer cells corresponds to an ITLR of 0.011.

Accordingly, an aspect of the invention provides a method of measuring immune infiltration in a tumour, the method comprising:
   providing an image of the tumour in which lymphocytes and cancer cells have been identified;
   obtaining a lymphocyte-to-cancer measurement for each lymphocyte;
   classifying a subset of the lymphocytes as intra-tumour lymphocytes according to their lymphocyte-to-cancer ratio;
   quantifying the intra-tumour lymphocytes and the cancer cells in the tumour image;
   calculating the intra-tumour lymphocyte ratio (ITLR) as the ratio of intra-tumour lymphocytes to cancer cells, wherein the ITLR is a measurement of immune infiltration in the tumour.

A further aspect of the present invention provides a method of determining a cut-off value for ITLR for use in determining a prognosis in cancer, wherein an ITLR below the cut-off value indicates a poor prognosis. The method comprises determining the ITLR for a plurality of tumours, wherein each tumour is from a respective cancer patient in a cohort of cancer patients, and selecting a cut-off value for the ITLR wherein patients with an ITLR lower than the cut-off value have a worse prognosis compared with patients with an ITLR equal to or higher than the cut-off value.

Accordingly, an aspect of the invention provides a method of determining an ITLR cut-off value for a cancer type or subtype, for use in providing a prognosis in a cancer patient having that cancer type, the method comprising:
   measuring immune infiltration in a tumour from each member of a cohort of cancer patients having the cancer type or subtype according to the methods described herein, thereby calculating the ITLR for each tumour;
   relating the ITLR for each tumour to the clinical outcome of each cancer patient in the cohort of cancer patients; and
   selecting a cut-off value for ITLR, wherein an ITLR equal to or below the cut-off value is associated with a significantly worse clinical outcome in the cohort of cancer patients than an ITLR above the cut-off value A further aspect of the present invention provides a method of providing a prognosis in cancer. In particular, there is provided a method of using ITLR as a prognostic biomarker for a cancer patient. The method may comprise measuring the ITLR of a tumour from a cancer patient and using the ITLR to determine a prognosis for the patient. The method may comprise determining the ITLR in a tumour from a cancer patient and using the ITLR to determine a prognosis for the patient, wherein an ITLR below a predetermined cut-off value indicates a poor prognosis.

Accordingly, an aspect of the invention provides a method of providing a prognosis in a cancer patient, the method comprising:
   measuring immune infiltration in a tumour from the cancer patient according to the methods described herein, thereby calculating the ITLR for the tumour, wherein an ITLR below a predetermined ITLR cut-off value indicates a poor prognosis.

The present invention further provides a method of treating cancer in a patient, the method comprising determining the ITLR in a tumour from the patient or requesting a test providing the results of an analysis to determine the ITLR in a tumour from the patient, and treating the patient according to a therapeutic regime depending on whether the ITLR is equal to or below, or above, a predetermined-cut-off value.

A. 3D landscapes illustrating the spatial heterogeneity of cancer cells and lymphocytes in an H&E breast whole-tumour section. The height of the hills in the 3D landscape represents the density of cells. B. Combined analysis of the spatial distribution of cancer and lymphocytes can lead to quantification of lymphocytic infiltration. Shown are a small H&E image and the corresponding 3D cancer density map, which facilitate the measurement of spatial proximity to cancer for every single lymphocyte in the image.

Figure 2:
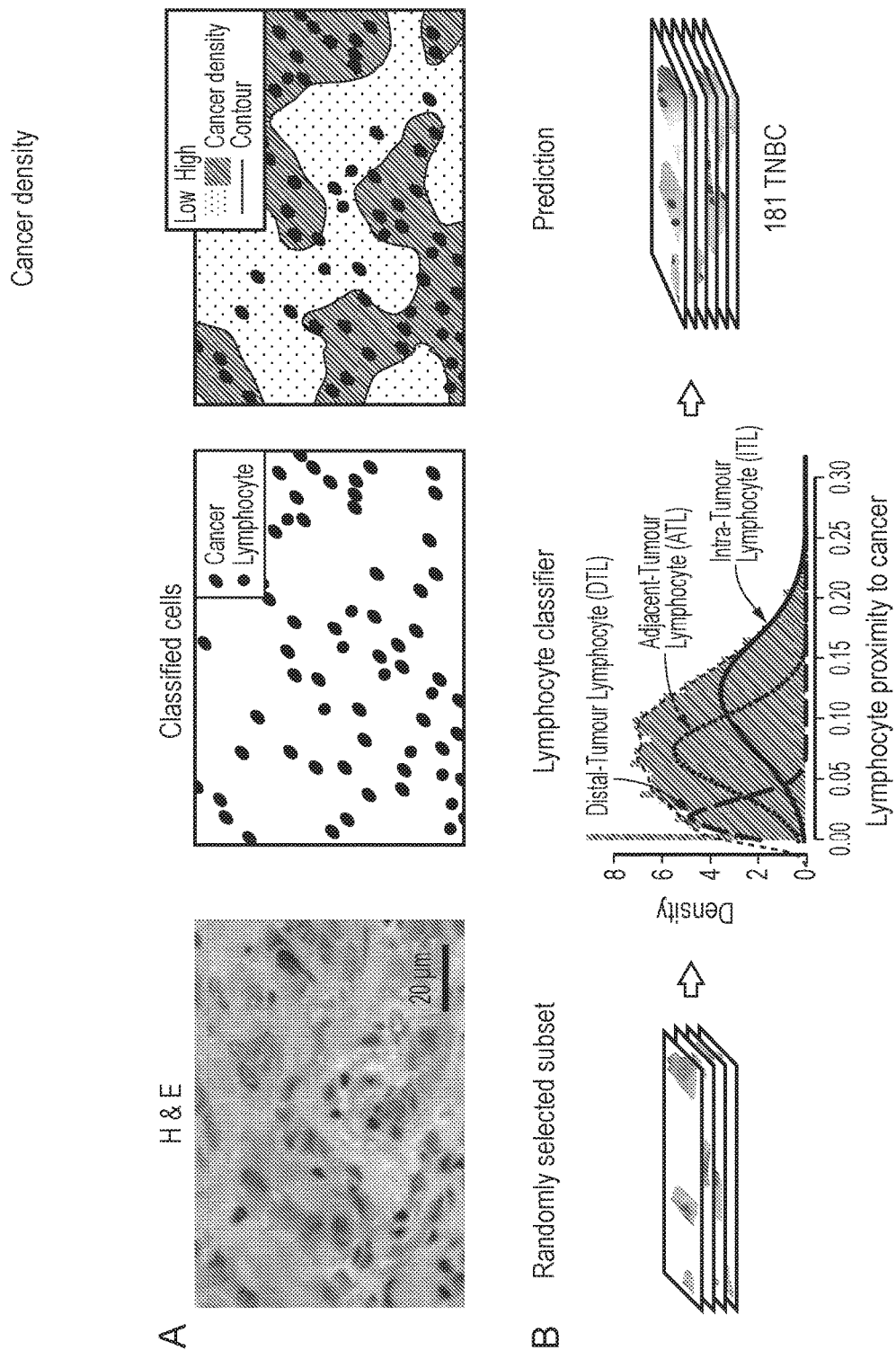
Figure 2:
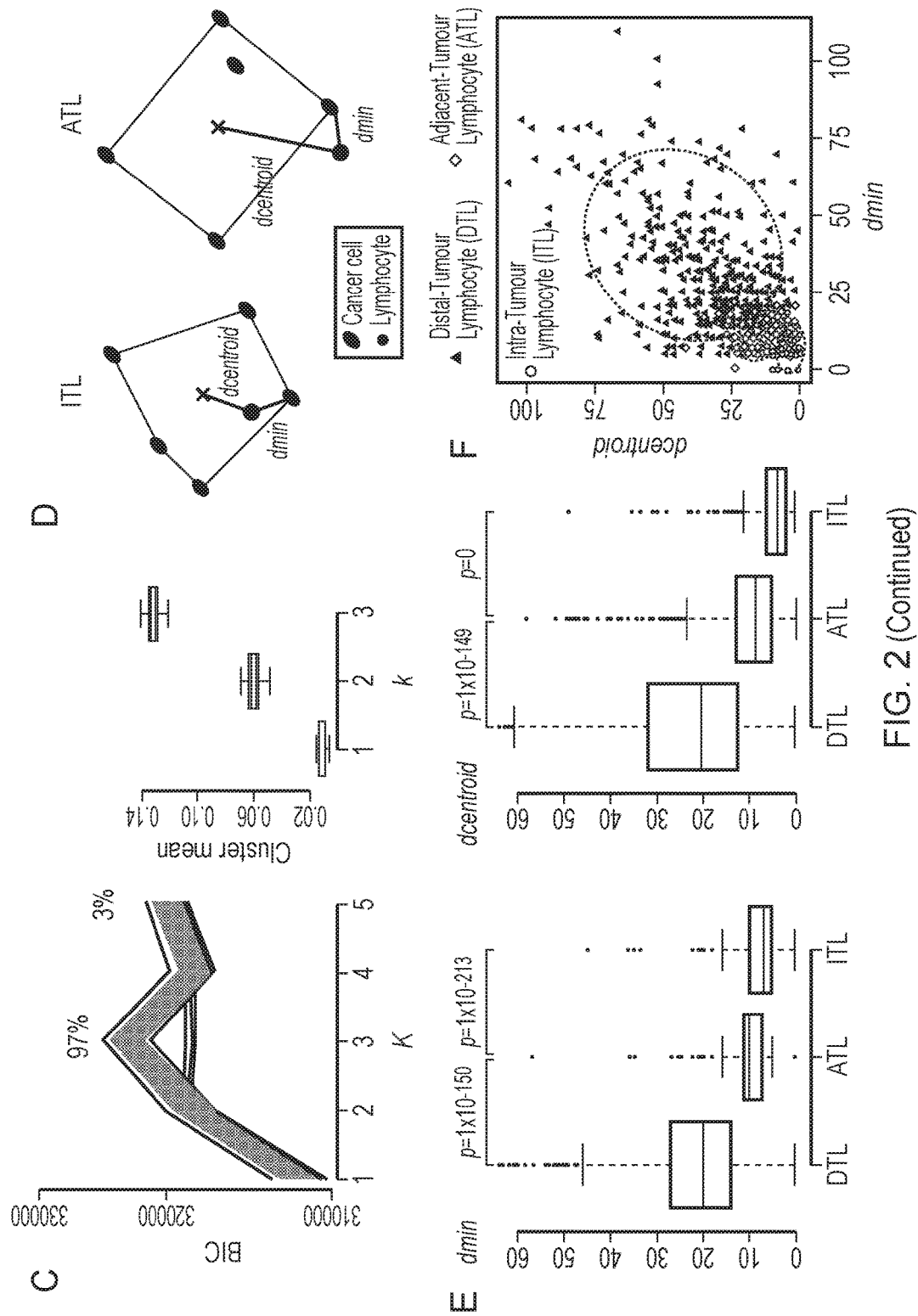

FIG. 2. Quantifying the intra-tumour heterogeneity of lymphocytic infiltration.

A. Schematic depiction of the computational pipeline exemplified with a small region of a breast cancer H&E section: H&E image; classified cells using automated image analysis; a map of cancer density based on image analysis result to quantify cancer-immune spatial relationships. B. Discovery of three categories of lymphocytes with unsupervised clustering based on the spatial proximities of lymphocytes to cancer in a subset of TNBC samples. These data were then used to predict the categories of all lymphocytes in all TNBC samples. C. Optimal number of cluster K as suggested by BIC over 200 random sampling are 3 in 97% of the time and 5 (3%). BIC curves for the 200 sampling are showed on the left, and boxplot showing means of clusters for K=3 solutions in 200 sampling on the right. D. Illustration of the distance to the nearest cancer cell $d_{min}$ and the distance to the centroid of convex hull region formed by 10 nearby cancer cells $d_{centroid}$ E. Boxplots to show the differences among lymphocyte classes in terms of $d_{min}$ and $d_{centroid}$ (p-values by t-test). F. Scatter plot showing $d_{min}$ and $d_{centroid}$ for 1,000 randomly selected lymphocytes, coloured based on the three classes; dashed ellipses showing three clusters fitted to $d_{min}$ and $d_{centroid}$.

Figure 3:
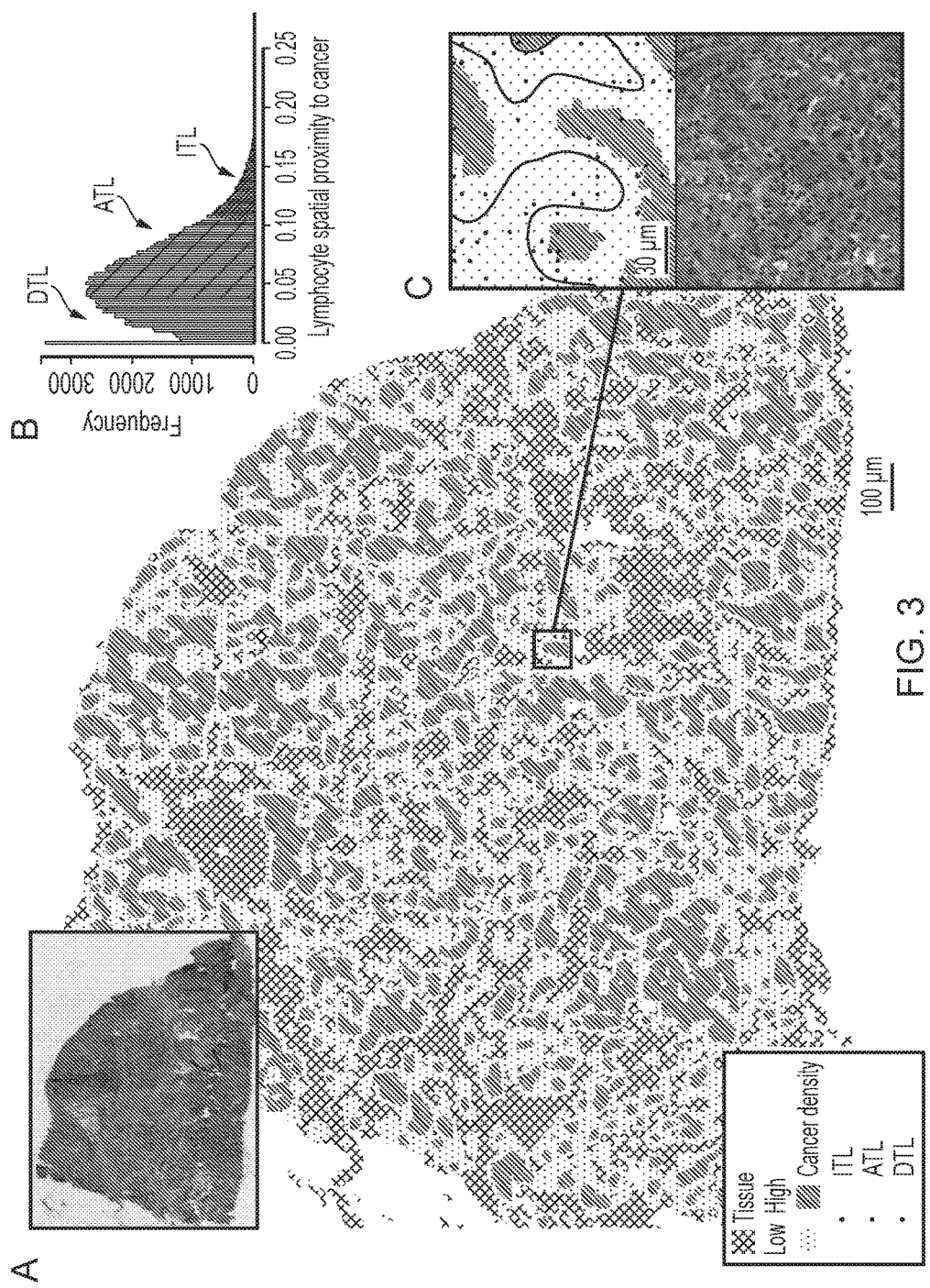

FIG. 3. A representative example illustrating three classes of lymphocytes in cancer density map of a tumour (middle section).

A. Density map of cancer and the spatial distribution of three classes of lymphocytes (spatial points coloured according to the classes). Black contour lines denote cut-off thresholds for the three classes of lymphocytes according to cancer density. B. Histogram showing the three types of lymphocytes in this sample. C. A higher resolution image of a region in this sample; colour codes follow A.

Figure 4:
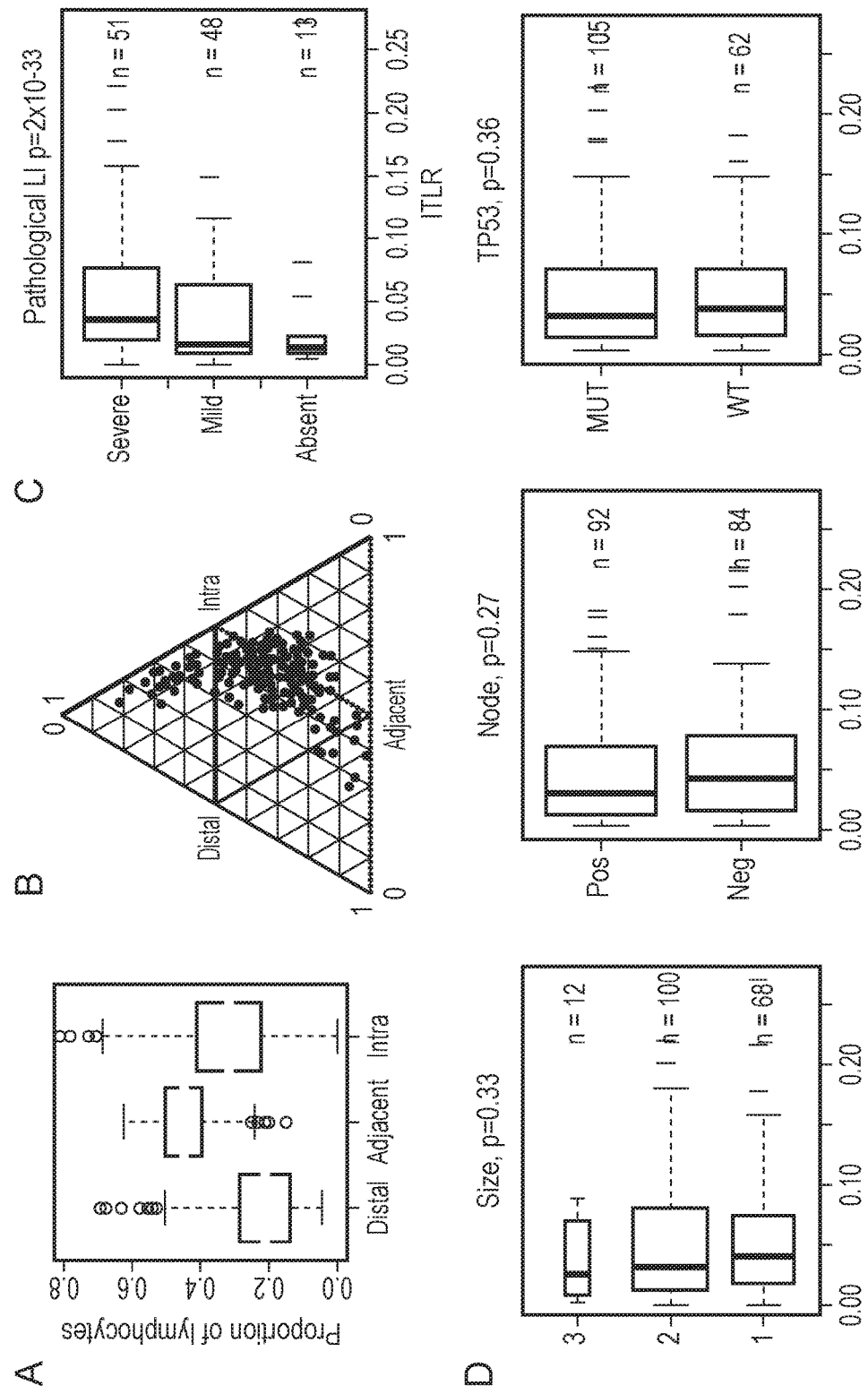
Figure 4:
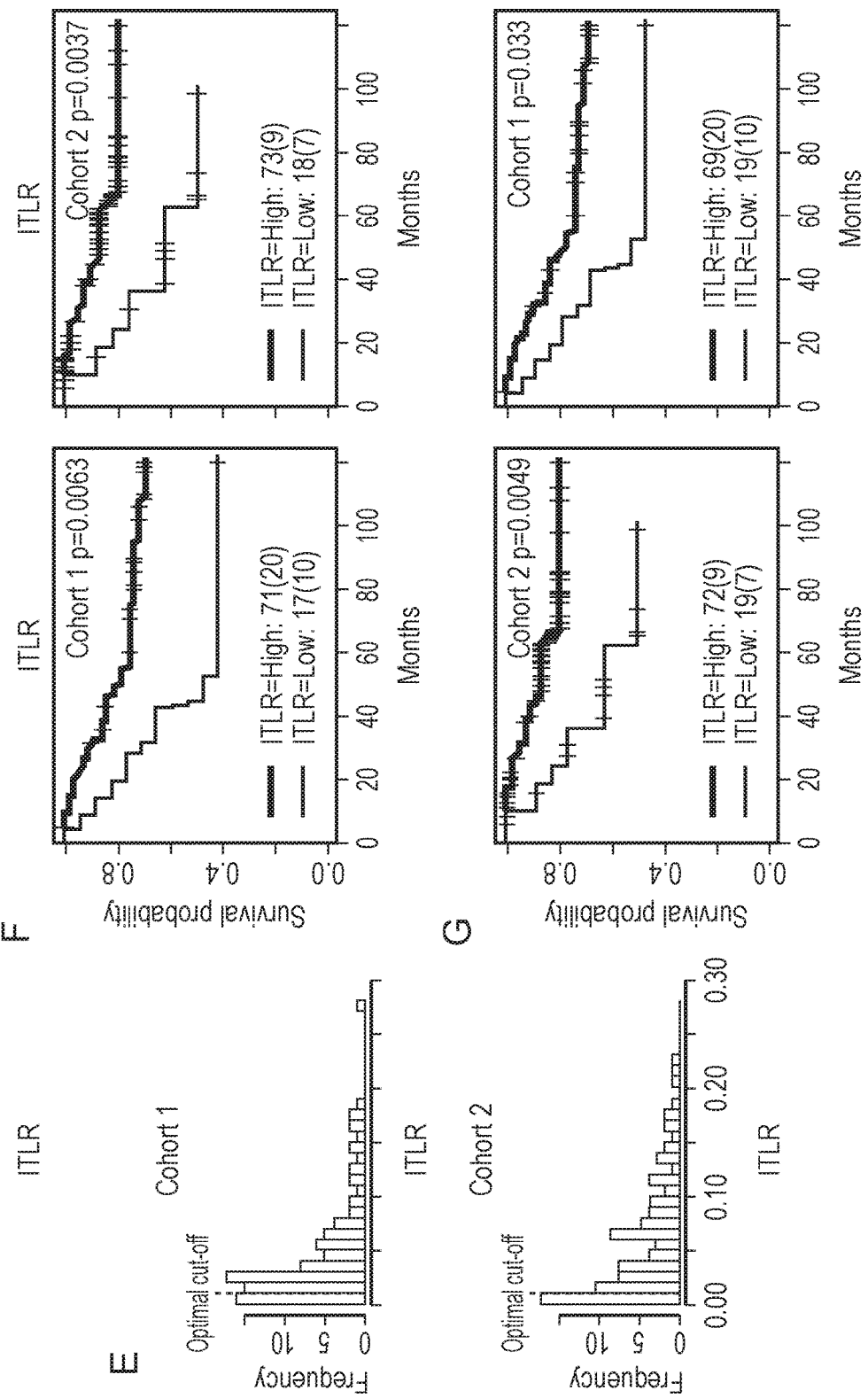

FIG. 4. Association between ITLR and clinical parameters of TNBC.

A. Proportions of three classes of lymphocytes in 181 TNBCs. B. Triangle plot to show the lymphocyte composition for each tumour (each black dot represents a tumour; thin lines mark the 50% of corresponding axis). C. Boxplot to show correlation between pathological scores and ITLR;

p-value from JT-test; n=patient number is each group; whiskers extend to 1.5 interquantile range. D. Association between ITLR and tumour size, node status and TP53 mutations; whiskers extend to 1.5 interquantile range. E. Distribution of ITLR in two cohorts with optimal cut-offs marked as dashed red lines. F. Kaplan-Meier curves to illustrate the disease-specific survival probabilities of patient groups in two TNBC cohorts stratified by ITLR using the cut-off selected in Cohort 1. Numbers in the legend show the number of patients in each group and numbers in the bracket show the number of disease-specific deaths. G. Using Cohort 2 as the discovery cohort and Cohort 1 as the validation cohort yielded similar optimal cut-off.

Figure 5:
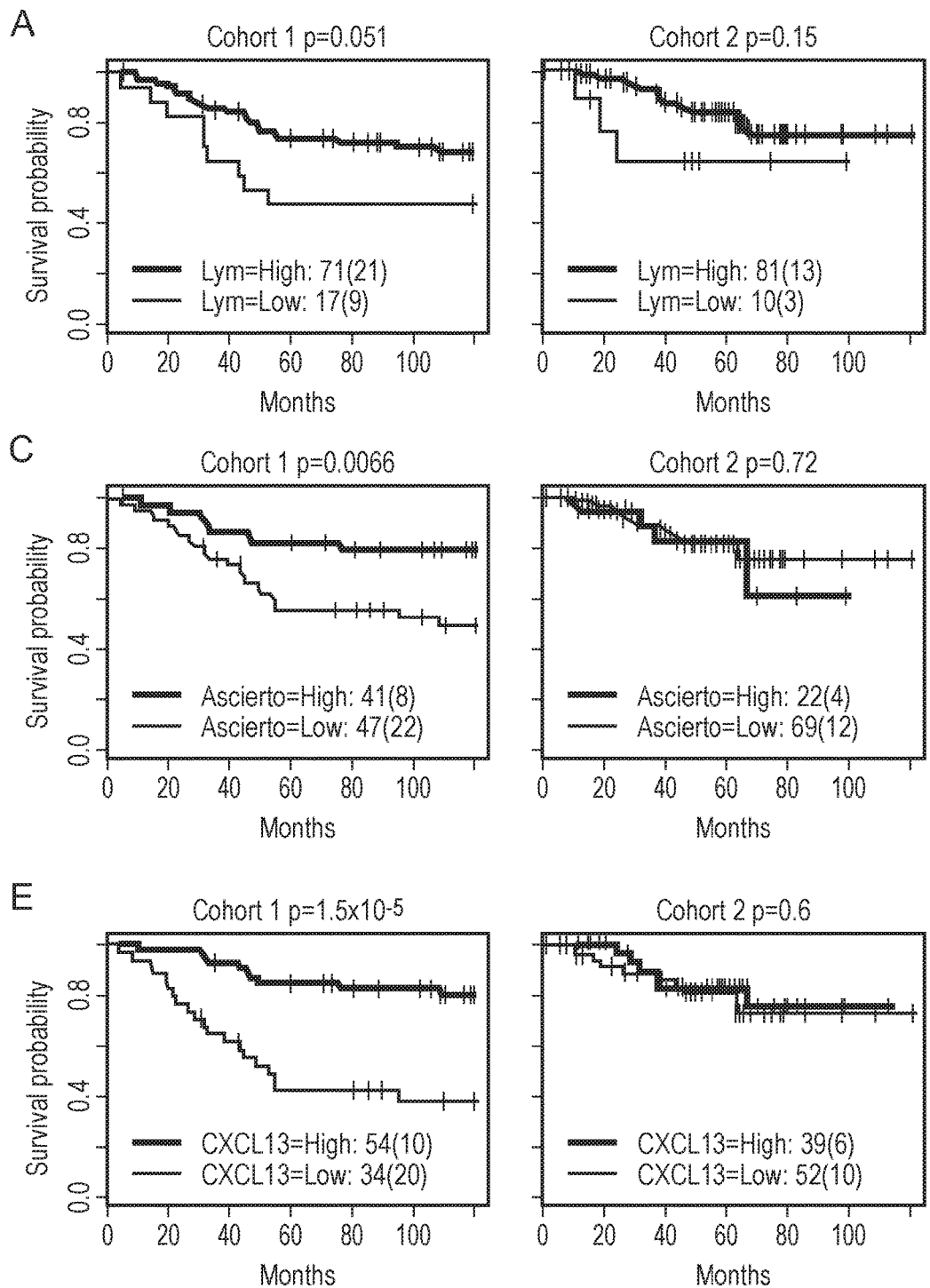
Figure 5:
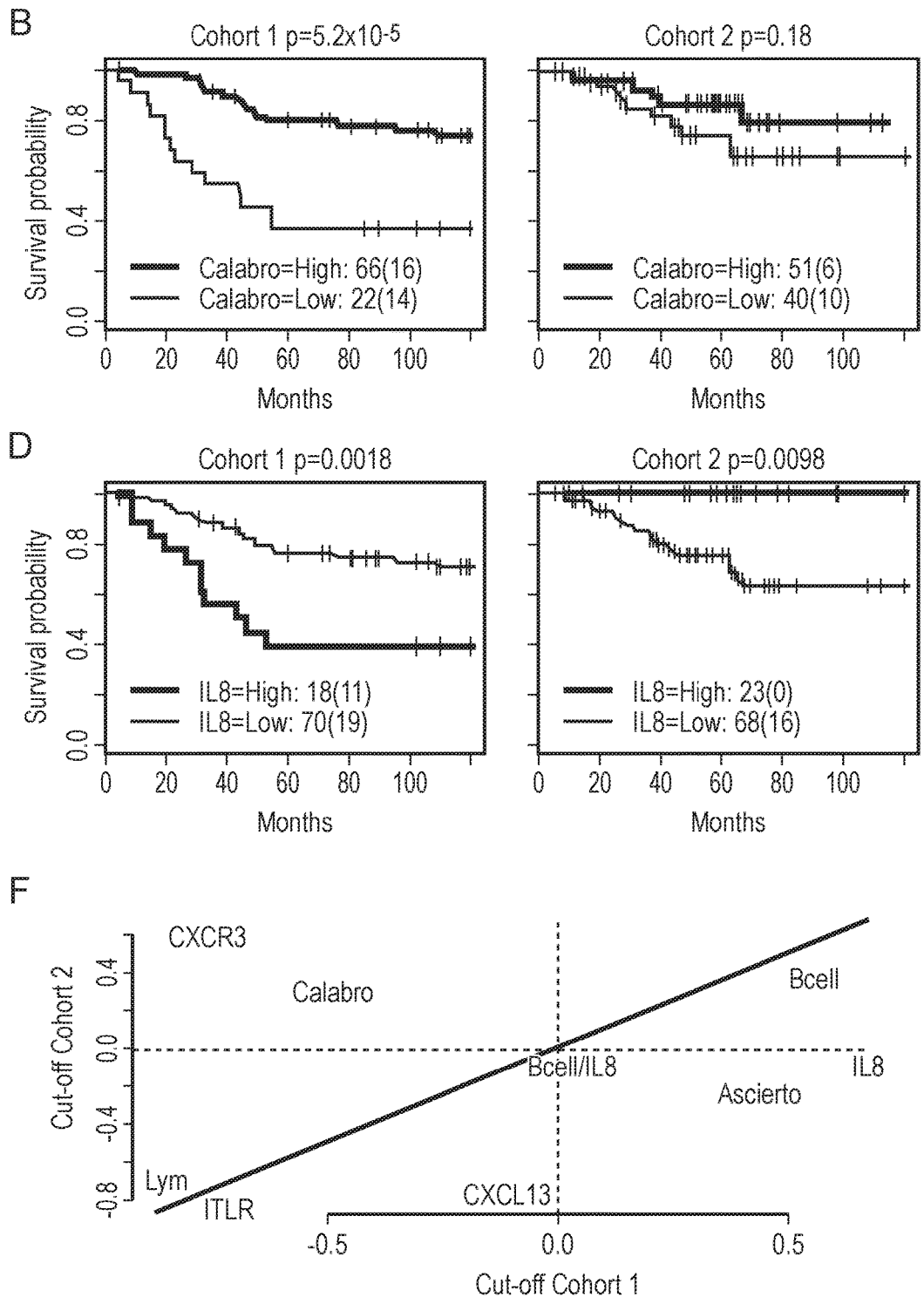

FIG. 5. Comparison of ITLR with other immune signatures.

The optimal cut-off were selected in Cohort 1 and tested in Cohort 2 for A. image-based lymphocyte abundance (Lym); B. gene expression immune signature by Calabro et al. (18); C. Ascierto et al. (19); D. IL8 signature (20); E. CXCL13 expression. F. Comparing optimal cut-offs selected in two cohorts. Data were centred at 0 and scaled to have standard deviation 1 and cut-offs were mapped to the centred, scaled data. Signatures close to the diagonal line have similar cut-offs in two cohorts.

Figure 6:
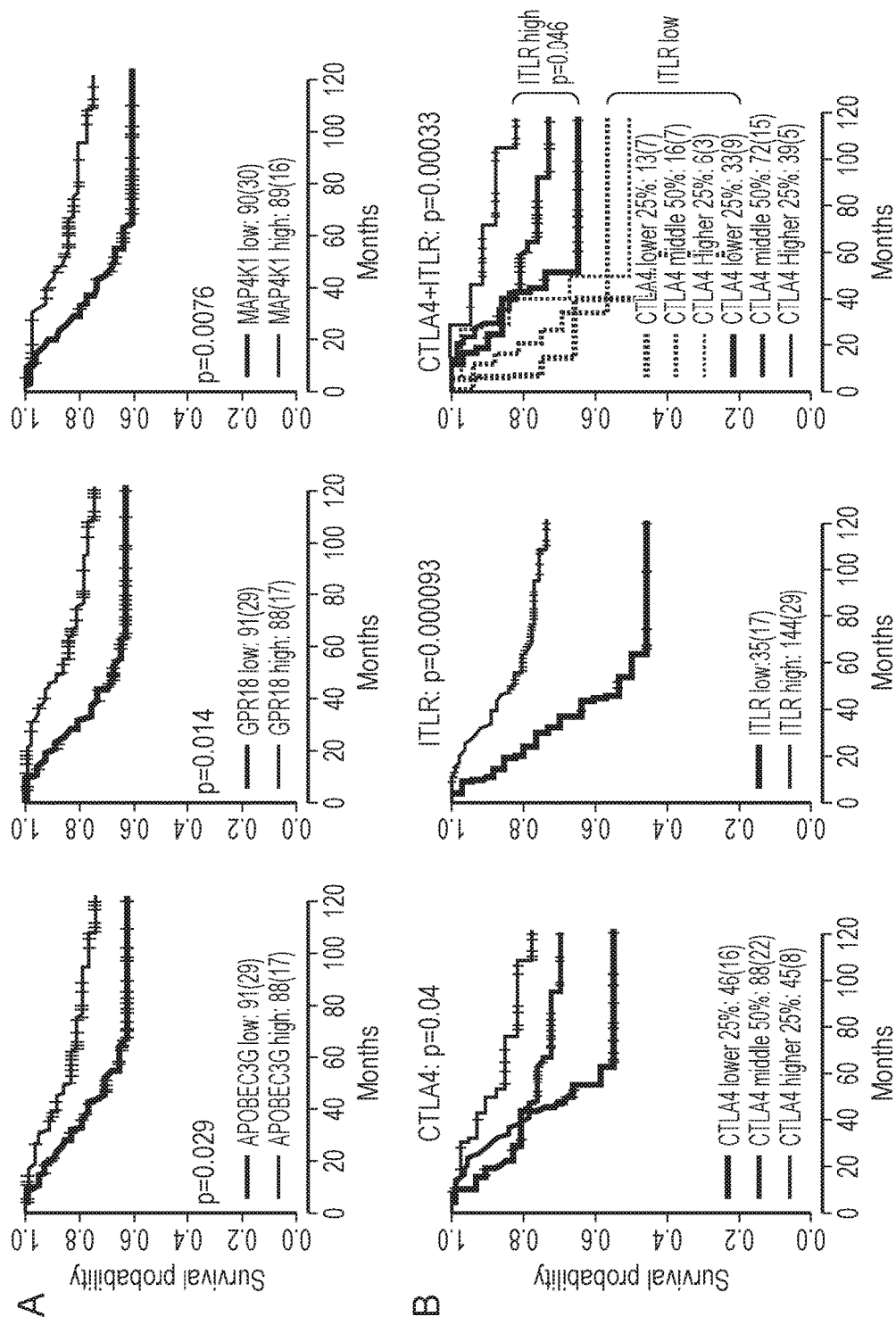

FIG. 6. ITLR-associated gene modules.

A. Kaplan-Meier curves to illustrate differences in disease-specific survival of patient groups of equal sizes stratified based on the expression of key genes in three modules. B. Kaplan-Meier curves to illustrate differences in disease-specific survival of patient groups stratified with CTLA4 expression by the lower 25, middle 50 and higher 25 percentiles, ITLR, and CTLA4 and ITLR combined. Survival difference between CTLA low and high stratification within the ITLR high group is given as a p-value.

Figure 7:
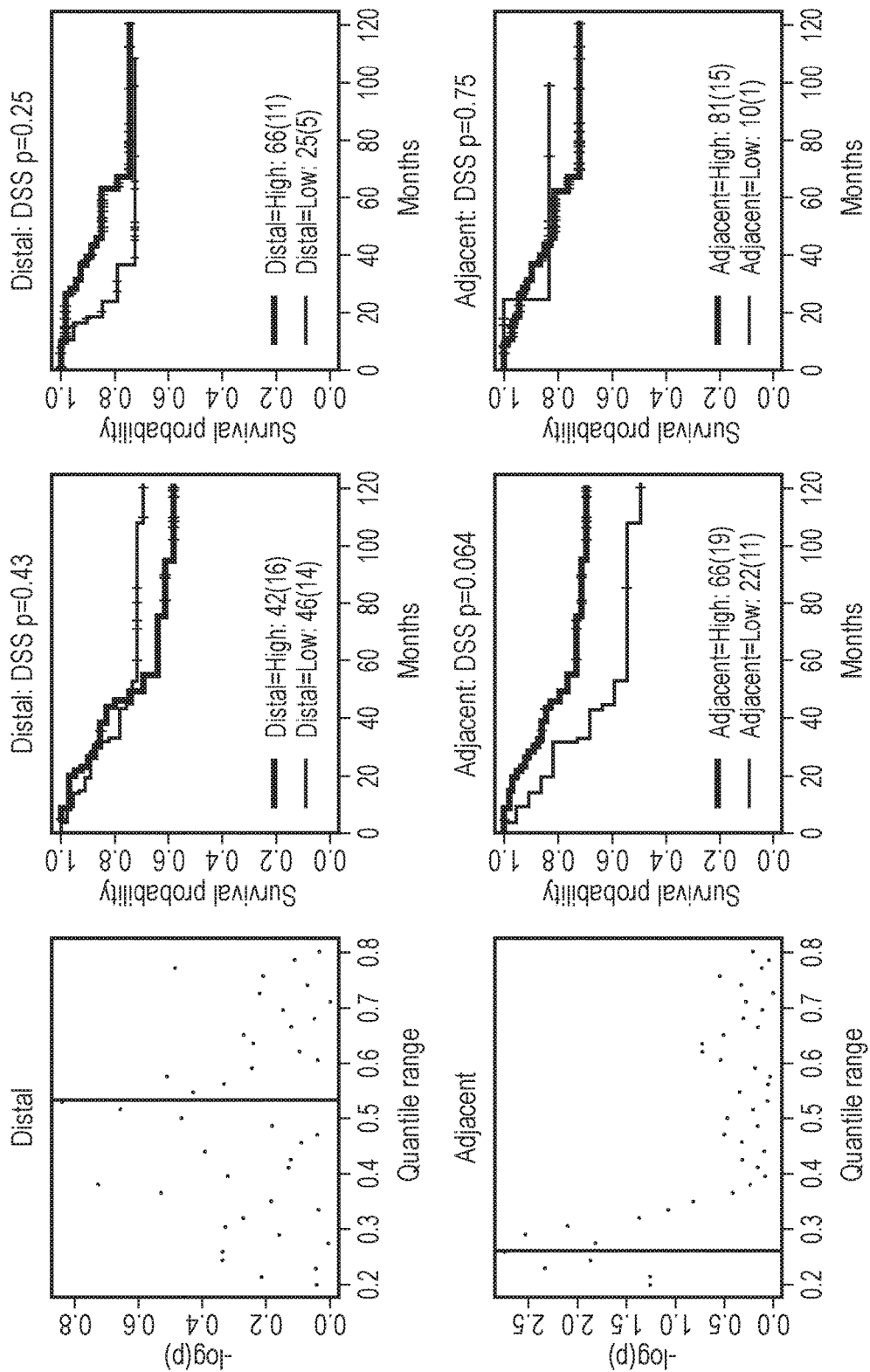

FIG. 7. Kaplan-Meier curves to illustrate the disease-specific survival probabilities of patient groups in two TNBC cohorts stratified by ATLR (Adjacent) and DTLR (Distal).

The signatures were dichotomised using a cut-off selected over a range of percentiles based on Cohort 1 (the left and middle columns) and tested in Cohort 2 (the right column). Dashed lines in the plots on the left marks the significance threshold of p=0.05, and solid vertical lines show the best cut-offs. For the Kaplan-Meier curves, the numbers in the legend show the number of patients in each group and numbers in the bracket show the number of disease-specific deaths.

Figure 8:
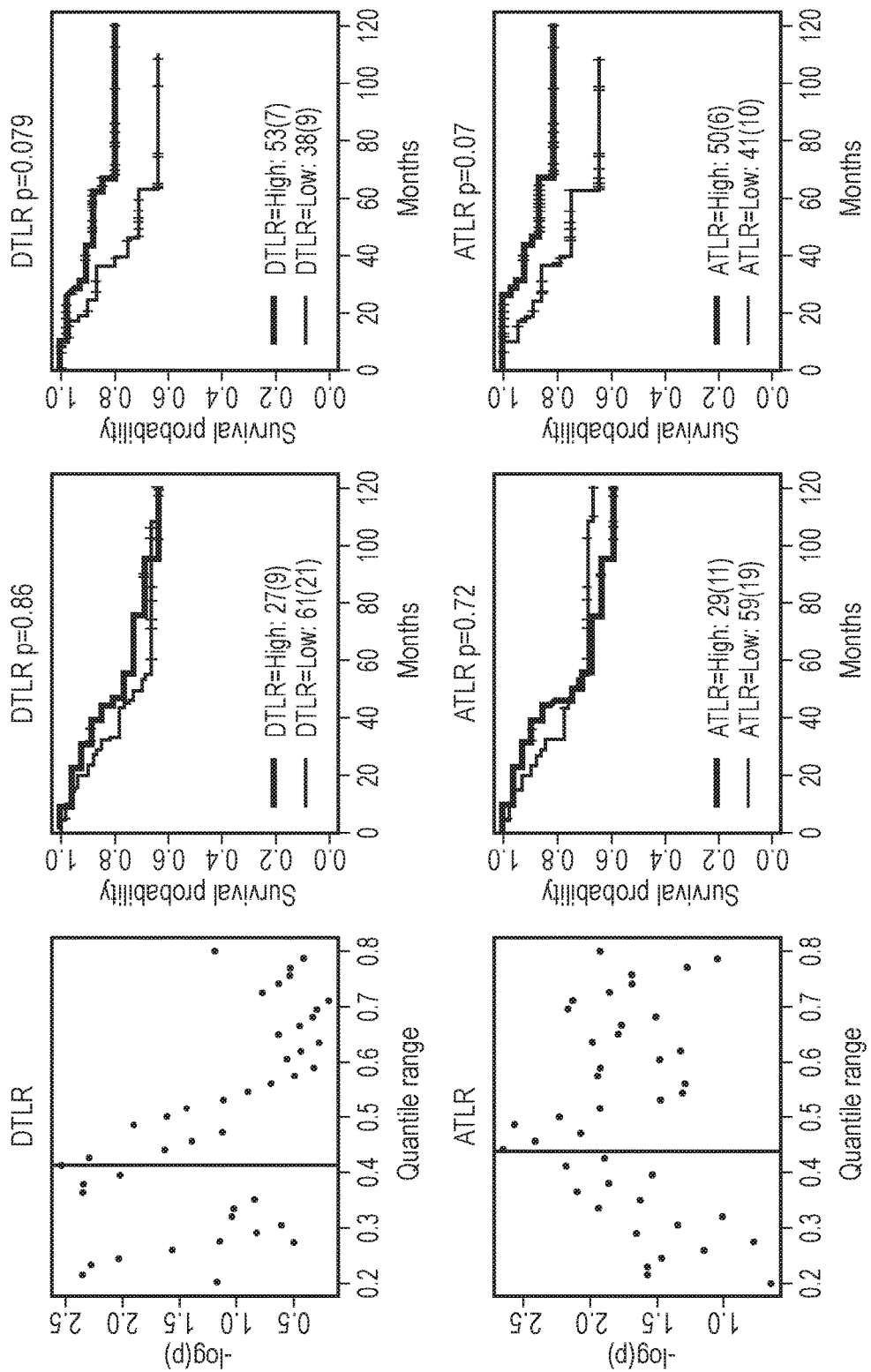

FIG. 8. Kaplan-Meier curves to illustrate the disease-specific survival probabilities of patient groups in two TNBC cohorts stratified by ATLR (Adjacent) and DTLR (Distal).

The signatures were dichotomised using a cut-off selected over a range of percentiles based on Cohort 2 (the left and right columns) and tested in Cohort 1 (the middle column).

Figure 9:
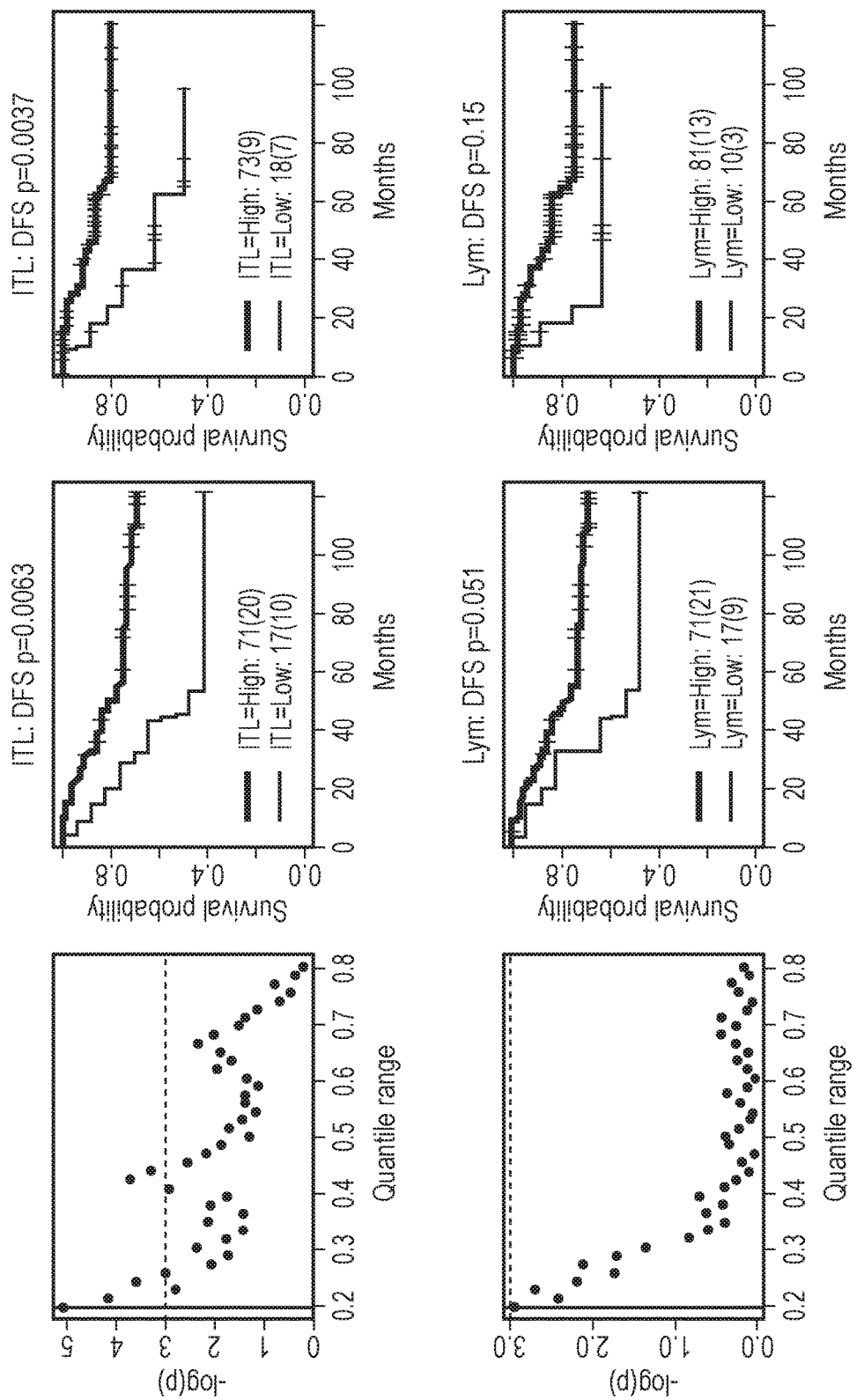
Figure 9:
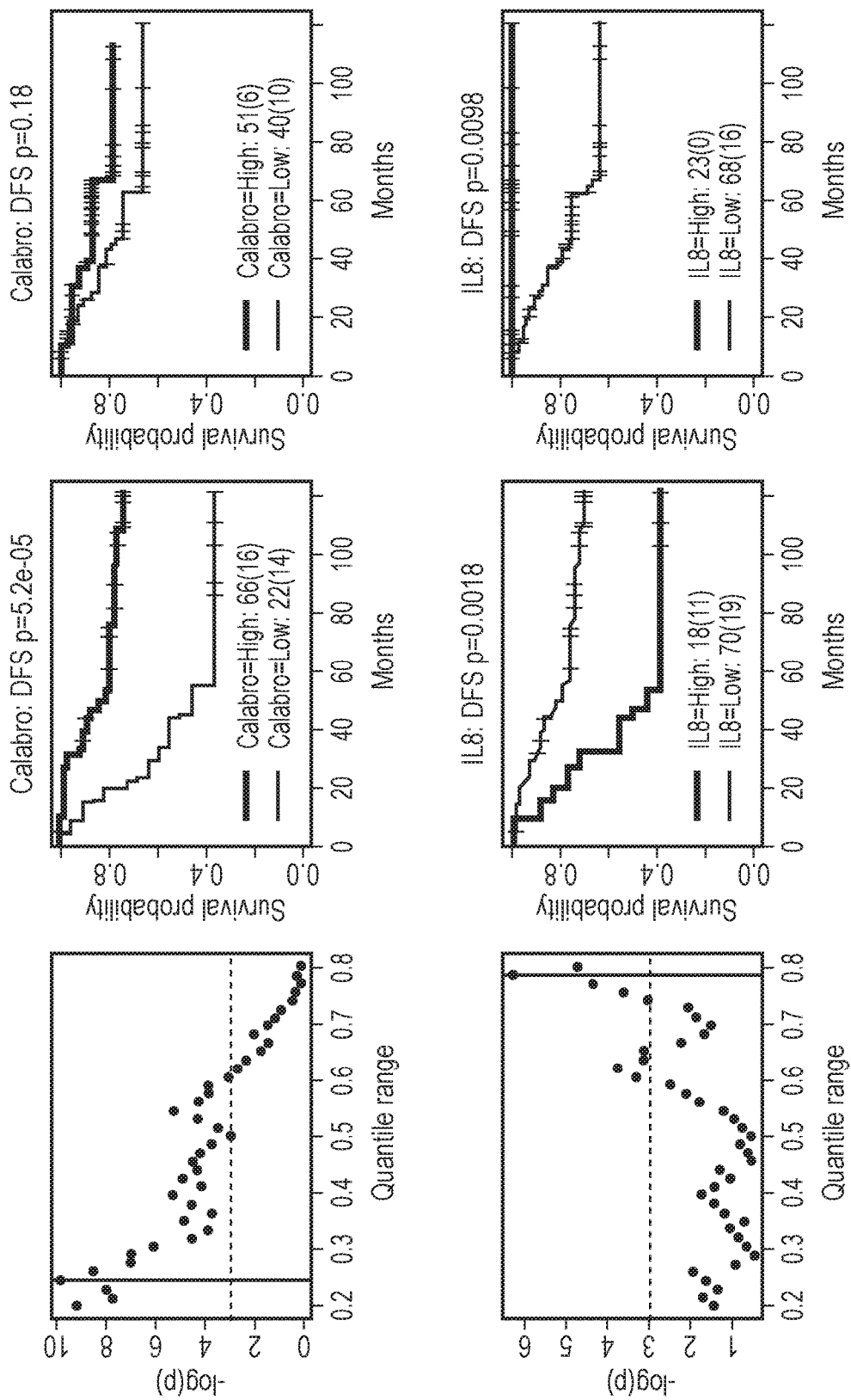
Figure 9:
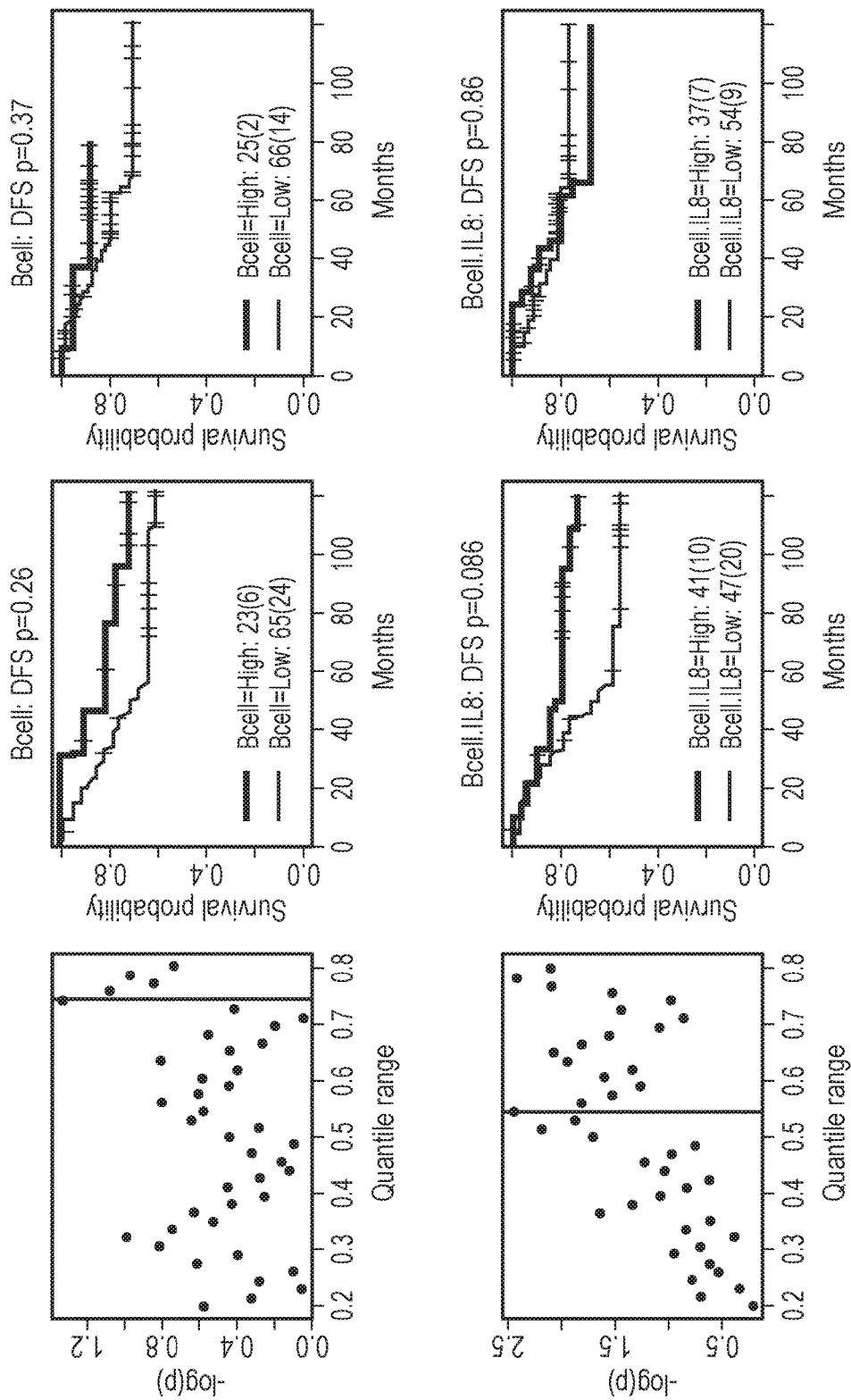
Figure 9:
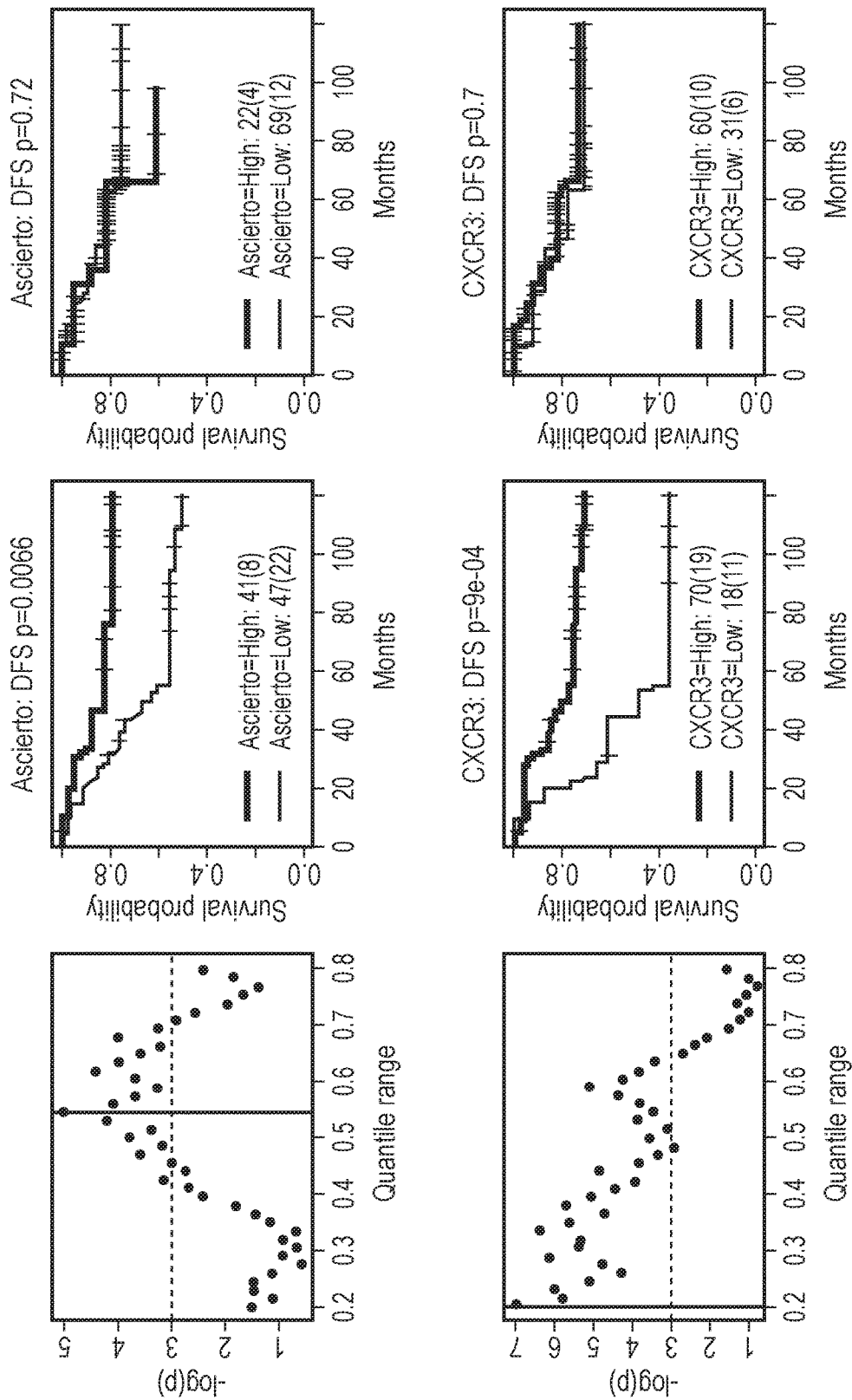
Figure 9:
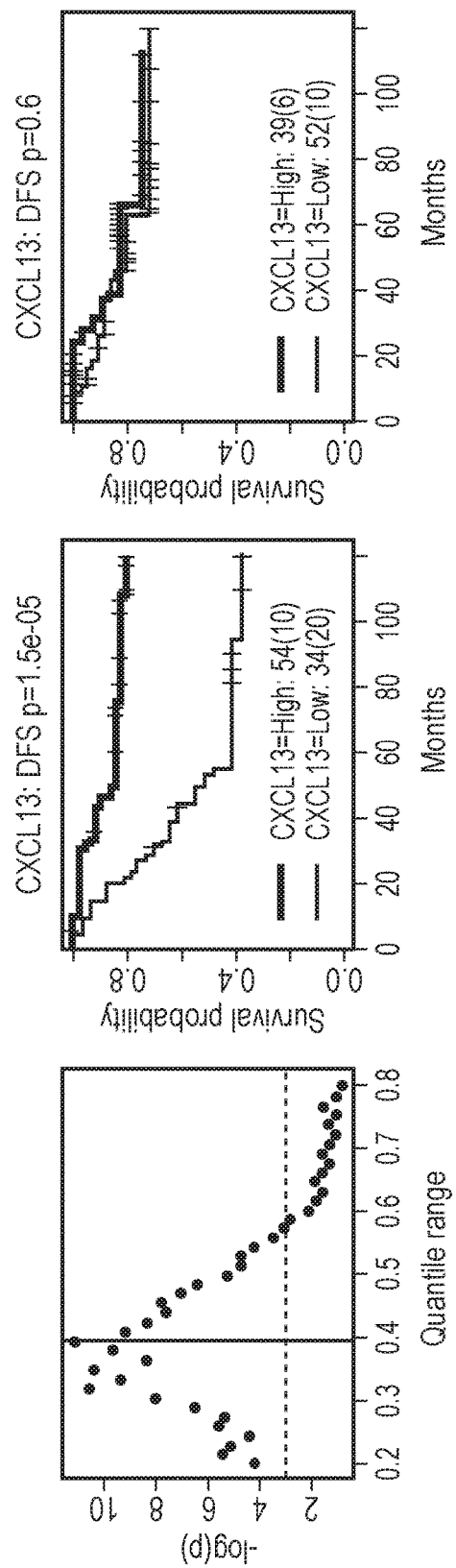

FIG. 9. Kaplan-Meier curves to illustrate the disease-specific survival probabilities of patient groups in two TNBC cohorts stratified by nine immune signatures.

The signatures were dichotomised using a cut-off selected over a range of percentiles based on Cohort 1 (the left and middle columns) and tested in Cohort 2 (the right column). Dashed lines in the plots on the left marks the significance threshold of p=0.05, and solid vertical lines show the best cut-offs. For the Kaplan-Meier curves, the numbers in the legend show the number of patients in each group and numbers in the bracket show the number of disease-specific deaths.

Figure 10:
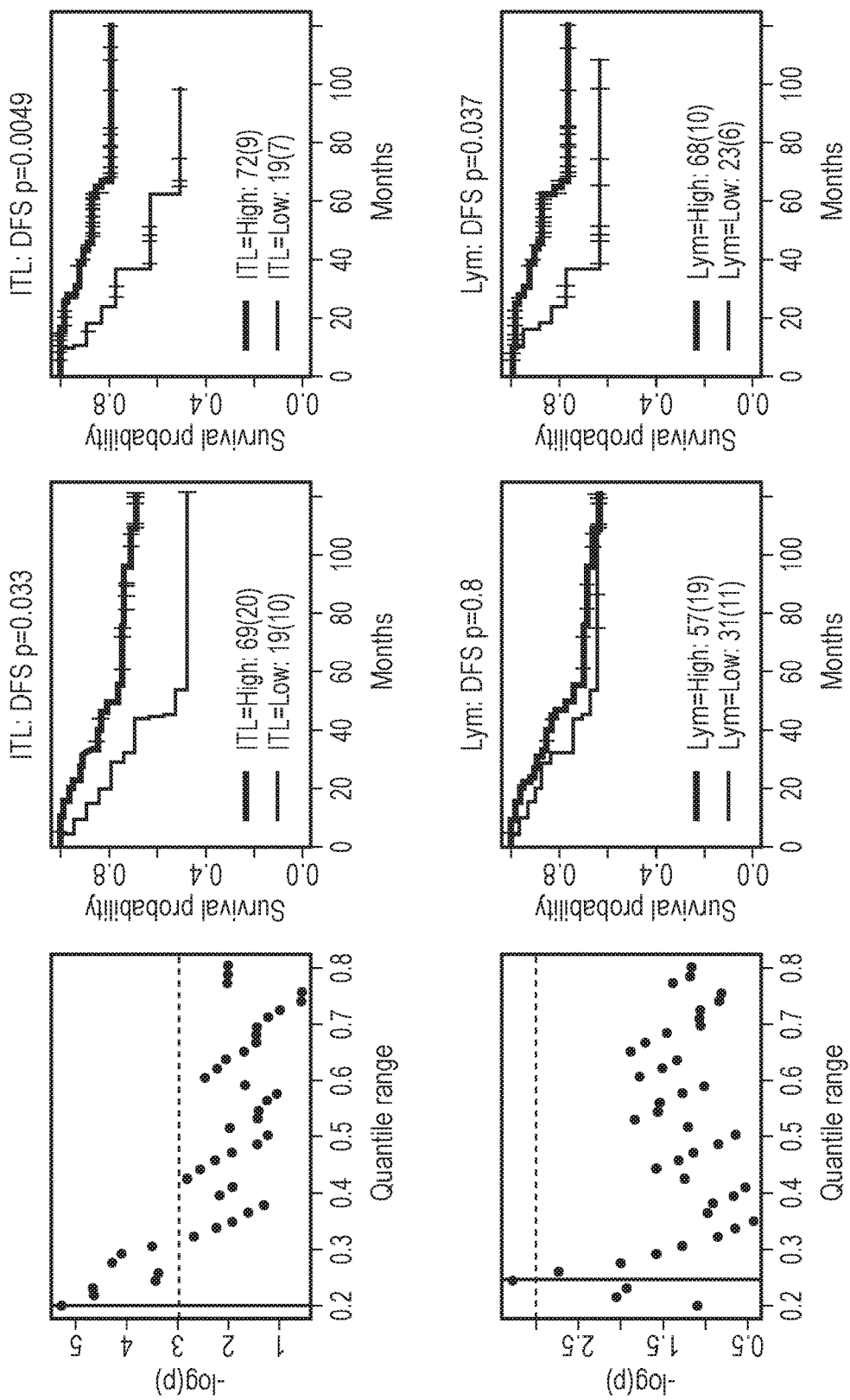
Figure 10:
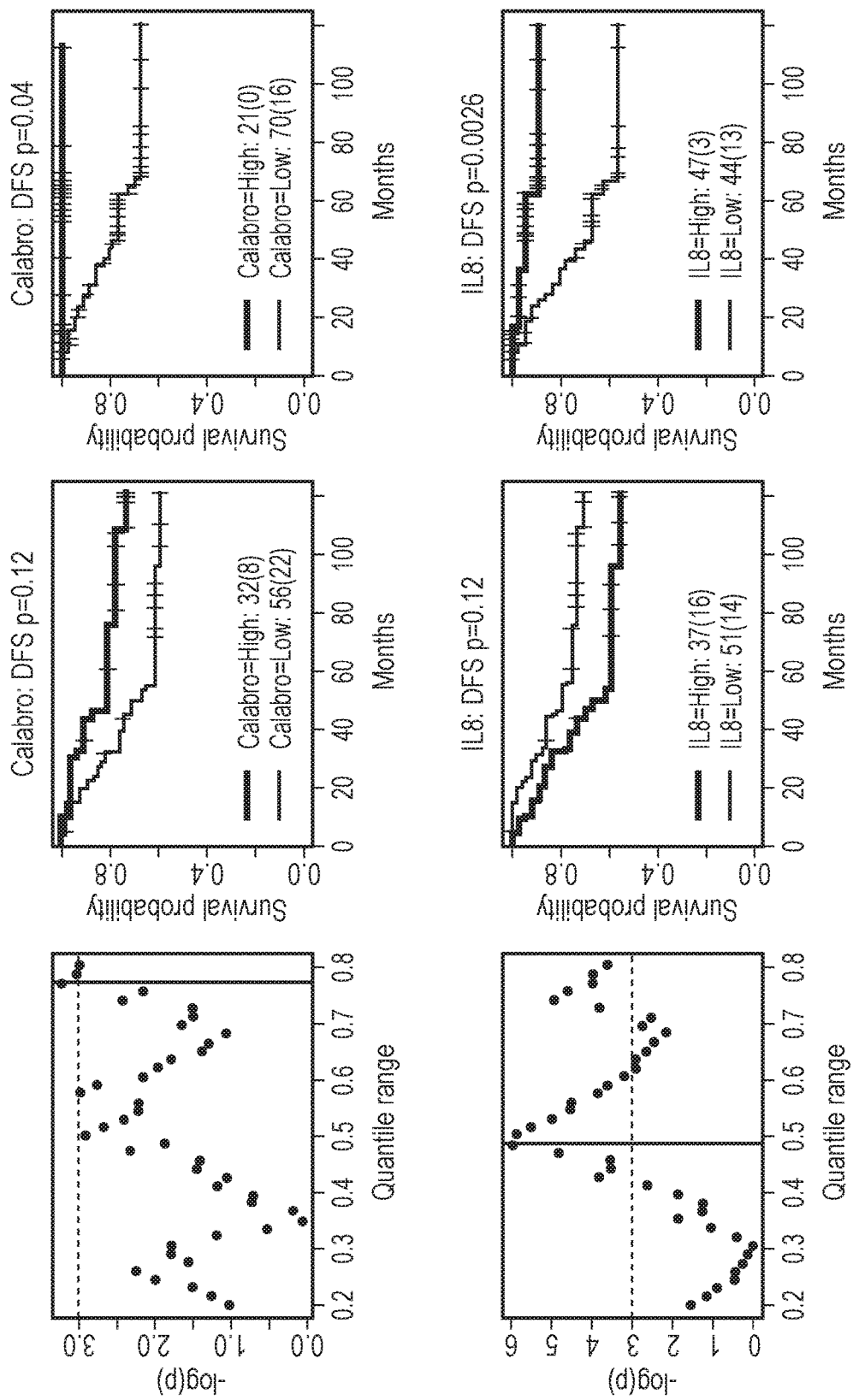
Figure 10:
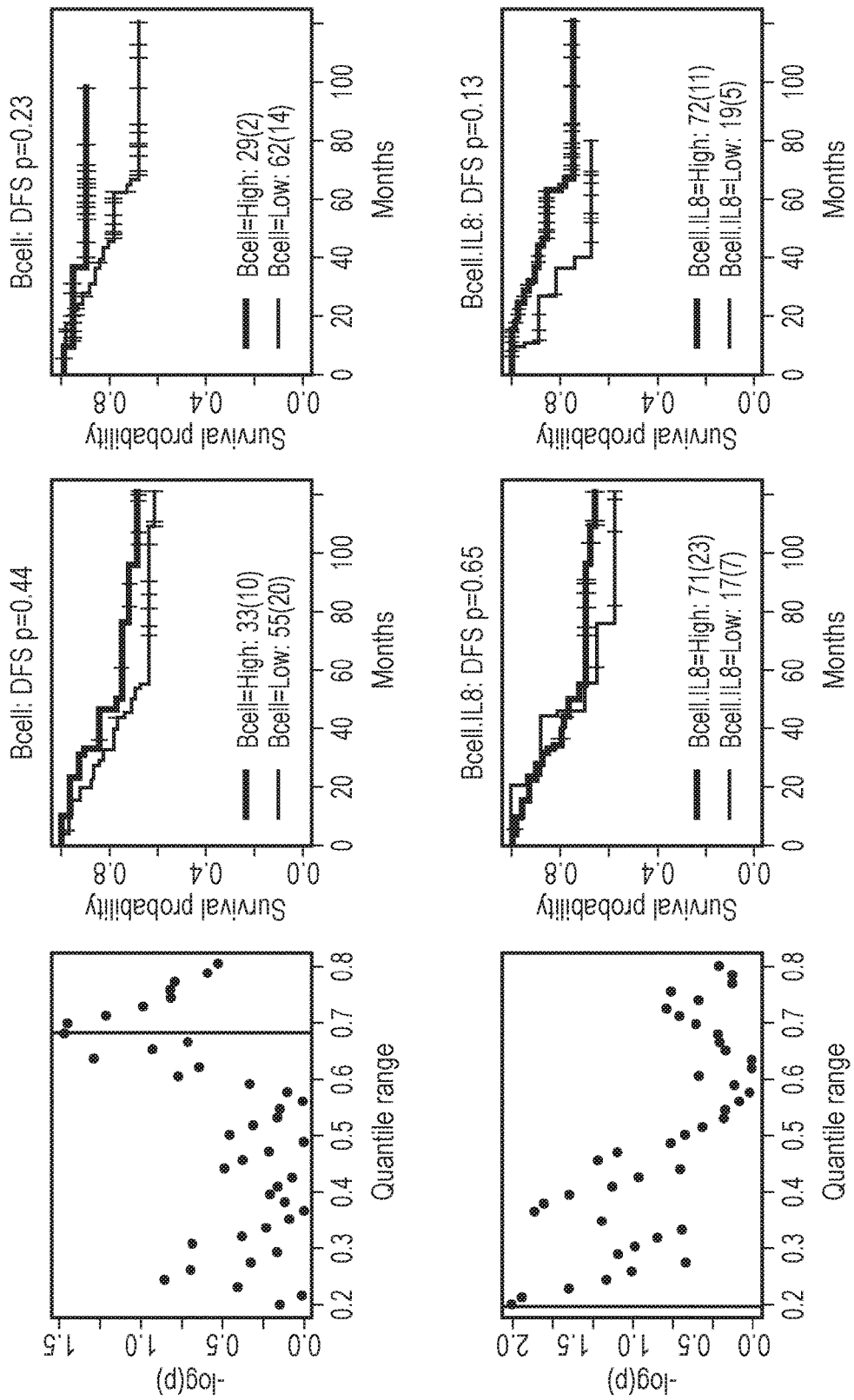
Figure 10:
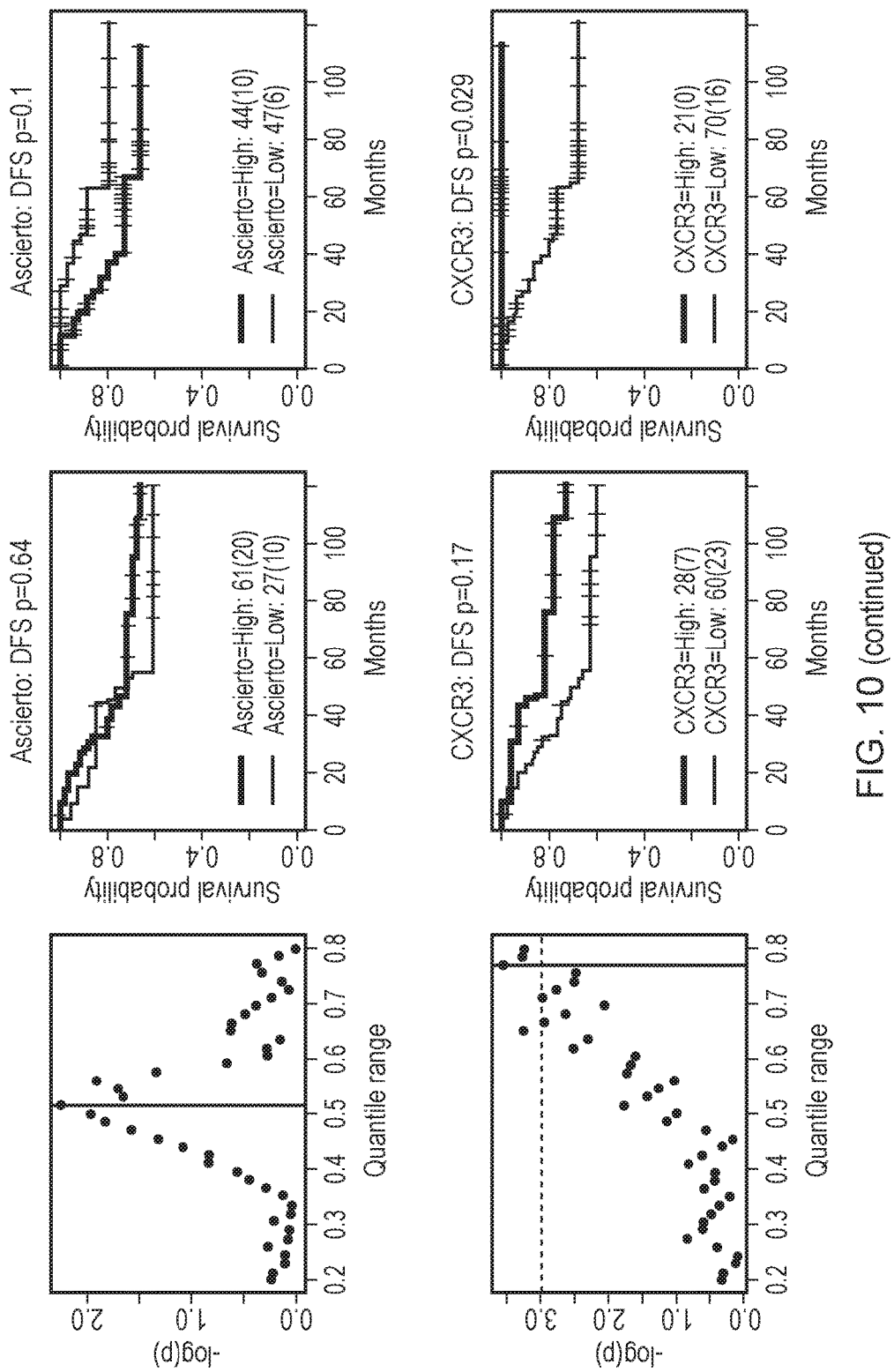
Figure 10:
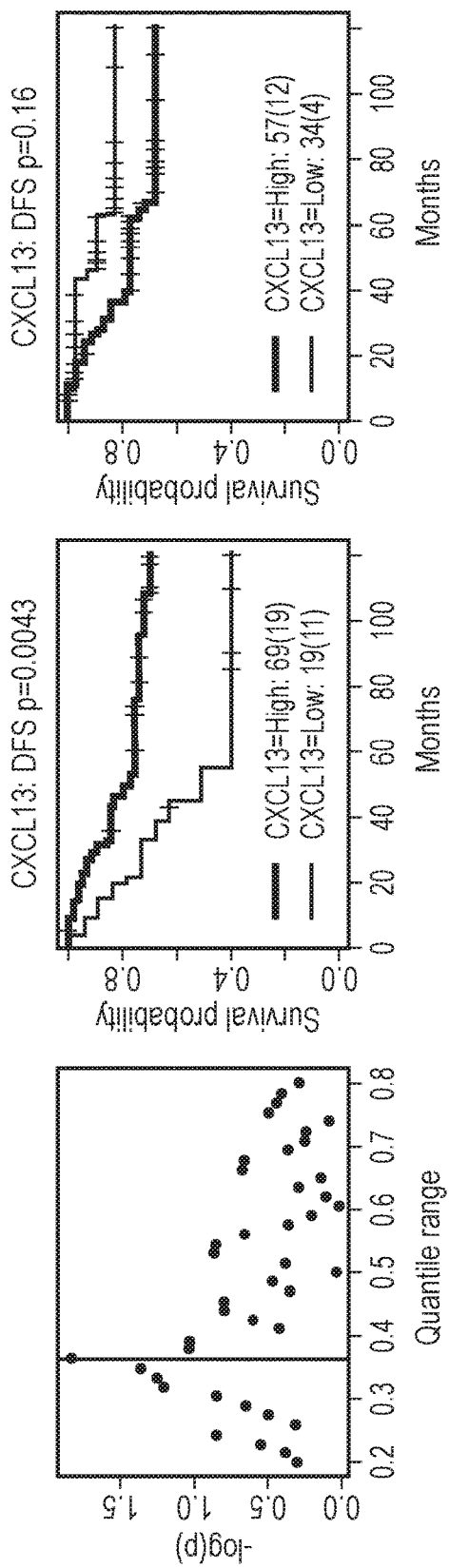

FIG. 10. Kaplan-Meier curves to illustrate the disease-specific survival probabilities of patient groups in two TNBC cohorts stratified by nine immune signatures.

The signatures were dichotomised using a cut-off selected over a range of percentiles based on Cohort 2 (the left and right columns) and tested in Cohort 1 (the middle column). Dashed lines in the plots on the left marks the significance threshold of p=0.05, and solid vertical lines show the best cut-offs. For the Kaplan-Meier curves, the numbers in the legend show the number of patients in each group and numbers in the bracket show the number of disease-specific deaths.

Figure 11:
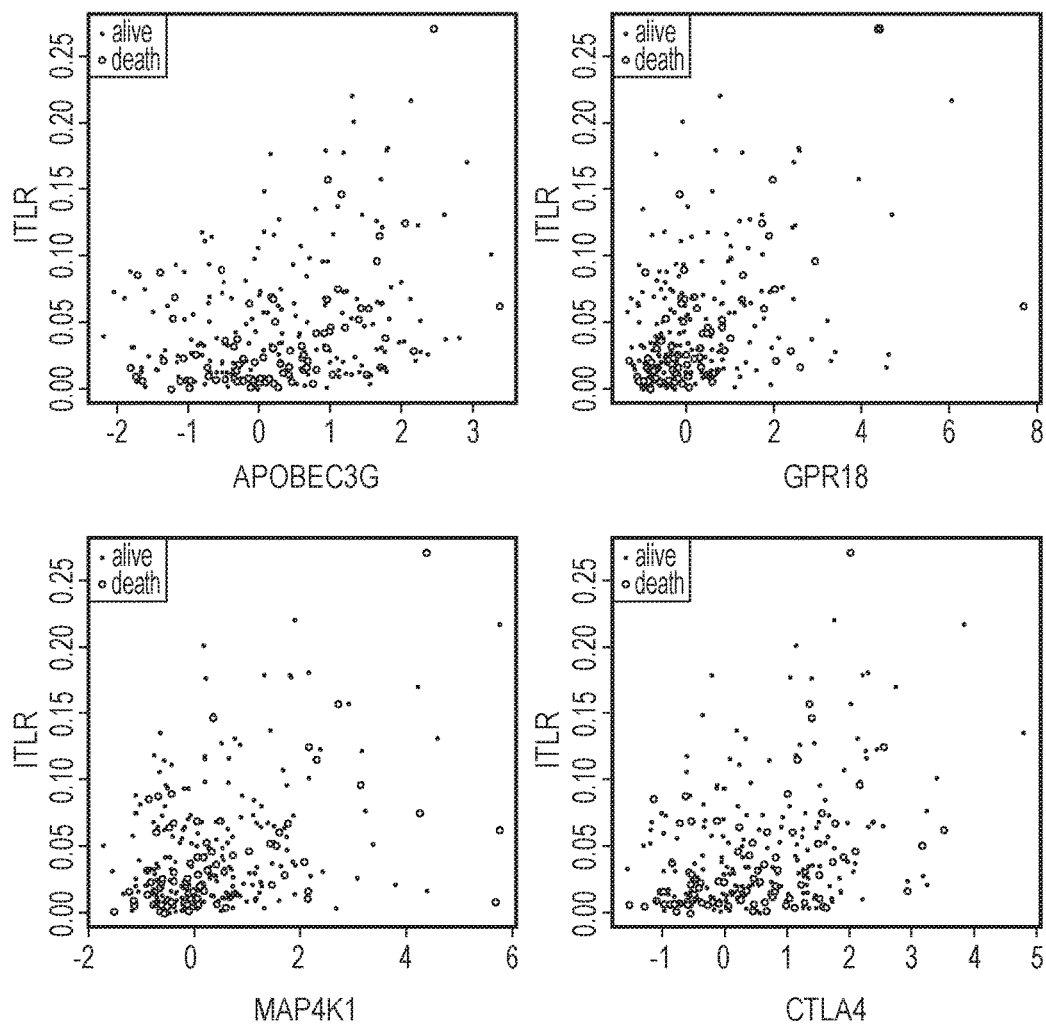

FIG. 11. Scatter plots to show correlation between ITLR and expression of ITLR-associated genes in TNBC.

Figure 12:
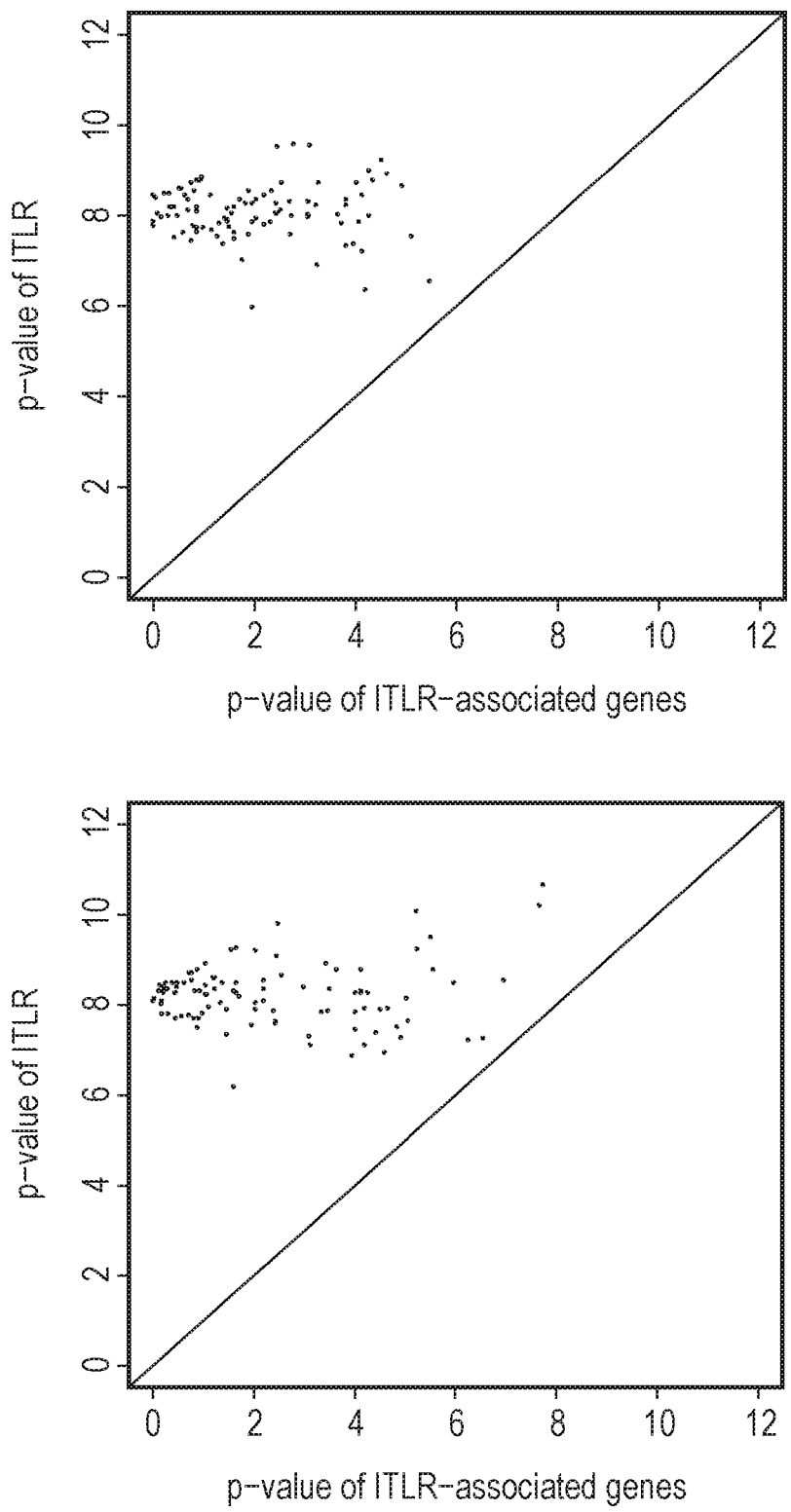

FIG. 12. Compare the prognostic value of top 100 ITLR-associated genes and ITLR by including both in multivariate Cox analysis model, one gene at a time.

Each point denotes analysis for one gene, plotted values are log(log rank p-value) for the analysis.

Figure 13:
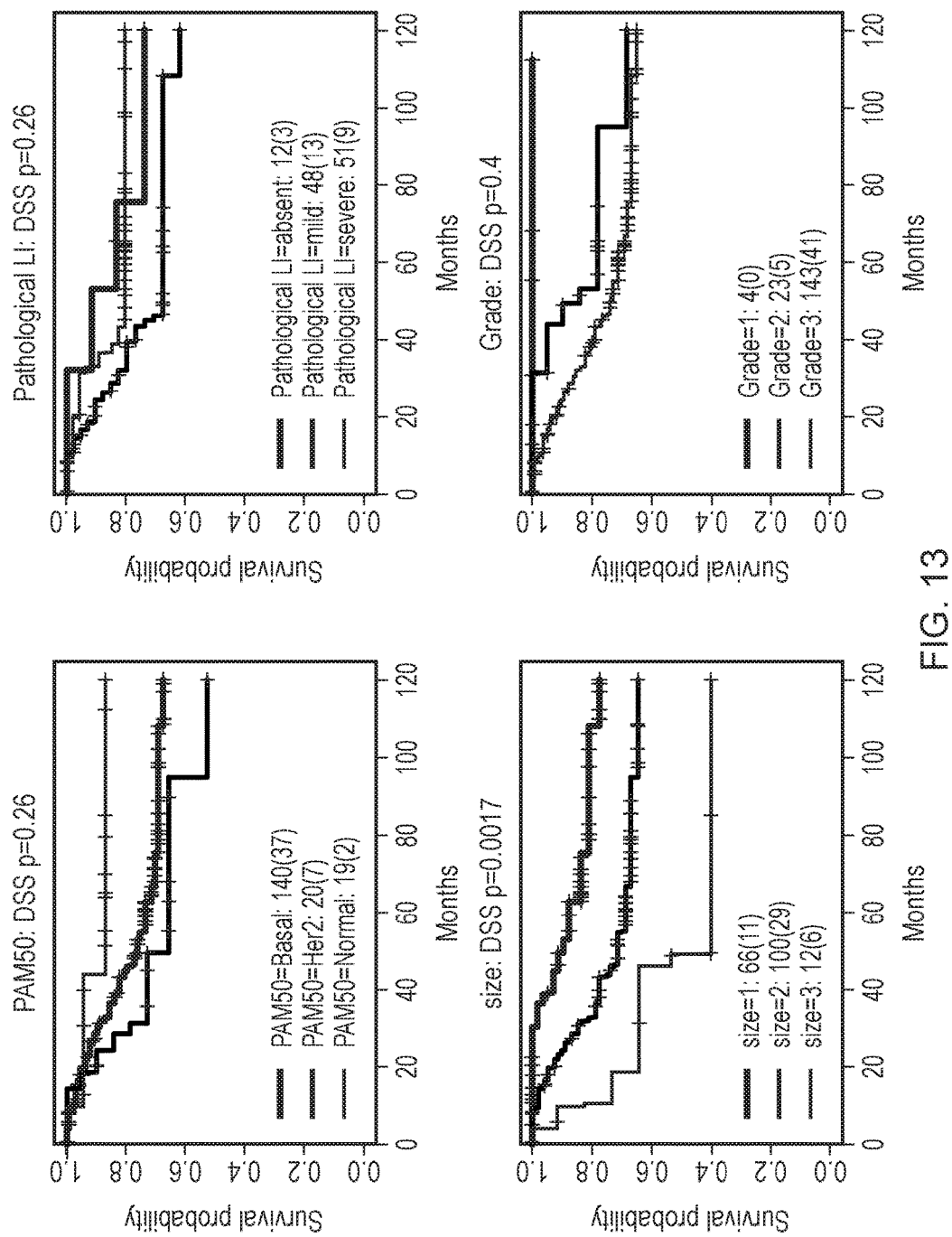

FIG. 13. Kaplan-Meier curves illustrating differences in disease-specific survival of TNBC patients stratified with other known parameters including PAM50 (Perou et al., 2000), pathological assessment of lymphocytic infiltration (LI), tumour size, and grade.

Figure 14:
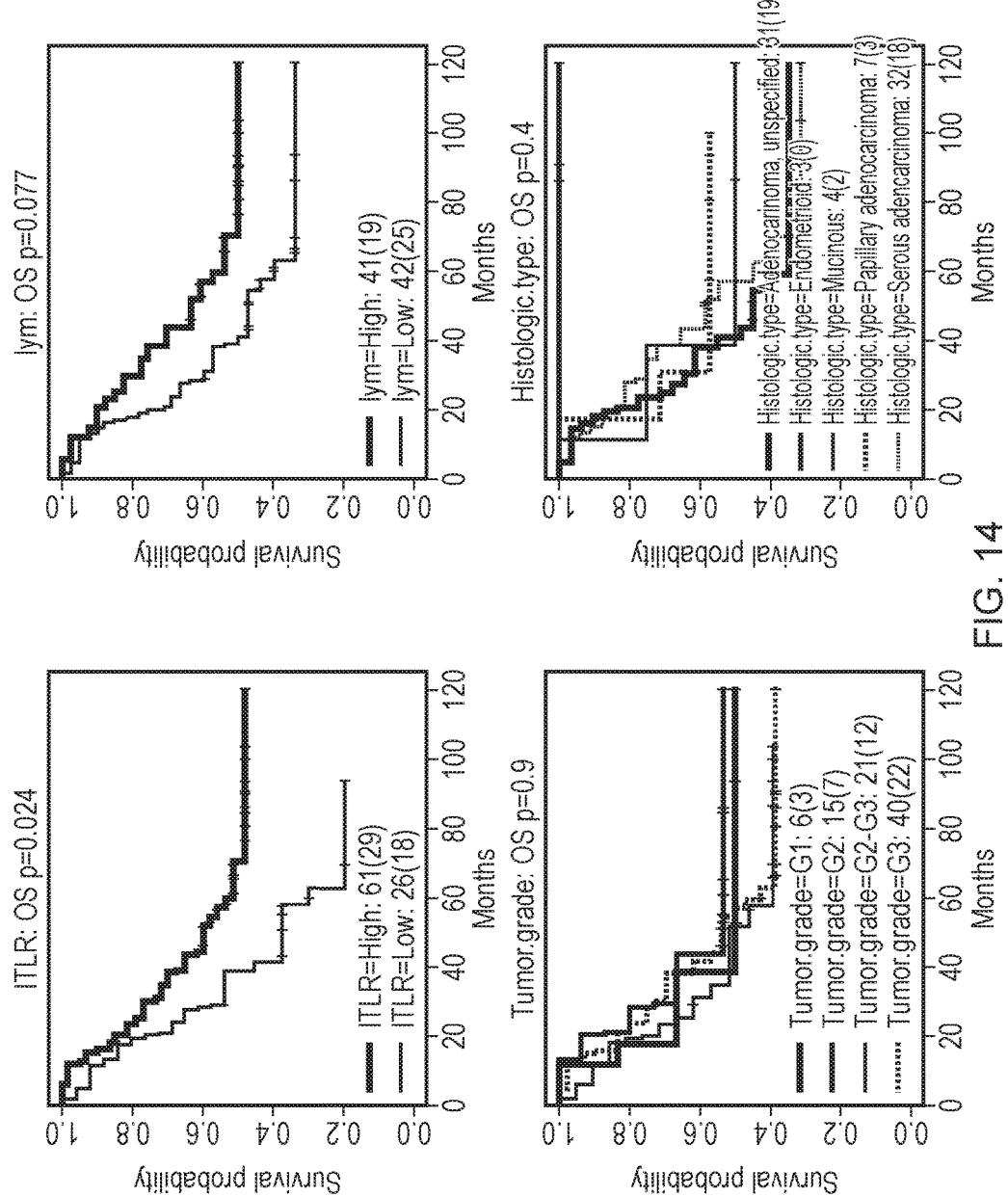
Figure 14:
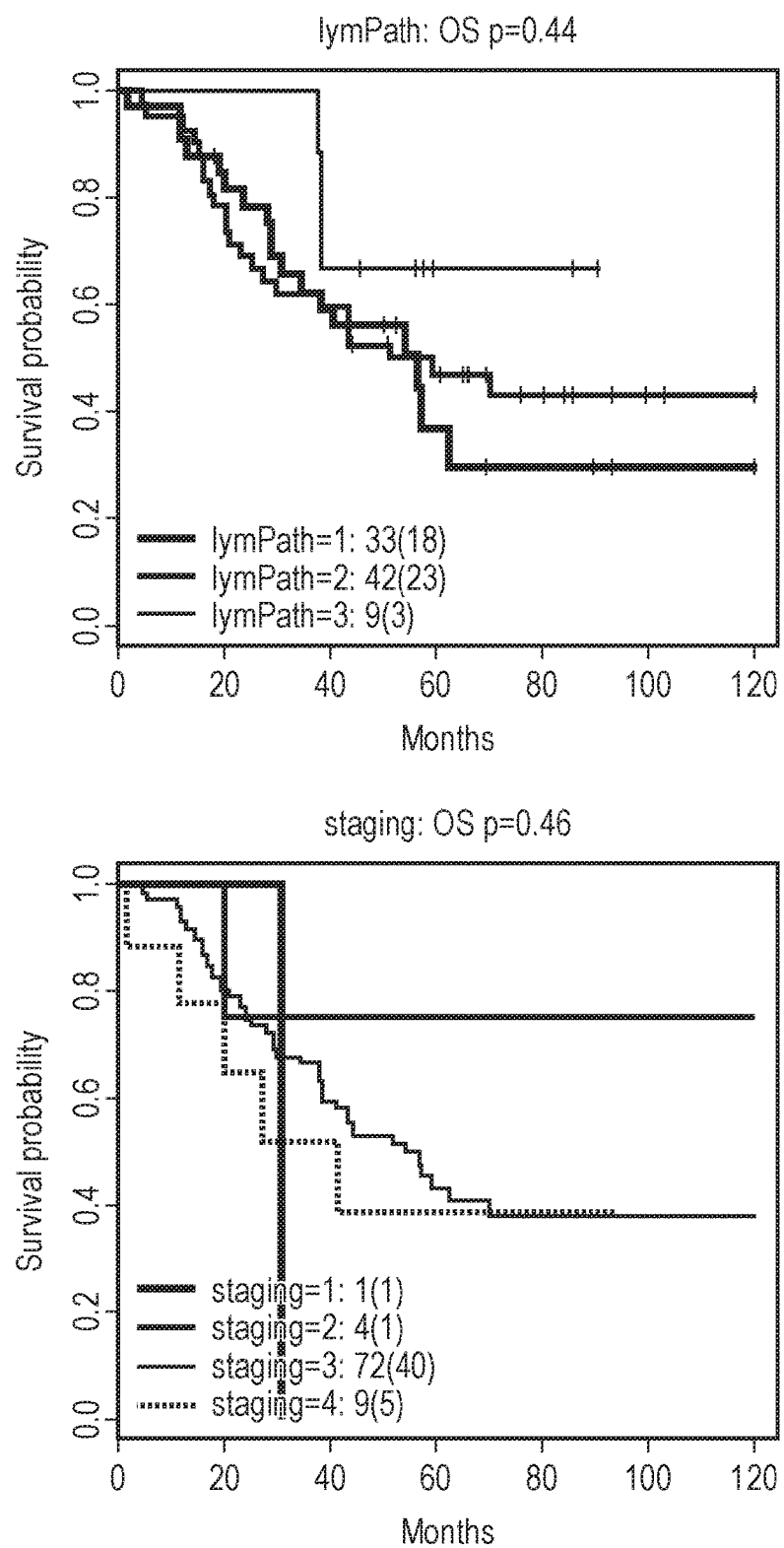

FIG. 14. Kaplan-Meier curves illustrating differences in 5-year overall survival of ovarian cancer patients of patient groups stratified by ITLR, by "Lym" (Yuan et al., 2012), by lymPath (lymphocyte abundance assessed by pathologist), tumour grade, histologic type, or tumour staging.

Figure 15:
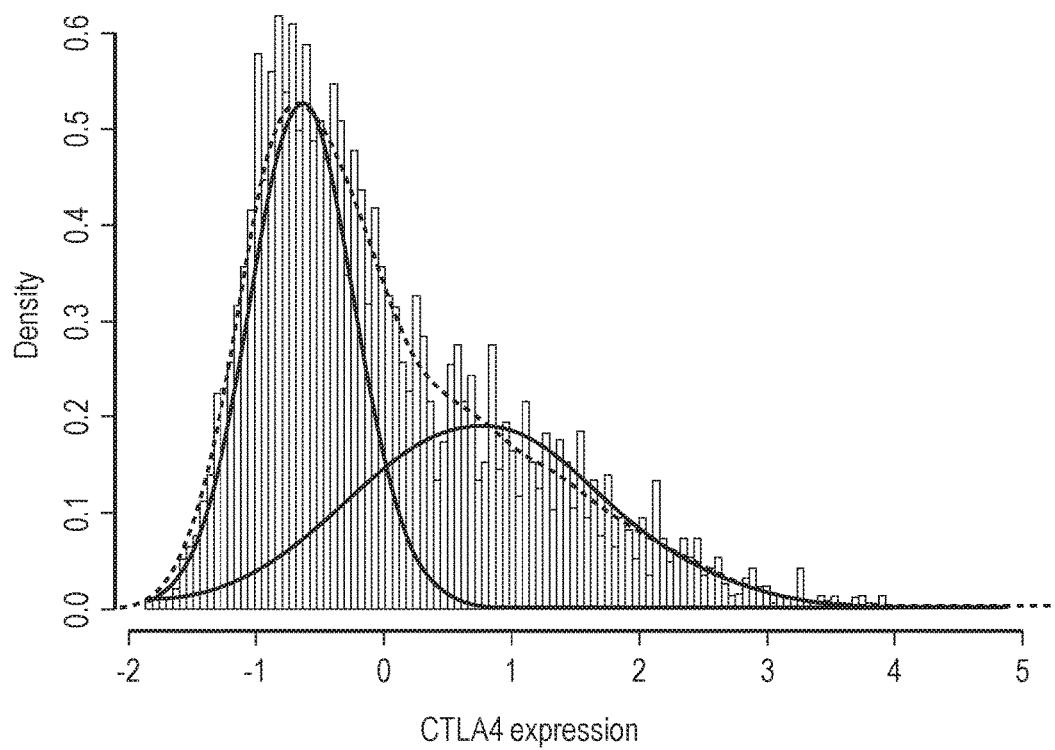
Figure 15:
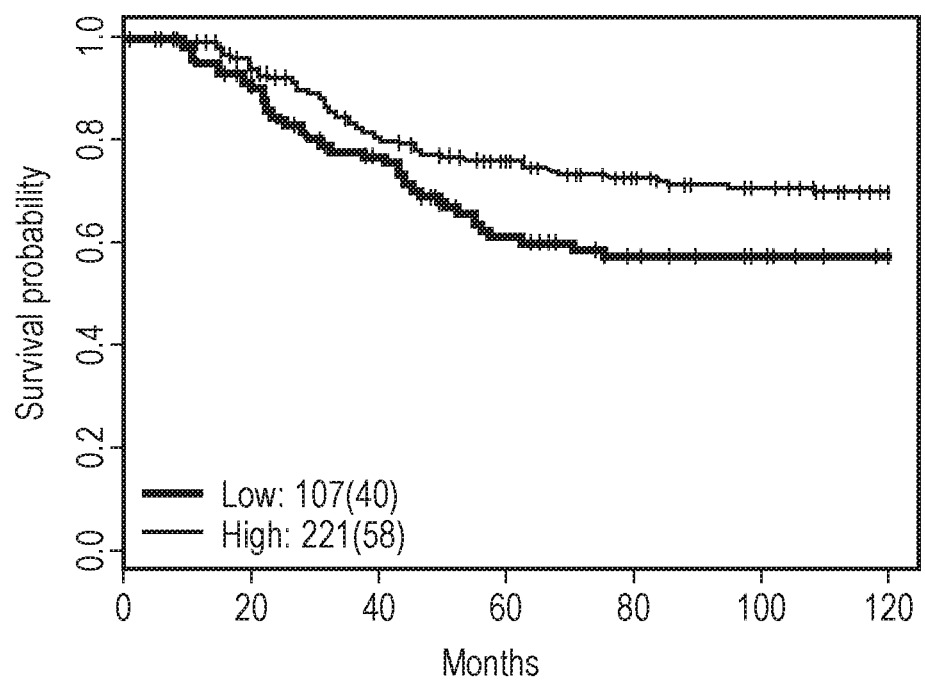

FIG. 15. A. Histogram showing clustering of cells from TNBC tumours into cluster having relatively high CTLA4 expression and cluster having relatively low CTLA4 expression. B. Kaplan-Meier curve illustrating difference in survival between patients having low CLTA4 expression and high CTLA4 expression.

DETAILED DESCRIPTION OF THE INVENTION

Certain aspects and embodiments of the invention will now be illustrated by way of example and with reference to the figures described above.

The inventor has devised a novel way of statistically modelling the spatial heterogeneity of lymphocytes in tumours, which enables determination of a quantitative measurement of immune infiltration (ITLR). ITLR (intra-tumour lymphocyte ratio) is the ratio of intra-tumour lymphocytes to cancer cells in a tumour. This quantitative measurement of immune infiltration (ITLR) has improved predictive power in cancer prognosis compared with previous indicators of immune infiltration. This measurement of immune infiltration was developed based on a study of tumours from triple negative breast cancer (TNBC) patients from the METABRIC dataset, but is more generally useful in and applicable to other breast cancer sub-types and other cancer types. The generalizable nature of ITLR is demonstrated by the data herein showing that ITLR is also a prognostic indicator in ovarian cancer.

Described herein is the first study to statistically identify categories of lymphocytes based on tumour spatial heterogeneity and demonstrate their clinical implications using samples from a large number of patients. This enables a way of modelling spatial heterogeneity in tumours which addresses the need for measuring heterogeneity of lymphocytic infiltration in tumours. The ability to generate reproducible, quantitative scores provides new opportunities for incorporating immune infiltration into staging of cancer (i.e.

grading of tumours), as in the use of immunoscore for colorectal cancer (Galon, 2014).

The present invention provides a method of measuring immune infiltration in tumours. In particular, there is provided a method of determining an objective measurement of immune infiltration in a tumour (ITLR), which measurement is the ratio of intra-tumour lymphocytes to cancer cells.

Accordingly, an aspect of the present invention provides a method of measuring immune infiltration in a tumour, the method comprising:

providing an image of the tumour in which lymphocytes and cancer cells have been identified;
obtaining a lymphocyte-to-cancer measurement for each lymphocyte;
classifying a subset of the lymphocytes as intra-tumour lymphocytes according to their lymphocyte-to-cancer ratio;
quantifying the intra-tumour lymphocytes and the cancer cells in the tumour image;
calculating the intra-tumour lymphocyte ratio (ITLR) as the ratio of intra-tumour lymphocytes to cancer cells, wherein the ITLR is a measurement of immune infiltration in the tumour.

The methods described herein may be performed using a tumour image in which lymphocytes and cancer cells have been identified. The lymphocytes and cancer cells may have been identified by automated image analysis.

The methods described herein may further comprise a step of identifying cancer cells and lymphocytes in a tumour image by automated image analysis. The methods may comprise steps of generating a tumour image and then identifying lymphocytes and cancer cells in the tumour image by automated image analysis.

The step of identifying cancer cells and lymphocytes in a tumour by automated image analysis may be based on the different nuclear morphologies of cancer cells and lymphocytes. This step may be performed on tumour sections, such as whole-tumour section slides. The tumour section may be H&E stained. The types and/or spatial locations of at least about 10,000 cells may be recorded in this step. The types and/or spatial locations of at least about 20,000, at least about 50,000, at least about 90,000, at least 100,000, at least about 110,000, about 10,000 to 150,000, about 50,000 to 120,000, or about 100,000 to 120,000 cells may be recorded in this step. The types and/or spatial locations of, or about 90,000, about 100,000, or about 110,000 cells may be recorded in this step. The cells may be lymphocytes. This step may use any automated image analysis tool capable of identifying lymphocytes and cancer cells. The automated image analysis tool may be the tool disclosed in Yuan et al, 2012.

The image analysis tool disclosed in Yuan et al, 2012, which is hereby incorporated by reference in its entirety, identifies cancer, lymphocytes and stromal cells encompassing fibroblasts and endothelial cells based on their nuclear morphologies in H&E whole-tumour section slides. The main component of this tool is a classifier trained by pathologists over randomly selected tumour regions and validated in 564 breast tumours with 90% accuracy. The image analysis tool described in Yuan et al classifies cells into three categories: cancer, lymphocyte or stromal based on morphological features using a support vector machine.

The image analysis tool described in Yuan et al, 2012 identified cancer cells by their typically large (>10 µm), round nuclei. The stromal class was trained on spindle-shaped stromal cell nuclei (likely to be fibroblasts) and may encompass other stromal cells with similar morphology, such as endothelial cells. The lymphocyte class was trained on immune cells with the distinctive morphology of lymphocytes: small (<8 µm), dark nuclei and not much cytoplasm.

The image analysis tool described in Yuan et al was trained using breast tumour images. Automated image analysis tools, such as those described in Yuan et al 2012, can be trained in cancer types other than breast cancer (including those cancer types and subtypes mentioned herein) in order to identify lymphocytes and cancer cells in the tumours of other cancer types.

Various automated image analysis tools are known in the art. For example the tools described in Failmezger et al (CRImage) particular Janowczyj et al, and Basavanhally et al, which are hereby incorporated by reference in their entirety. Any such tool may be suitable for, or adapted for, use in the methods described herein.

As a result of automated image analysis, the types and spatial locations of a large number of cells are recorded in every tumour image. The automated image analysis may enable the mapping of spatial distributions of all, or essentially all, cancer cells and lymphocytes within a tumour image.

Following a step of identifying the cancer cells and lymphocytes using automated image analysis, the spatial relationships of lymphocytes and cancer cells are analysed.

The methods described herein comprise a step of obtaining a lymphocyte-to-cancer measurement for each lymphocyte. This provides a quantitative measurement of each lymphocyte's proximity to cancer cells and spatial location relative to cancer cells.

Figure 1:
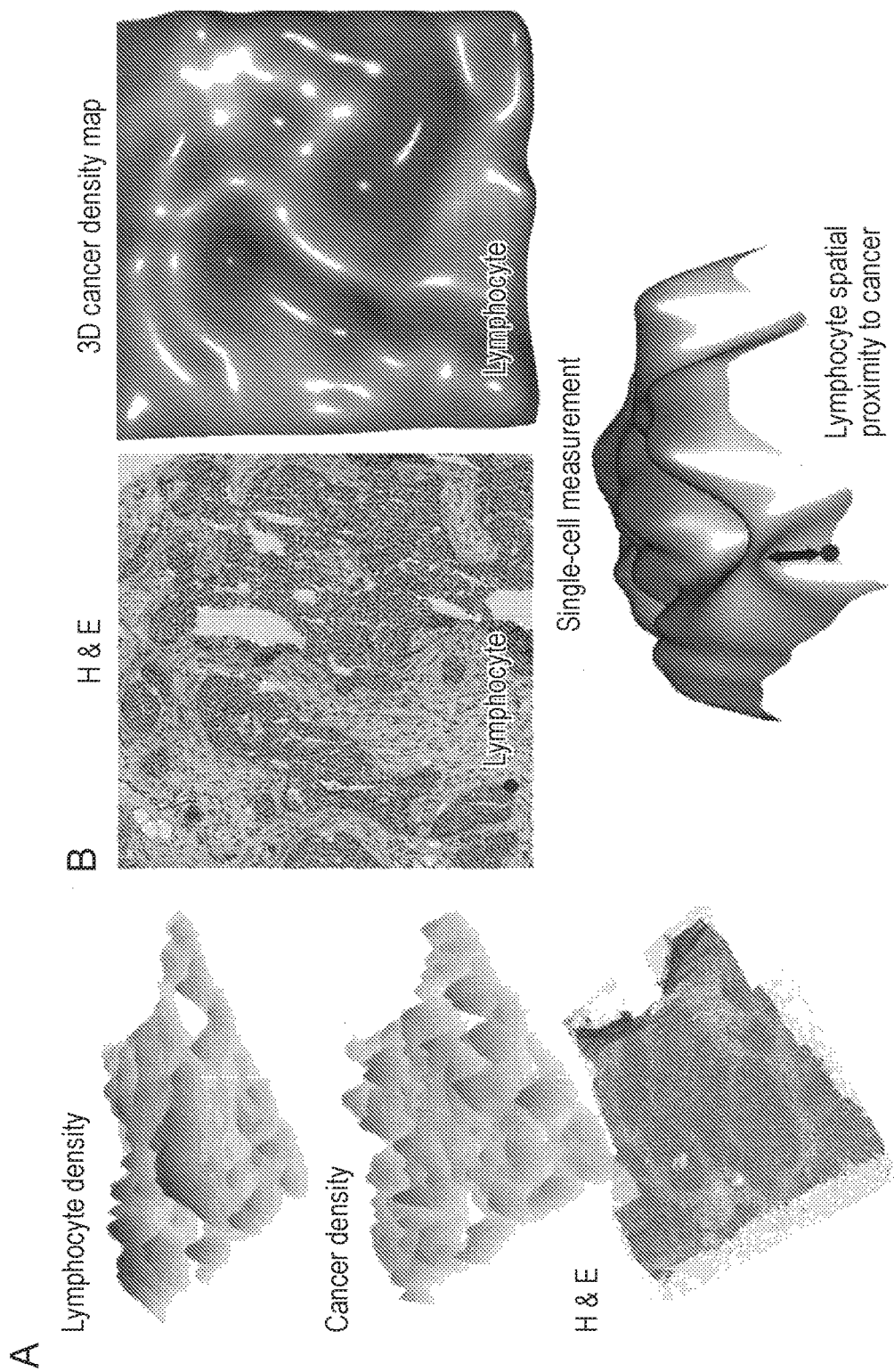
FIG. 1. Intra-tumour heterogeneity of cancer cell and lymphocyte distributions.

The step of obtaining a lymphocyte-to-cancer measurement for each lymphocyte may be carried out using the statistical pipeline exemplified in FIG. 1B. First, to globally profile the spatial distribution of the cancer cells, the cancer cell density is quantified, for example using a kernel estimate (Hastie et al, 2001). Alternatively, a mean shift estimate (Cheng, 1995) or scale space (Witkin, 1983) estimate may be used. This builds a 'cancer landscape' where hills indicate tumour regions densely populated with cancer cells. The height of a hill thus correlates with cancer density (tumour density) at a specific location in the tumour (FIG. 1B). Secondly, for every lymphocyte, its spatial proximity to cancer is directly quantified with the cancer density landscape at its specific location to give a "lymphocyte-to-cancer" measurement for each lymphocyte. Thus a quantitative measurement of the spatial proximity to cancer cells is obtained for each lymphocyte (FIG. 1B).

In the studies described herein (see Experimental), cancer cells and lymphocytes were identified, and then their spatial relationships were quantified using a kernel density method. Then, using unsupervised learning, three categories of lymphocytes (intra-tumour, adjacent-tumour and distal tumour) were identified based on their spatial proximities and spatial positioning relative to cancer cells. These lymphocyte categories are consistent with a pathological quantification scheme that considers intratumoral, adjacent stroma and distant stroma compartments (Mahmoud, 2011). Statistically, these clusters are stable, reported as the optimal clustering solution 97% of the time upon repeated sampling.

Accordingly, the methods described herein may comprise a step of obtaining a lymphocyte-to-cancer measurement for each lymphocyte by using a density estimate, such as a kernel estimate, to model the spatial distribution of the cancer cells. The method then comprises a step of determining the proximity of each lymphocyte to cancer by determining the cancer cell density at the location of each lymphocyte, to give a lymphocyte-to-cancer measurement for each lymphocyte. The lymphocytes are then clustered according to their lymphocyte-to-cancer measurements. An unsupervised learning method, such as Gaussian mixture clustering, may be used to cluster lymphocytes according to their proximity to cancer. The number of clusters may be 2, 3, 4 or more.

In the TNBC study described herein (see Experimental), when lymphocytes were clustered according to their lymphocyte-to-cancer measurements the number of clusters was three (k=3), corresponding to intra-tumour lymphocytes (ITL), adjacent tumour lymphocytes (ATL) and distal tumour lymphocytes (DTL).

In TNBC, lymphocytes having a lymphocyte-to-cancer measurement above the threshold value of 0.10507473 were classified as ITLs, lymphocytes having a lymphocyte-to-cancer measurement below the threshold value of 0.10507473 and above the threshold value of 0.03662728 were classified as ATLs, and lymphocytes having a lymphocyte-to-cancer measurement below the threshold value of 0.03662728 were classified as DTLs. In determining the ITLR, the important distinction is between intra-tumour lymphocytes (ITLs) and non intra-tumour lymphocytes (non-ITLs). Thus in TNBC, lymphocytes having a lymphocyte-to-cancer measurement equal to or above the threshold value of 0.10507473 were classified as ITLs, and the remaining lymphocytes were classified as non-ITLs.

In the ovarian cancer study described herein, when lymphocytes were clustered according to their lymphocyte-to-cancer measurements the number of clusters was two (k=2), corresponding to intra-tumour lymphocytes and non-intra-tumour lymphocytes.

In ovarian cancer, lymphocytes having a lymphocyte-to-cancer measurement above the threshold value of 0.03114299 were classified as ITLs. Lymphocytes having a lymphocyte-to-cancer measurement below this threshold value were classified as non-ITLs.

As an alternative to using cancer density at a lymphocyte location to give a lymphocyte-to-tumour measurement that is indicative of lymphocyte proximity to cancer (i.e. lymphocyte closeness to cancer), the step of obtaining a lymphocyte-to-cancer measurement for each lymphocyte may be carried out based on a distance measure between a lymphocyte and one or more cancer cells, such as the Euclidean distance. The lymphocytes are then clustered according to their lymphocyte-to-cancer measurements, as described above, for example using an unsupervised learning method, such as Gaussian mixture clustering. In this context, where the lymphocyte-to-cancer measurement is indicative of distance from (rather than proximity to) cancer, a lymphocyte may be classified as an ITL if it has lymphocyte-to-cancer measurement below a threshold value.

The methods described herein may comprise classifying lymphocytes as intra-tumour lymphocytes. That is, the methods may comprise classifying a subset of cells identified as lymphocytes in the tumour image as intra-tumour lymphocytes. Classifying lymphocytes may comprise determining whether the lymphocyte-to-cancer measurement is above a certain threshold value. The threshold value, for example in TNBC, may be around 0.1, around 0.105 or around 0.10507473. The threshold value, for example in ovarian cancer, may be around 0.03, around 0.0311, or around 0.03114299.

The methods described herein may comprise determining a threshold value for a lymphocyte-to-cancer measurement, for use in classifying a lymphocyte as an intra-tumour lymphocyte or a non-intra-tumour lymphocyte. For example, where the lymphocyte-to-cancer measurement is indicative of lymphocyte proximity to cancer, the lymphocyte may be classed as an intra-tumour lymphocyte if it has a lymphocyte-to-cancer measurement above the lymphocyte-to-cancer measurement threshold value. Determining a threshold value for a lymphocyte-to-cancer measurement may comprise determining lymphocyte-to-cancer measurements for a population of lymphocytes and clustering the lymphocytes by unsupervised learning, and taking the minimum value of the most cancer proximal cluster (the cluster with the highest measurements) as the threshold value for classifying intra-tumour lymphocytes. A lymphocyte may be classified as an intra-tumour lymphocyte if it has a lymphocyte-to-cancer measurement above (or equal to or above) the threshold value.

Determining the threshold value may further comprise testing the stability of the clustering by sampling the population of lymphocytes, clustering the sampled population of lymphocytes and determining that the cluster solution (k=x where x is the number of clusters) is stable. The number of clusters is stable where k for the sampled population is the same for 200 repeated samples at least 90%, at least 95% or at least 97% of the time.

Furthermore, the inventor has shown significant differences between lymphocyte categories both in spatial distance to the nearest cancer cell and spatial positioning of surrounding cancer cells, supporting their biological relevance. For instance, in the presently disclosed study of tumours from TNBC patients from the METABRIC dataset, an intra-tumour lymphocyte is on average 7 μm away from a cancer cell and 3 μm from the centroid of convex hull region formed by nearby cancer cells. An adjacent-tumour lymphocyte may be also close to the nearest cancer cells but would be further away from the centroid of convex hull region because it is not surrounded by cancer cells. Thus, the new classification approach disclosed herein is based on spatial measures that account for spatial positioning of cancer cells whilst being computationally efficient enough to analyse whole-tumour sections. Compared to a previously reported measure of lymphocyte abundance as a direct output from image analysis (Yuan, 2012), an advantage of this new approach is that it accounts for the spatial heterogeneity of immune infiltration, which is recognised as an important property of immune infiltration (Galon, 2006) but rarely quantitatively analysed.

Following the step of classifying lymphocytes as intra-tumour lymphocytes, the ratio of intra-tumour lymphocytes to cancer cells is calculated. This ratio is the ITLR (the intra-tumour lymphocyte ratio), which is an objective and quantitative measurement of immune infiltration in tumours. The ITLR is the ratio of intra-tumour lymphocytes to cancer cells in the tumour expressed as a decimal fraction. For example, an ITLR of 0.011 represents a 1.1% of intra-tumour lymphocytes to cancer cells i.e. a ratio of 11 intra-tumour lymphocytes to 1000 cancer cells.

The inventor has shown that ITLR is a robust and powerful prognostic indicator in triple negative breast cancer (TNBC), as discussed below, and also in ovarian cancer. Since immune infiltration is implicated in many cancer types, as discussed in more detail below, including breast cancer, ovarian cancer, colorectal cancer (Galon, 2014), melanoma and non-small cell lung cancer, ITLR may also be used as a prognostic indicator in various cancer types.

For prognosis in TNBC, the ITLR cut-off of 0.011 was selected based on tumour images from the METABRIC cohort. Patients whose tumours had an ITLR below the cut-off value of 0.011 had a significantly worse clinical outcome in terms of disease-specific survival compared with patients whose tumours had an ITLR above the cut-off value.

For prognosis in ovarian cancer, the ITLR cut-off of 0.06086 was selected based on tumour images from an unpublished tumour cohort. Patients whose tumours had an ITLR below the cut-off value had a significantly worse clinical outcome in terms of overall survival compared with patients whose tumours had an ITLR above the cut-off value.

An aspect of the present invention provides a method of determining a cut-off value for ITLR for use in determining a prognosis in cancer, wherein an ITLR below the cut-off value indicates a poor prognosis. The method comprises determining the ITLR for a plurality of tumours, wherein each tumour is from a respective cancer patient in a cohort of cancer patients, and selecting a cut-off value for the ITLR wherein patients with an ITLR equal to or below the cut-off value have a significantly worse prognosis compared with patients with an ITLR above the cut-off value.

Accordingly, an aspect of the present invention provides a method of determining an ITLR cut-off value for a cancer type or subtype, for use in providing a prognosis in a cancer patient having that cancer type or subtype, the method comprising:

measuring immune infiltration in a tumour from each member of a cohort of cancer patients having the cancer type or subtype according to the method of claim 1, thereby calculating the ITLR for each tumour; relating the ITLR for each tumour to the clinical outcome of each cancer patient in the cohort of cancer patients; and selecting a cut-off value for ITLR, wherein an ITLR equal to or below the cut-off value is associated with a significantly different clinical outcome in the cohort of cancer patients than an ITLR above the cut-off value.

An ITLR equal to or below the cut-off value may be associated with a significantly worse clinical outcome than an ITLR above the cut-off value. An ITLR equal to or below the cut-off value may be associated with a significantly better clinical outcome than an ITLR above the cut-off value.

The selection of the cut-off value for ITLR serves to dichotomise the continuous range of ITLR values for the tumour images from a patient cohort. The ITLR cut-off value is selected such that there is a significant difference in clinical outcome between patients with an ITLR below the cut-off and patients with an ITLR above the cut-off value. In general, the ITLR cut-off value is selected such that patients having an ITLR below or equal to the cut-off value (i.e. patients having a tumour with an ITLR below or equal to the cut-off value) have a significantly worse prognosis than patients having an ITLR that is above the cut-off value (i.e. patients having a tumour with an ITLR equal to or above the cut-off value).

In the context of the present invention a significant difference in prognosis refers to a clinical outcome that is significantly different according to the Log rank test. Preferably $p<0.0500$, $p<0.0250$, $p<0.0100$, $p<0.0090$, $p<0.0065$, $p<0.0010$, or $p<0.0001$ according to the log rank test.

Selection of the ITLR cut-off value may comprise identifying an ITLR value wherein about 20% to 80% of the patient cohort has an ITLR below that value. Selection of the ITLR cut-off value may comprise identifying an ITLR value wherein about 20% to 80% of the patient cohort has an ITLR below that value and wherein patients having an ITLR below the cut-off value have a significantly worse prognosis than patients having an ITLR that is above the cut-off value.

The clinical outcome may be disease-specific survival, disease free survival, overall survival, relapse-free survival, progression-free survival, survival rate or survival time. The clinical outcome may be disease-specific survival. Disease-specific survival may be defined with time as maximum 5 years or 10 years from diagnosis and event as death due to cancer (the 5 year disease specific survival and 10 year disease specific survival respectively). Overall survival may be defined with time as maximum 5 years or 10 years from diagnosis and event as death due to any cause. Relapse-free survival may be defined with time as maximum 10 years from diagnosis and event as tumour relapse. A poor prognosis refers to a prediction of a poor clinical outcome, whereas a positive prognosis refers to a prediction of a positive clinical outcome.

The methods described herein may use a cohort of cancer patients from The Cancer Genome Atlas (TOGA) as the "discovery" cohort. This dataset, with its H&E and matched molecular profiling data will be an extremely useful cohort to validate the utility of ITLR and to select and refine ITLR cut-off values for use in prognostic and/or therapeutic methods. TCGA has chosen cancers for study based on criteria that include poor prognosis and overall public health impact and the availability of human tumour and matched-normal tissue samples that meet TCGA standards for patient consent quality and quantity.

The experiments disclosed herein show the utility of ITLR in TNBC and in ovarian cancer. ITLR is a generalizable measure for ITLs and will therefore be useful as a measure of immune infiltration in other cancer types I subtypes, especially given that manual assessment of ITLS has reported value in many cancer types I subtypes.

As already mentioned above, immune infiltration is implicated in many cancer types, including breast cancer, ovarian cancer, colorectal cancer, melanoma and non-small cell lung cancer, ITLR may also be used as a prognostic indicator in various cancer types.

Immune infiltration is implicated in many cancers including breast cancer (including breast ductal carcinoma breast and breast lobular carcinoma) (Dieci 2014; Loi S 2013; Kruger J M 2013; Liu S, 2012; Ascierto M L 2012, Rody A, 2011; Mahmoud S M A, 2011; Denkert C, 2010; Ueno T, 2000) central nervous system cancer (including glioblastoma multiforme and lower grade glioma) (Kmiecik J, 2013; Yang I, 2010; McNamara M G, 2014; Crane C A, 2014; Bambury R M; Alexiou G A, 2013; Vauleon E, 2013) endocrine cancer (including adrenocortical carcinoma, papillary thyroid carcinoma, paraganglioma & pheochromocytoma) (Papewalis C; Huang C T; Mukherji B) gastrointestinal cancer (including Cholangiocarcinoma, Colorectal Adenocarcinoma, Liver Hepatocellular Carcinoma, Pancreatic Ductal Adenocarcinoma, Stomach-Esophageal Cancer) (Kono K, 20116; Wu G; Gao Q; Hiraoka N) gynecologic cancer (including Cervical Cancer (Zhang Y, 2014; Ancuta E, 2009), Ovarian Serous Cystadenocarcinoma (Townsend K N, 2013; Milne K, 2009; Clarke B, 2009), Uterine Carcinosarcoma, Uterine Corpus Endometrial Carcinoma) (Ohno S, 2004) head and neck cancer (including Head and Neck Squamous Cell Carcinoma, Uveal Melanoma) (Spanos W C, 2009; Pretscher D, 2009) hematologic cancer (including Acute Myeloid Leukemia, thymoma, lymphoma) (Yong A S, 2011; Dave S S, 2004;) skin cancer (including Cutaneous Melanoma) (Tjin E P, 2014; Erdag G, 2012; Bystryn J C, 1992; Halliday G, 1995) soft tissue cancer (including Sarcoma) (Kim J R, 2016; Sorbye S W 2011; Fiorelli V, 1998) thoracic cancer (including Lung Adenocarcinoma, Lung Squamous Cell Carcinoma, Mesothelioma) (Suzuki K, 2013; Welsh T J, 2005; Villegas F R, 2002; Hegmans J P, 2006; Dieu-Nosjean M C) urologic cancer (including Chromophobe Renal Cell Carcinoma, Clear Cell Kidney Carcinoma, Papillary Kidney Carcinoma, Prostate Adenocarcinoma, Testicular Germ Cell Cancer, Urothelial Bladder Carcinoma) (Davidsson S, 2013; Thompson R H, 2007; Webster W S, 2006; Gannon P O, 2009; Sjodahl G, 2014).

The methods of the present invention may be applied in any of the cancer types or subtypes mentioned above.

ITLR is an objective quantitative indicator of lymphocytic infiltration in tumours. The inventor has shown the importance of using such a quantitative measurement of lymphocytic infiltration in predicting clinical outcome in cancer.

ITLR is a new spatial and quantitative measure of intra-tumour lymphocytes (ITLs). This measure is a consistent, stable and independent predictor of disease-specific survival across two independent cohorts of 181 TNBC patients in total. This measurement may use a cut-off of 0.011 (1.1% of intra-tumour lymphocytes to cancer cells) that dichotomises the ITLR score. The 20% of TNBC patients with ITLR scores lower than this cut-off have significantly worse disease-specific survival than patients with higher scores, and this association is independent of standard clinical parameters. Taken together, these data support the utility of ITLR as a prognostic biomarker for cancer, including TNBC. Accordingly, disclosed herein is an objective and fully automated scoring system for the standardised assessment of immune infiltration that can be used in the context of clinical trials and subsequently aid the treatment decision making process.

Accordingly, an aspect of the present invention may further comprise using ITLR as a prognostic biomarker. The method may comprise measuring the ITLR of a tumour from a cancer patient and using the ITLR to determine a prognosis for the patient. The method may comprise determining the ITLR in a tumour from a cancer patient and using the ITLR to determine a prognosis for the patient, wherein an ITLR below a predetermined cut-off value indicates a poor prognosis. The method may comprise determining the ITLR in a tumour from a cancer patient and using the ITLR to determine a prognosis for the patient, wherein an ITLR above a predetermined cut-off value indicates a poor prognosis.

In particular, an aspect of the present invention provides a method of providing a prognosis in a cancer patient, the method comprising:
measuring immune infiltration in a tumour from the cancer patient according to a method described herein, thereby calculating the ITLR for the tumour,
wherein an ITLR below a predetermined ITLR cut-off value indicates a poor prognosis.

An aspect of the present invention provides a method of providing a prognosis in a cancer patient, the method comprising:
providing an image of the tumour in which lymphocytes and cancer cells have been identified;
obtaining a lymphocyte-to-cancer measurement for each lymphocyte;
classifying a subset of the lymphocytes as intra-tumour lymphocytes according to their lymphocyte-to-cancer ratio;
quantifying the intra-tumour lymphocytes and the cancer cells in the tumour image;
calculating the intra-tumour lymphocyte ratio (ITLR) as the ratio of intra-tumour lymphocytes to cancer cells, wherein the ITLR is a measurement of immune infiltration in the cancer patient's tumour
and wherein an ITLR below a predetermined ITLR cut-off value indicates a poor prognosis.

The inventor has shown that ITLR is an independent predictor of clinical outcome in cancer. That is, the ITLR is predictive of clinical outcome without using any other biomarker (such as a gene expression biomarker) or clinical indicator (such as tumour size). For example, the inventor has shown that ITLR is an independent predictor of clinical outcome in triple negative breast cancer (TNBC) and in ovarian cancer. For example in the studies described herein there was no correlation between ITLR and tumour size, node status and TP53 mutation status (FIG. 4D), and so ITLR is independent of such clinical indicators and biomarkers. Preferably, if the ITLR is below a predetermined cut-off value (or equal to or below a predetermined cut-off value), this indicates a poor prognosis (i.e. a poor clinical outcome). A poor prognosis, or poor clinical outcome, may be poor disease-specific survival.

In the present context, an ITLR below a predetermined cut-off value may be referred to as a low ITLR, or ITLR-low. Conversely an ITLR above a predetermined cut-off value may be referred to as a high ITLR, or ILTR-high. A predetermined cut-off value for an ITLR may simply be referred to herein as an ITLR cut-off value.

A poor prognosis means that the patient has a worse prognosis than a patient having an ITLR value above the cut-off ITLR value. For example a poor prognosis may mean that the patient is expected to have shorter disease-specific survival time than a patient having an ITLR value above the cut-off ITLR value. A poor prognosis may mean that the patient has a worse prognosis than a patient having an ITLR value above the cut-off ITLR value. The hazard ratio between the patient group having an ITLR below the ITLR cut-off value and the group having an ITLR above the ITLR cut-off value may be from around 0.2 to around 0.4, may be from around 0.25 to around 0.36, may be around 0.25 or may be around 0.36. This means that a patient with ITLR high than the cut-off value is 0.25-0.36 times less likely to die from breast cancer than a patient with ITLR lower than the cut-off value. A poor prognosis may mean that a patient has a survival probability of around 50%, or around 49%, five years from diagnosis, or ten years from diagnosis. A good prognosis may mean that a patient has a survival probability of around 80% five years from diagnosis or ten years from diagnosis.

A predetermined ITLR cut-off value may be about 0.011, or about 0.061. The cut-off value may be from about 0.005 to about 0.070, from about 0.010 to about 0.070, from about 0.010 to about 0.012, or from about 0.050 to about 0.070. A predetermined ITLR cut-off value for TNBC may be about 0.011, and for ovarian cancer may be about 0.061.

ITLR was tested in two independent cohorts of TNBC and shown to be predictive of disease-specific survival. When TNBC Cohort 1 was used as the discovery cohort an ITLR cut-off value of 0.011 was selected (that is, patients having an ITLR below this value showed significantly worse disease-specific survival than patients having an ITLR above this value), and in Cohort 2 an ITLR of below 0.011 was associated with significantly worse disease-specific survival than patients with an ITLR above 0.011 (Log-rank test p=0.0063, FIG. 4F). Similarly, when TNBC Cohort 2 was used as the discovery cohort an ITLR cut-off of 0.011 was selected, and in Cohort 1 an ITLR of below 0.011 was associated with significantly worse disease-specific survival than patients with an ITLR above 0.011 (p=0.0037, FIG. 4F).

The prognostic power of ITLR compares favourably with that of previously published prognostic indicators. ITLR is a more powerful prognostic indicator than the previously published indicator "Lym" (a tumour section image-analysis based indicator of lymphocyte abundance; Yuan et al., 2012) and several published gene signature-based indicators (Calabro et al., Ascierto et al., Rody et al, Ma et al., Gu-Trantien et al).

The same cut-off selection approach used to select the ITLR cut-off was used to test the prognostic power of "Lym" (an image-based measure of lymphocyte abundance in tumour sections) and several gene expression signatures in TNBC and in ovarian cancer. None of these other prognostic indicators consistently correlated with prognosis in both Cohort 1 and Cohort 2. By contrast, ITLR consistently stratified patients into two groups of different clinical outcome. (See FIG. 4, FIG. 5, FIG. 14)

Compared to published gene expression signatures, ITLR was also the only signature to show significant correlation with disease-specific survival in multivariate Cox proportional hazards model together with standard clinical parameters of nodal status and tumour size in both cohorts, whichever cohort was used as the discovery cohort (Tables 1 to 3).

Using samples from both TNBC cohorts, ITLR has a log-rank p-value of $2.1 \times 10^{-4}$ and HR 0.32 (0.17-0.58). To test the robustness of the Cox model in determining the prognostic value of ITLR, bootstrap analysis was used in randomly perturbed data and the univariate and multivariate regression analysis was repeated 1,000 times. In 95.6% and 94.7% of instances, ITLR remained significantly associated with prognosis in univariate and multivariate analysis, respectively. Taken together, these data support the stability and robustness of ITLR as an independent prognostic biomarker in TNBC.

ITLR measures the ratio of intra-tumour lymphocytes to cancer cells, thus is different to the pathological assessment approach described in previous studies (Denkert, 2010; Loi, 2013; Deici, 2014), where the proportion of tumour nests that were infiltrated by lymphocytes were reported. These previous studies agree with the results described herein, because they show that tumour-infiltration lymphocytes are significantly correlated with favorable outcome in TNBC. These previous approaches, like the experiments reported herein, were based on H&E stained pathological samples and therefore support the position that measures of lymphocytic infiltration can be useful tool to aid clinical decisions in TNBC.

Unlike the methods of the invention (which are based on automated image analysis), the previous methods are based on assessment of tumour sections by pathologists (Denkert, 2010; Loi, 2013; Deici, 2014; Salgado, 2014). The previous methods looking at proportions of tumour nests infiltrated by lymphocytes are thus subjective, and therefore subject to bias and variability, and generate results relatively slowly with higher associated costs, the previous methods are thus unsuitable for very large scale analyses.

The approach taken in the present invention, of identifying lymphocyte subtypes by image analysis, contrasts with previous approaches to assessing immune infiltration in tumours. Previous approaches using image analysis (Yuan, 2012) have only taken account of abundance of lymphocytes in tumours, whereas approaches that attempt to take account of spatial locations of lymphocytes (Denkert, 2010; Loi, 2013; Deici, 2014) have used only manual (pathologist) based processes and have relied on qualitative and subjective assessment of cancer cell constellations and their relationships with lymphocytes (the presence of cancer cell "nest" and the proportion of such nests containing lymphocytes). By contrast the present inventor has taken the approach of using image analysis techniques to identify lymphocyte subtypes within tumours and use the relative abundance of a subtype of lymphocytes (ITLs) to cancer cells as an objective quantitative measure of immune infiltration. The image analysis techniques of the present invention are preferably automated or computer-implemented techniques, thereby facilitating analysis of large numbers (in the order of 100,000—preferably at least 10,000, at least 50,000, or at least 100,000) of lymphocytes per tumour image and permitting large-scale analyses of cohorts of patients having various types and subtypes of cancer.

Unlike the methods of the invention, which robustly predict clinical outcome, pathological scores of immune infiltration (including pathological assessment of lymphocytic infiltration) were not significantly correlated with prognosis (FIG. 13). The pathological scores tested included PAM50 (Perou et al., 2000), pathological assessment of lymphocytic infiltration, tumour size, and grade. Pathological assessment of lymphocytic infiltration for the purposes of this study was scored as absent, mild, or severe: Absent if there were no lymphocytes, mild if there was a light scattering of lymphocytes, and severe if there was a prominent lymphocytic infiltrate.

The prognostic methods of the invention, which are based on an objective indicator of immune cell infiltration obtained by an automated method, have several advantages over previous prognostic methods for use in cancer. As explained above, ITLR has greater predictive power than several previously known cancer biomarkers and prognostic indicators and greater predictive power than pathological scores of immune infiltration. Because ITLR is determined using automated methods it provides an objective measurement of immune cell infiltration in cancer (i.e. not subject to subjective bias or human error, which causes variability in results), it requires no pathologist scoring (and therefore no pathologist training or following of new guidelines) and is relatively low cost and quick to obtain, which makes it suited to large scale analysis of cancer data. Although detection of gene-expression signature based signatures may be automated, ITLR, because it can conveniently be based on tumour images such as H&E stained sections (copies of which are easily and cheaply shared and stored long-term), is lower cost and more convenient biomarker than gene expression signature-based biomarkers (which require access to preserved biological samples). The image-based ITLR outperforms several gene expression-based signatures using the optimal cut-off selection method. In addition, considering the cost of microarray data acquisition, the ITLR-based approaches described herein open a new avenue for large-scale analysis on readily available pathological samples.

TABLE 1

Univariate and multivariate Cox regression results for ITLR and other signatures in two TNBC cohorts.

| | | Cohort 1 | | | Cohort 2 | | |
| --- | --- | --- | --- | --- | --- | --- | --- |
| | | HR(CI) | p | Conc | p | HR(CI) | Conc |
| ITL | Uni- | 0.36(0.17-0.77) | 0.0063 | 0.601 | 0.25(0.09-0.69) | 0.0036 | 0.659 |
| | ITL | 0.32(0.15-0.7) | 0.0042 | 0.668 | 0.15(0.05-0.43) | 0.00051 | 0.76 |
| | Node | 0.63(0.29-1.4) | 0.26 | | 4.93(1.61-15.08) | 0.0052 | |
| | Size | 2.62(1.27-5.41) | 0.0092 | | 2.07(0.9-4.74) | 0.087 | |

TABLE 1-continued

Univariate and multivariate Cox regression results for ITLR and other signatures in two TNBC cohorts.

|  |  | Cohort 1 | | | Cohort 2 | | |
|---|---|---|---|---|---|---|---|
|  |  | HR(CI) | p | Conc | p | HR(CI) | Conc |
| Lym | Uni- | 0.47(0.21-1.02) | 0.051 | 0.574 | 0.41(0.12-1.43) | 0.15 | 0.575 |
|  | Lym | 0.48(0.22-1.05) | 0.066 | 0.656 | 0.23(0.05-1.02) | 0.053 | 0.735 |
|  | Node | 0.69(0.32-1.5) | 0.35 |  | 4.65(1.46-14.81) | 0.0092 |  |
|  | Size | 2.35(1.16-4.77) | 0.018 |  | 1.66(0.65-4.25) | 0.29 |  |
| Calabro | Uni- | 0.25(0.12-0.52) | 5.2 × 10⁻⁵ | 0.66 | 0.5(0.18-1.39) | 0.18 | 0.587 |
|  | Calabro | 0.27(0.13-0.56) | 3.8 × 10⁻⁴ | 0.703 | 0.41(0.14-1.19) | 0.1 | 0.744 |
|  | Node | 0.75(0.35-1.6) | 0.45 |  | 4.57(1.45-14.37) | 0.0093 |  |
|  | Size | 2.26(1.07-4.76) | 0.032 |  | 1.91(0.82-4.46) | 0.13 |  |
| Ascierto | Uni- | 0.34(0.15-0.77) | 0.0066 | 0.621 | 1.23(0.4-3.83) | 0.72 | 0.51 |
|  | Ascierto | 0.39(0.17-0.88) | 0.024 | 0.671 | 1.18(0.37-3.72) | 0.78 | 0.735 |
|  | Node | 0.85(0.39-1.84) | 0.68 |  | 3.6(1.21-10.7) | 0.021 |  |
|  | Size | 2.06(1.02-4.16) | 0.044 |  | 2.16(0.86-5.45) | 0.1 |  |
| IL8 | Uni- | 3.09(1.46-6.51) | 0.0018 | 0.615 | 0(0-Inf) | 0.0099 | 0.645 |
|  | IL8 | 2.79(1.32-5.92) | 0.0073 | 0.679 | 0(0-Inf) | 1 | 0.808 |
|  | Node | 0.81(0.37-1.75) | 0.59 |  | 3.14(1.06-9.34) | 0.039 |  |
|  | Size | 2.23(1.08-4.63) | 0.031 |  | 1.75(0.71-4.28) | 0.22 |  |
| CXCL13 | Uni- | 0.21(0.1-0.46) | 1.5 × 10⁻⁶ | 0.69 | 0.76(0.28-2.1) | 0.6 | 0.545 |
|  | CXCL13 | 0.24(0.11-0.54) | 4.5 × 10⁻⁴ | 0.721 | 0.83(0.29-2.37) | 0.73 | 0.739 |
|  | Node | 0.69(0.32-1.49) | 0.35 |  | 3.61(1.22-10.71) | 0.021 |  |
|  | Size | 1.71(0.83-3.55) | 0.15 |  | 2.12(0.86-5.22) | 0.1 |  |

Shaded sections show results from multivariate regression. Uni-: Univariate Cox regression; HR: Hazard Ratio; CI: lower and higher 95% Confidence Interval; Conc: Concordance; 0(0-Inf): where the Cox model failed to converge. P-values that pass the significant threshold of 0.05 are shown in bold.

TABLE 2

Univariate and multivariate Cox regression results for ITLR and other eight signatures using the optimal cut-offs selected in Cohort 1 and validated in Cohort 2.

|  | Cohort1 | | | Cohort2 | | |
|---|---|---|---|---|---|---|
|  | HR(CI) | p-value | conc | HR(CI) | p-value | conc |
| Uni-ITL | 0.36(0.17-0.77) | 0.0063 | 0.601 | 0.25(0.09-0.69) | 0.0036 | 0.659 |
| Multi-ITL | 0.32(0.15-0.7) | 0.0042 | 0.668 | 0.15(0.05-0.43) | 0.00051 | 0.76 |
| Multi-node | 0.63(0.29-1.4) | 0.26 |  | 4.93(1.61-15.08) | 0.0052 |  |
| Multi-size | 2.62(1.27-5.41) | 0.0092 |  | 2.07(0.9-4.74) | 0.087 |  |
| Uni-Lym | 0.47(0.21-1.02) | 0.051 | 0.574 | 0.41(0.12-1.43) | 0.15 | 0.575 |
| Multi-Lym | 0.48(0.22-1.05) | 0.066 | 0.656 | 0.23(0.05-1.02) | 0.053 | 0.735 |
| Multi-node | 0.69(0.32-1.5) | 0.35 |  | 4.65(1.46-14.81) | 0.0092 |  |
| Multi-size | 2.35(1.16-4.77) | 0.018 |  | 1.66(0.65-4.25) | 0.29 |  |
| Uni-Calabro | 0.25(0.12-0.52) | 5.20E−05 | 0.66 | 0.5(0.18-1.39) | 0.18 | 0.587 |
| Multi-Calabro | 0.27(0.13-0.56) | 0.00038 | 0.703 | 0.41(0.14-1.19) | 0.1 | 0.744 |
| Multi-node | 0.75(0.35-1.6) | 0.45 |  | 4.57(1.45-14.37) | 0.0093 |  |
| Multi-size | 2.26(1.07-4.76) | 0.032 |  | 1.91(0.82-4.46) | 0.13 |  |
| Uni-IL8 | 3.09(1.46-6.51) | 0.0018 | 0.615 | 0(0-Inf) | 0.0099 | 0.645 |
| Multi-IL8 | 2.79(1.32-5.92) | 0.0073 | 0.679 | 0(0-Inf) | 1 | 0.808 |
| Multi-node | 0.81(0.37-1.75) | 0.59 |  | 3.14(1.06-9.34) | 0.039 |  |
| Multi-size | 2.23(1.08-4.63) | 0.031 |  | 1.75(0.71-4.28) | 0.22 |  |
| Uni-Bcell | 0.6(0.25-1.48) | 0.26 | 0.557 | 0.51(0.12-2.27) | 0.37 | 0.539 |
| Multi-Bcell | 0.57(0.23-1.4) | 0.22 | 0.655 | 0.48(0.11-2.17) | 0.34 | 0.747 |
| Multi-node | 0.7(0.32-1.5) | 0.35 |  | 3.77(1.27-11.2) | 0.017 |  |
| Multi-size | 2.38(1.19-4.76) | 0.014 |  | 2.07(0.86-5) | 0.11 |  |
| Uni-Bcell.IL8 | 0.52(0.24-1.11) | 0.086 | 0.581 | 1.1(0.41-2.95) | 0.86 | 0.482 |
| Multi-Bcell.IL8 | 0.53(0.25-1.12) | 0.097 | 0.648 | 1.22(0.42-3.53) | 0.71 | 0.743 |
| Multi-node | 0.74(0.34-1.6) | 0.44 |  | 3.76(1.24-11.41) | 0.02 |  |
| Multi-size | 2.36(1.17-4.76) | 0.016 |  | 2.21(0.88-5.54) | 0.091 |  |
| Uni-Ascierto | 0.34(0.15-0.77) | 0.0066 | 0.621 | 1.23(0.4-3.83) | 0.72 | 0.51 |
| Multi-Ascierto | 0.39(0.17-0.88) | 0.024 | 0.671 | 1.18(0.37-3.72) | 0.78 | 0.735 |
| Multi-node | 0.85(0.39-1.84) | 0.68 |  | 3.6(1.21-10.7) | 0.021 |  |
| Multi-size | 2.06(1.02-4.16) | 0.044 |  | 2.16(0.86-5.45) | 0.1 |  |
| Uni-CXCR3 | 0.3(0.14-0.64) | 9.00E−04 | 0.618 | 0.82(0.3-2.25) | 0.7 | 0.535 |
| Multi-CXCR3 | 0.31(0.15-0.66) | 0.0026 | 0.683 | 0.79(0.25-2.45) | 0.68 | 0.73 |
| Multi-node | 0.86(0.39-1.87) | 0.7 |  | 3.81(1.24-11.72) | 0.02 |  |
| Multi-size | 2.24(1.13-4.44) | 0.02 |  | 2.07(0.82-5.18) | 0.12 |  |
| Uni-CXCL13 | 0.21(0.1-0.46) | 1.50E−05 | 0.69 | 0.76(0.28-2.1) | 0.6 | 0.545 |
| Multi-CXCL13 | 0.24(0.11-0.54) | 0.00045 | 0.721 | 0.83(0.29-2.37) | 0.73 | 0.739 |
| Multi-node | 0.69(0.32-1.49) | 0.35 |  | 3.61(1.22-10.71) | 0.021 |  |
| Multi-size | 1.71(0.83-3.55) | 0.15 |  | 2.12(0.86-5.22) | 0.1 |  |

Uni-: Univariate Cox regression; Multi-: Multivariate Cox regression; HR: Hazard Ratio; CI: lower and higher 95% Confidence Interval; Conc: Concordance; Inf: Cox model failed to converge.

TABLE 3

Univariate and multivariate Cox regression results for ITLR and other eight signatures using the optimal cut-offs selected in Cohort 2 and validated in Cohort 1.

|  | Cohort1 | | | Cohort2 | | |
| --- | --- | --- | --- | --- | --- | --- |
|  | HR(CI) | p-value | conc | HR(CI) | p-value | conc |
| Uni-ITL | 0.45(0.21-0.96) | 0.033 | 0.587 | 0.26(0.1-0.71) | 0.0048 | 0.656 |
| Multi-ITL | 0.38(0.17-0.84) | 0.016 | 0.654 | 0.16(0.05-0.48) | 0.001 | 0.76 |
| Multi-node | 0.62(0.28-1.37) | 0.23 |  | 4.64(1.52-14.15) | 0.007 |  |
| Multi-size | 2.62(1.27-5.39) | 0.0088 |  | 2.07(0.89-4.83) | 0.091 |  |
| Uni-Lym | 0.91(0.43-1.91) | 0.8 | 0.524 | 0.35(0.13-0.98) | 0.038 | 0.63 |
| Multi-Lym | 0.92(0.43-1.95) | 0.82 | 0.627 | 0.29(0.1-0.85) | 0.024 | 0.778 |
| Multi-node | 0.72(0.33-1.58) | 0.41 |  | 3.82(1.29-11.38) | 0.016 |  |
| Multi-size | 2.33(1.18-4.64) | 0.015 |  | 1.85(0.73-4.73) | 0.2 |  |
| Uni-Calabro | 0.53(0.24-1.2) | 0.12 | 0.578 | 0(0-Inf) | 0.04 | 0.608 |
| Multi-Calabro | 0.56(0.24-1.28) | 0.17 | 0.667 | 0(0-Inf) | 1 | 0.799 |
| Multi-node | 0.67(0.31-1.46) | 0.31 |  | 4.12(1.39-12.23) | 0.011 |  |
| Multi-size | 2.17(1.11-4.24) | 0.023 |  | 1.91(0.8-4.55) | 0.14 |  |
| Uni-IL8 | 1.76(0.86-3.6) | 0.12 | 0.575 | 0.18(0.05-0.63) | 0.0026 | 0.692 |
| Multi-IL8 | 1.74(0.84-3.59) | 0.14 | 0.65 | 0.21(0.06-0.77) | 0.018 | 0.795 |
| Multi-node | 0.8(0.37-1.73) | 0.57 |  | 3.76(1.25-11.34) | 0.019 |  |
| Multi-size | 2.29(1.17-4.51) | 0.016 |  | 1.87(0.68-5.17) | 0.23 |  |
| Uni-Bcell | 0.74(0.35-1.59) | 0.44 | 0.541 | 0.41(0.09-1.82) | 0.23 | 0.557 |
| Multi-Bcell | 0.75(0.35-1.6) | 0.45 | 0.63 | 0.33(0.07-1.5) | 0.15 | 0.763 |
| Multi-node | 0.72(0.33-1.55) | 0.39 |  | 4.24(1.41-12.76) | 0.01 |  |
| Multi-size | 2.33(1.17-4.61) | 0.016 |  | 1.94(0.81-4.67) | 0.14 |  |
| Uni-Bcell.IL8 | 0.82(0.35-1.92) | 0.65 | 0.511 | 0.45(0.16-1.31) | 0.13 | 0.599 |
| Multi-Bcell.IL8 | 0.75(0.32-1.76) | 0.51 | 0.629 | 0.59(0.2-1.76) | 0.34 | 0.753 |
| Multi-node | 0.73(0.34-1.59) | 0.43 |  | 3.28(1.08-9.94) | 0.036 |  |
| Multi-size | 2.4(1.2-4.83) | 0.014 |  | 2.18(0.85-5.6) | 0.11 |  |
| Uni-Ascierto | 0.83(0.39-1.78) | 0.64 | 0.52 | 2.26(0.82-6.23) | 0.11 | 0.63 |
| Multi-Ascierto | 1(0.46-2.16) | 0.99 | 0.619 | 2.6(0.87-7.82) | 0.089 | 0.773 |
| Multi-node | 0.73(0.34-1.59) | 0.43 |  | 3.22(1.08-9.61) | 0.036 |  |
| Multi-size | 2.33(1.16-4.66) | 0.017 |  | 2.46(0.91-6.62) | 0.075 |  |
| Uni-CXCR3 | 0.56(0.24-1.29) | 0.17 | 0.569 | 0(0-Inf) | 0.029 | 0.618 |
| Multi-CXCR3 | 0.62(0.26-1.48) | 0.28 | 0.658 | 0(0-Inf) | 1 | 0.805 |
| Multi-node | 0.68(0.32-1.49) | 0.34 |  | 4.17(1.41-12.38) | 0.01 |  |
| Multi-size | 2.16(1.09-4.28) | 0.028 |  | 1.89(0.8-4.46) | 0.15 |  |
| Uni-CXCL13 | 0.35(0.17-0.75) | 0.0043 | 0.605 | 2.21(0.71-6.86) | 0.16 | 0.595 |
| Multi-CXCL13 | 0.38(0.18-0.79) | 0.01 | 0.663 | 3.38(0.92-12.45) | 0.067 | 0.773 |
| Multi-node | 0.69(0.32-1.49) | 0.35 |  | 3.71(1.24-11.1) | 0.019 |  |
| Multi-size | 2.29(1.11-4.72) | 0.026 |  | 2.71(0.94-7.8) | 0.064 |  |

Uni-: Univariate Cox regression; Multi-; Multivariate Cox regression; HR: Hazard Ratio; CI: lower and higher 95% Confidence Interval; Conc: Concordance.

ITLR as an unbiased assessment of immune infiltration can facilitate the discovery of molecular correlates with this clinically important phenomenon. While the expression of many immune-related genes in tumours was significantly associated with ITLR, it is unclear whether these genes are expressed on cancer cells or lymphocytes. This is because the microarray data were obtained using whole-tumour materials without micro-dissection.

The data herein show that the RNA expression of cytotoxic T-lymphocyte-associated protein 4 (CTLA4), a receptor of the immunoglobulin family and the target of ipilimumab, was significantly associated with ITLR as well as longer disease specific survival in TNBC. This is consistent with the recent observation in non-small cell lung cancers that over-expression of CTLA4 is associated with reduced death rate (Salvi, 2012). CTLA4 is expressed in tumour cells in different cancer types (Contardi, 2005). In breast cancer it is expressed in both tumour cells and T cells, and an inverse correlation between CTLA4 expression and clinical outcome (i.e. high CTLA4 expression associated with poor clinical outcome) has been previously reported in 60 patients with different breast cancer subtypes (Mao, 2010), which is in contrast with the data herein from TNBC (see below), and which thus highlights the novel molecular insights into cancer yielded by ITLR. A recent study showed that in situ mRNA expression of another receptor of the immunoglobulin superfamily, PDL1, is associated with increased immune infiltration and favourable recurrence free survival across different breast cancer subtypes (Schalper, 2014).

Taken together, the data herein support the potential of CTLA4-targeted therapies in TNBC. CTLA4 is a negative regulator of T cells, and therefore its expression reduces T cell-mediated killing of cancer cells. The data herein show a positive association between CLTA4 expression and ITLR, consistent with ITL expression of CTLA4. The expression of CTLA4 in ITLs may explain why in many tumours cancer cells were not eliminated even in the presence of high numbers of ITLs. The use of CTLA4 antagonists to inhibit immune tolerance to cancer and to activate ITLs may be an effective treatment strategy for TNBC.

Unsupervised clustering with Gaussian Mixture modelling for CTLA4 expression in all 1,980 METABRIC tumours revealed two clusters, one with high and one with low level of expression of CTLA4 (FIG. 15 A). Using this clustering definition for TNBC tumours we found that TNBC patients with higher level of CTLA4 expression have significantly better disease-specific survival than patients with lower level of CTLA4 expression (p=0.018, HR=0.61, CI=0.41-0.92, FIG. 15 B).

The gene module analysis also revealed several tightly connected, functionally related modules. For example, one module contains APOBEC3G (Apolipoprotein B MRNA Editing Enzyme, Catalytic Polypeptide-Like 3G), which is known to play important roles in adaptive and innate immunity and has been investigated extensively in viral infection (Mangeat, 2003) but its role in breast cancer has not been investigated in detail. It is a member of the apolipoprotein B mRNA-editing enzyme, catalytic polypeptide-like editing complex family together with APOBEC3B, which was found to be a source of mutagenesis in many major cancer types including breast cancer (Kuong, 2013). In the TNBC samples studied herein, APOBEC3G expression is significantly correlated with favourable prognosis (log-rank p=0.02) but not other APOBEC members including APOBEC3B (p=0.29). APOBEC3G is primarily expressed in CD4+T lymphocytes, macrophages, and dendritic cells (Monajemi, 2012). The present data revealed strong association between APOBEC3G and natural killer cell gene NKG7 and interleukins in this module and support the importance of APOBEC3G in TNBC.

The associations between ITLR and immune-relevant genes, pathways and modules support the validity of ITLR as a measure of lymphocytic infiltration and reveal co-regulations of key immune genes.

An aspect of the present invention provides a method of determining a prognosis in a triple negative breast cancer patient, the method comprising, determining the level of expression of APOBEC3G in a tumour sample obtained from the patient, wherein increased expression and/or APOBEC3G expression indicates a positive prognosis.

An aspect of the present invention provides a method of determining a prognosis in a triple negative breast cancer patient, the method comprising, determining the level of expression of CTLA4 in a tumour sample obtained from the patient, wherein increased CTLA4 expression indicates a positive prognosis. Increased CTLA4 expression may be CTLA4 expression above the middle (50) percentile for TNBC, or may be CLTA4 expression above the (25) percentile for TNBC. Increased CTLA4 expression may be CTLA4 expression that is high relative to one or more "housekeeping" genes such as glyceraldehyde-3-phosphate dehydrogenase (GAPDH).

A method of determining a prognosis based on ITLR as described herein may further comprise a step of measuring CTLA4 expression in a tumour obtained from the cancer patient. The cancer patient may be a TNBC patient. The step of measuring CTLA4 expression may involve nucleic acid hybridisation (e.g. microarray-based analysis) or immuno-histochemical techniques. In such methods, the combination of an ITLR above a predetermined cut-off value and increased CTLA4 expression indicates a positive prognosis. The predetermined cut-off value for ITLR may be about 0.03 or about 0.032.

ITLR is an objective quantitative indicator of lymphocytic infiltration in tumours. This quantitative measurement of immune infiltration is useful in guiding treatment decisions in cancer.

Accordingly, an aspect of the invention provides a method of using ITLR in predicting whether or not a cancer patient will respond to a therapy.

Such a method may be a method for predicting whether a cancer patient will respond to a therapeutic regime, the method comprising measuring immune infiltration in a tumour from the cancer patient according to a method described herein, wherein an ITLR above a predetermined ITLR cut-off value indicates that the patient is likely to respond to the therapeutic regime.

ITLR is useful in informing treatment decisions for cancer patients. Accordingly, an aspect of the present invention provides a method of treating a cancer patient, wherein the ITLR of the tumour has been determined to be either below, or above, a predetermined cut-off value. The cancer patient may be an individual from whom an image of a tumour has been obtained. The method may comprise determining the ITLR in a tumour from the patient. The method of treatment may comprise administration of a therapeutic regime.

The therapeutic regime may be radiotherapy or chemotherapy or any combination of these. A therapeutic regime comprising chemotherapy may comprise anthracyline-based chemotherapy. A therapeutic regime may comprise administration of a therapeutic agent. Accordingly, an aspect of the present invention provides a therapeutic agent for use in treating cancer in a cancer patient, wherein a prognosis for the cancer patient has been obtained using a method as disclosed herein.

ITLR provides information for predicting a long-term prognosis and for informing patient treatment decisions. Thus if a patient has a low ITLR and is likely to have a poor prognosis, this patient may be treated more intensively (e.g. more rounds of chemotherapy) than a patient having a high ITLR.

Accordingly, an aspect of the present invention provides a method of treating cancer in a cancer patient according to a therapeutic regime, the method comprising analysing a tumour image from the cancer patient according to a method described herein, and treating the cancer patient according to the therapeutic regime depending on whether the ITLR is below or above a predetermined cut-off value.

ITLR combined with CTLA4 expression provides further prognostic information. Relatively high CTLA4 expression may be associated with a high ITLR, and inhibition of CTLA4 may activate T cells to kill cancer cells. Thus, for a patient having an ITLR above a predetermined cut-off value and having increased CTLA4 expression the therapeutic regime may comprise administration of a CTLA4 antagonist. The CTLA4 antagonist may be an antibody, for example ipilimumab.

An aspect of the present invention provides a CTLA4 antagonist for use in a method of treatment of cancer, wherein a tumour from the patient has been determined to have a high ITLR. An aspect of the present invention provides a CTLA4 antagonist for use in a method of treatment of cancer, wherein a tumour from the patient has been determined to have an ITLR above a predetermined ITLR cut-off value. The cancer may be a specific type or subtype of cancer and the predetermined ITLR cut-off value may be the cut-off value determined for a cohort of patients having that cancer type or subtype. The cancer subtype may be breast cancer. The CTLA4 antagonist may be an antibody, which may be an anti-CTLA4 antibody. The anti-CTLA4 antibody may be ipilimumab (also known as MDX-010 and MDX-101). The cancer patient may be a TNBC patient and the therapy may be ipilimumab.

The prognostic and therapeutic methods described herein may further comprise surgically resecting a tumour from a cancer patient, measuring immune infiltration in the tumour according to a method described herein, and determining a prognosis and/or treating the cancer patient according to a therapeutic regime based on the ITLR of the tumour. A surgically resected tumour is a surgically removed tumour. The method of measuring immune infiltration may use a whole tumour section.

An aspect of the present invention provides a method of determining the efficacy of a therapeutic regime. The method may comprise determining the ITLR of a tumour biopsy obtained from a patient before undergoing the therapeutic regime, determining the ITLR of a tumour biopsy obtained from the patient after undergoing the therapeutic agent, and associating an increased ITLR with therapeutic efficacy (i.e. a therapeutic effect).

The methods of analyzing tumours according to the invention may be modified to yield further information on lymphocyte subtypes and their relevance in cancer. Lymphocytes in tumours are known to encompass diverse subclasses including helper T cells, regulatory T cells, natural killer cells and B cells with sophisticated implications for treatment response (Fridman, 2012; Gu-Trantien, 2013; Andre, 2013). Immunohistochemistry analysis of tumour sections with immune cell markers may be performed, for which automated immunohistochemistry image analysis and statistical modelling methods could be developed to discern interactions between cancer and anti-/pro-tumoural immune response.

In the context of the methods and therapeutic agents described herein, a pathological section may be a tumour section. A tumour section may be a whole-tumour section. A whole-tumour section is typically a section cut from a surgically resected tumour, thus representing the characteristics of the whole tumour. Thus, a whole-tumour section may be a surgically resected section. A pathological section may be a biopsy obtained from a tumour. The pathological section is preferably stained. Staining facilitates morphological analysis of tumour sections by colouring cells, subcellular structures and organelles. Any type of staining may be used, provided that the staining facilitates morphological analysis. The pathological section may be stained with hematoxylin and eosin (H&E). H&E stain is the most commonly used stain in histopathology for medical diagnosis, particularly for the analysis of biopsy sections of suspected cancers by pathologists. Thus H&E stained pathological sections are usually readily available as part of large data sets collated for the study of cancer. The applicability of the present methods to H&E stained pathological sections makes them particularly adaptable for use in analysing data sets from many types and subtypes of cancer to determine the prognostic value of ITLR and to determine cut-off ITLR values for use in the methods described herein.

Reference herein to the ITLR of a tumour also refers to the ITLR of a pathological section, tumour section, or tumour image.

Reference herein to an ITLR value being below a cut-off value may also refer to an ITLR value being equal to or below a cut-off value.

In the present context the term tumour image refers to an image of a tumour from a patient. A tumour image may be an image of a pathological section or tumour section. In the present disclosure a patient may be referred to as having an ITLR (e.g. an ITLR below a predetermined cut-off value), meaning that an image of a tumour from that patient has been determined to have an ITLR. The tumour image may be of a section of a surgically resected tumour, or may be of a biopsy of a tumour.

In the present context the ratio of intra-tumour lymphocytes to cancer cells (ITLR) is the ratio in the pathological section, in a tumour, in a biopsy from the tumour, in a tumour section, or in an image of the tumour, tumour section or pathological section. The term ITLR may also be attributed to a patient. A patient having an ITLR of a particular value refers to a patient from whom a pathological section has an ITLR of a particular value.

The terms "lymphocytic infiltration" and "immune infiltration" are used interchangeably herein.

In the present context "automated" refers to processes that operate independent of external (human) control or input. In the present context an automated process may be a computer-implemented process. The methods of the present invention may be automated methods. The methods of the present invention may be entirely automated methods, that is, they may operate independently of human control or input in their entirety. The methods of the present invention may comprise a step of identifying lymphocyte and cancer cells by automated image analysis. The methods of the present invention may be performed on a tumour image in which lymphocytes and cancer cells have been identified by automated image analysis.

The methods of the present invention are performed on pathological sections, such as tumour sections. The methods of the present invention are therefore ex vivo methods, that is, the methods of the present invention are not practiced on the human body.

A cancer patient in the context of the present invention is an individual having cancer or having been diagnosed with cancer. Reference to cancer may be reference to a particular type or subtype of cancer. The cancer patient may have undergone anthracyline-based chemotherapy, immunotherapy, or a combination therapy comprising anthracyline-based chemotherapy and immunotherapy. The cancer patient may have breast cancer, colorectal cancer, melanoma or non-small cell lung cancer. The cancer patient may have the subtype of breast cancer known as triple negative breast cancer. Triple negative breast cancer may be defined as a breast cancer that is negative for estrogen receptors (ER) and HER2. (TNBC is sometimes defined as breast cancer that is negative for estrogen receptors (ER), HER2 and progesterone receptors (PR), but since cancer that are negative for ER are typically also negative for PR, in the present context TNBC is defined as breast cancer that is negative for ER and HER2.

In the context of the present invention reference to the treatment of a cancer patient refers to treatment of cancer in a patient.

The cancer patient may have, or the cancer type or subtype may be selected from, breast cancer (including breast ductal carcinoma breast and breast lobular carcinoma), central nervous system cancer (including glioblastoma multiforme and lower grade glioma), endocrine cancer (including adrenocortical carcinoma, papillary thyroid carcinoma, paraganglioma & pheochromocytoma), gastrointestinal cancer (including Cholangiocarcinoma, Colorectal Adenocarcinoma, Liver Hepatocellular Carcinoma, Pancreatic Ductal Adenocarcinoma, Stomach-Esophageal Cancer), gynecologic cancer (including Cervical Cancer, Ovarian Serous Cystadenocarcinoma, Uterine Carcinosarcoma, Uterine Corpus Endometrial Carcinoma), head and neck cancer (including Head and Neck Squamous Cell Carcinoma, Uveal Melanoma), hematologic cancer (including Acute Myeloid Leukemia, and Acute Myeloid Leukemia), skin cancer (including Cutaneous Melanoma), soft tissue cancer (including Sarcoma), thoracic cancer (including Lung Adenocarcinoma, Lung Squamous Cell Carcinoma, Mesothelioma) and urologic cancer (including Chromophobe Renal Cell Carcinoma, Clear Cell Kidney Carcinoma, Papillary Kidney Carcinoma, Prostate Adenocarcinoma, Testicular Germ Cell Cancer, Urothelial Bladder Carcinoma). Each of these cancers is the subject of study as part of The Cancer Genome Atlas project.

In the present context the term "immune signatures" is used to encompass all biomarkers related to immune responses and includes the gene expression signatures studied herein as well as other biomarkers including the "Lym" biomarker (Yuan et al. 2012) and ITLR.

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Experimental

Methods
Breast Cancer Studies
Clinical Samples

The complete set of METABRIC (Curtis et al.) samples contains 1,980 primary frozen breast tumours from five contributing hospitals. Among these, 1,026 of the 1,047 tumours from three hospitals have H&E sections without severe artefacts, whist all the H&E samples from the other two hospitals are highly fragmented due to long-term frozen storage. Therefore we only considered the 1,026 tumours for this study (long-term follow up median 68.3 months). On average three tumour sections were obtained at different locations of each primary tumour and placed onto the same slide (Yuan et al., 2012). Tumour materials sandwiched between these sections were sectioned, mixed and used for molecular profiling, thereby maximising the biological relevance of multiple data types being generated. Further details on experimental procedure, staining and molecular profiling protocols can be found in Yuan et al 2012. Gene expression data for the same set of tumours were profiled using the Illumina HT-12 platform. ER status was determined based on the bimodal distribution of ESR1 expression microarray data, and Her2 amplification status based on microarray SNP6 data from the same tumours. In total, there were 181 ER-negative, Her2-negative samples and these were defined as triple negative/TNBC. Samples from two of the three hospitals were merged to form Cohort 1 (89 samples) and samples from the other hospital were merged to form Cohort 2 (92 samples) in order to obtain a similar population size in each cohort. Immune infiltration was scored for 112 of the 181 samples by the pathologists in the METABRIC consortium into three categories: absent, mild and severe. Absent if there were no lymphocytes, mild if there was a light scattering of lymphocytes, and severe if there was a prominent lymphocytic infiltrate. The pathological scores of immune infiltration were not significantly correlated with prognosis (FIG. 13).

H&E Image Analysis

The accuracy of the automated image analysis tool for H&E breast tumour frozen section images had previously been validated based on pathological tumour scores and cell-by-cell evaluation (Yuan et al., Natrajan et al.). For METABRIC samples, this tool achieved 90% cross-validation accuracy for cell classification and high correlation with pathological scores of cell proportions (cor=0.98) (Yuan et al.). This tool was used to classify all cell nuclei in 181 TNBC whole-tumour sections, resulting in an average of 81,810 (standard deviation 80,330) cancer cells, 15,500 (25,133) lymphocytes, and 14,090 (14,180) stromal cells for each image. Lymphocytes have a typical morphology of small, round and homogeneously basophilic nuclei, thus can be reliably differentiated from other cell types in cancer. Since this analysis is based on nuclear morphology only in the H&Es, the identified lymphocytes are likely to be a mixture of immune cell types including T- and B-lymphocytes.

Modelling the Spatial Heterogeneity of Cancer-Immune Interaction

Let $x=x_1, x_2, \ldots x_n$ be the spatial locations of n cancer cells and $y=y_1, y_2, \ldots, y_m$ be the spatial locations of m immune cells in a tumour image (e.g. an H&E tumour section image). Using a quartic kernel function K one can establish a kernel density estimate over the whole tumour image:

$$f(x) = \frac{\sum_{i}^{n} K(x - x_i)}{h},$$

where h is the bandwidth parameter for K. h was optimised using the Minimum Square Error criteria (Berman et al.) in 10 randomly sampled images. Thus, the spatial proximity to cancer for an immune cell i is $s_i=f(y_i)$. We can then identify lymphocyte classes based on s, $s=s_1, s_2, \ldots, s_m$, using unsupervised Gaussian Mixture Clustering (McLachlan, 2000). This method aims to identify multiple components/clusters within the data with probabilities that quantify the uncertainty of observations belonging to the clusters.

$$p(s) = \sum_{k=1}^{K} w_k G(s \mid \mu_k, \sigma_k),$$

where K is the number of clusters, $\mu_k$ and $\sigma_k$ are the mean and variance that define the probabilistic density function G for the kth component, and $w_k$ is the weight of a component k. These parameters were estimated by Expectation-Maximization (Dempster, 1977). Selection of models with different numbers of clusters can be done using statistical criteria, one of the most common being the Bayesian Information Criterion (Schwartz, 1978). It can be used in conjunction with mixture model clustering to select the best number of clusters K:

$$BIC=2L(p(s))+d \log(m)$$

where L( ) is the maximum log likelihood function and d is the number of free parameters to be estimated. Effectively, the BIC criterion aims to evaluate modelling error as well as model complexity. The higher the value of BIC and better the solution is considered to be. To perform clustering, 100,000 immune cells were randomly sampled. Their spatial proximity to cancer data s were used for clustering with a range of different K, K=1-5. This was repeated 200 times, 97% of which the solution with three clusters was considered the optimal by BIC. Mean $\mu_k$ of the clusters are consistent (median: 0.011, 0.06, 0.13; standard deviation/SD: 0.002, 0.0047, 0.0045). Subsequently, we classified all lymphocytes in all tumour samples based on these clusters. We used the ratio of the number of intra-tumour lymphocytes and the number of cancer cell as the final measurement of intra-tumour immune infiltration:

$$ITLR = \frac{N_{Intra-Tumour\ Lymphocyte}}{N_{cancer}}$$

Image Analysis and Modelling Spatial Heterogeneity in More Detail
Image Data

CRImage processes a H&E slide by first dividing it into 2,000 pixels by 2,000 pixels sub-images and identifying cells in these sub-images. Therefore the cell locations for these sub-images need to be combined. We provide combined cell identifies and spatial locations for all 181 TNBC whole-section H&E sections as R data files in a 'CellPosAndMask' folder. These files are named by their image ID. Each file contain the x, y and class columns storing x y coordinates as well as the class of each cell in the large H&E slide. There is also a 'mask' binary matrix to denote the tissue area. The resolution of this image is 5 µm per pixel.
Identify the Optimal Bandwidth Parameter for Computing Kernel Density By sampling 10 random samples, the Mean Square Error is computed over a range of different bandwidths h for computing cancer density.

```
library(splancs)
MSE <- NULL
set.seed(10)
ffs <- sample(dir('./data/CellPosAndMask/'), 10)
for (ff in ffs){
    res <- try(load(paste('./data/CellPosAndMask/', ff, sep='')))
    CellPos[,1] <- as.character(CellPos[,1])
    CellPos[,2] <- as.numeric(CellPos[,2])
    CellPos[,3] <- as.numeric(CellPos[,3])
    CellPos <- CellPos[rowSums(is.na(CellPos))==0, ]
    CellPos[,3] <- ncol(Mask) - CellPos[,3] +1
    CellPos[,3][ CellPos[,3] > ncol(Mask)] <- ncol(Mask)
    CellPos <- CellPos[CellPos[,1]!='a',]
    cell.c <- data.frame(x=as.numeric(CellPos[CellPos[,1]=='c',2]),
y=as.numeric(CellPos[CellPos[,1]=='c',3]))
        cv <- mse2d(as.points(cell.c), poly=cbind(c(0, 0, nrow(Mask),
        nrow(Mask)), c(0, ncol(Mask),
    ncol(Mask), 0)), nsmse=40, range=10)
        MSE <- rbind(MSE, cv$mse)
}
save(cv, MSE, file='./data/BandwidthSelection.rdata')
```
h=5 was chosen as the optimal bandwidth for lower variability of Mean Square Error.

Generate Spatial Proximity to Cancer for Each Lymphocyte

Now, spatial scores can be generated given the cell position data using the following getITL function. getITL function uses the cell position files to infer a cancer density map using the bandwidth selected above.

```
getITL <- function(ff, ...){
    require(EBImage)
    require(splancs)
    res <- try(load(paste('./data/CellPosAndMask/', ff, '.rdata', sep='')))
    if (class(res)!='try-error'){
        CellPos[,1] <- as.character(CellPos[,1])
        CellPos[,2] <- as.numeric(CellPos[,2])
        CellPos[,3] <- as.numeric(CellPos[,3])
        CellPos <- CellPos[rowSums(is.na(CellPos))==0, ]
        CellPos[,3] <- ncol(Mask) - CellPos[,3] +1
        CellPos[,3][ CellPos[,3] > ncol(Mask)] <- ncol(Mask)
        cell.c <- data.frame(x=as.numeric(CellPos[CellPos[,1]=='c',2]),
y=as.numeric(CellPos[CellPos[,1]=='c',3]))
        res <- kernel2d(as.points(cell.c), poly=cbind(c(0, 0,
        nrow(Mask), nrow(Mask)), c(0,
    ncol(Mask), ncol(Mask), 0)), h0=h, nx=dim(Mask)[1], ny=dim(Mask)[2])
        cell.l <- data.frame(x=as.numeric(CellPos[CellPos[,1]=='l',2]),
y=as.numeric(CellPos[CellPos[,1]=='l', 3]))
        z.l <- unlist(sapply(1:length(cell.l$x), function(x)
        res$z[cell.l$x[x], cell.l$y[x]]))
    }
    z.l
}
```

Using this function, measurements for each lymphocyte for each tumour can then be generated.

```
itl <- list( )
files <- trait$file
for (ff in files)
    itl <- c(itl, list(try(getITL(ff, h=5, w=3, cex=.5, ifPlot=F))))
names(itl) <- files
save(itl, file='./data/ITL.rdata')
```

By default getITL function uses the cut-offs (threshold values) of 0.10507473 and 0.03662728 to determine intra-tumour (ITL), adjacent to tumour (ATL), and distal-to-tumour lymphocytes (DTL). We will now describe how these cut-offs were selected.
Identify Sub-Populations of Lymphocyte by Unsupervised Learning Gaussian mixture clustering and BIC implemented in the R package mclust were used for the discovery of lymphocyte sub-populations. 100,000 lymphocytes were randomly sampled from the itl object and then clustered.

```
library(mclust)
load(file='./data/ITL.rdata')
set.seed(11)
x <- sample(as.numeric(unlist(itl)), 100000)
res <- Mclust(x, G=1:5)
```

The sampling process was repeated to generate clusters 200 times, and evaluated output from Mclust and mclust-BIC. BIC values for these 200 runs are obtained. The three-cluster solution k=3 remains optimal in 97% of the time, and k=5 was chosen 3% of the times. The median of cluster means when there are three clusters are 0.0114, 0.0603 and 0.1322 with standard deviation 0.002 and 0.0047 and 0.0045, respectively.

Therefore, the clustering result of lymphocytes from randomly sampled data is stable. Since the clustering is stable, cut-offs were taken at the maximum value of the first and second clusters from one of the sampling runs as our cut-offs for determining lymphocyte classification for the remaining samples.
Generating ITLR, ATLR, and DTLR Subsequently, the cut-offs can be used to classify every lymphocyte based on their data stored in the R object itl. mat.l is a matrix with columns of 'Distal', 'Adjacent', 'Intra' denoting the number of lymphocytes in each class for a tumour.

```
th=c(0.03662728, 0.10507473)
mat.l <- NULL
for (i in 1:length(itl)){
    z.l <- itl[[i]]
    cl <- rep(1,length(z.l))
    cl[z.l>th[1] & z.l<th[2]] <- 2
    cl[z.l>=th[2]] <- 3
    mat.l <- rbind(mat.l, c(sum(cl==1), sum(cl==2), sum(cl==3)))
```

```
}
colnames(mat.l) <- c('Distal', 'Adjacent', 'Intra')
rownames(mat.l) <- names(itl)
```

The Intra column of mat.I is the number of intra-tumour lymphocytes. This divided by the number of cancer cells (trait$nTumour) is the ITLR measurement Measuring Cell Distances and Spatial Arrangement To identify physical properties of ITLs, ATLs and DTLs that differentiate them, in 10,000 lymphocytes randomly sampled from 20 tumours, we identified the 5 nearest cancer cells and the centroid of the convex hull region formed by these cancer cells. For each lymphocyte, the distance from the lymphocyte to the nearest cancer cell was computed ($d_{min}$), and the distance to the centroid of cancer convex hull was computed (dcentroid). Centroid of a convex hull region was calculated as the mean positions of the subset of points that define the convex hull. Differences among lymphocyte classes in terms of $d_{centroid\ and}$ and $d_{centroid}$ were tested with student's t-test.

Other Immune Signatures in Comparison

Lymphocyte abundance based on image analysis result was calculated as:

$$lym = \frac{N_{lymphocyte}}{N_{cancer}}$$

The gene expression signatures were calculated as described in the referred papers.

ITLR Gene Modules

Hierarchical clustering was used to identify highly correlated gene modules by clustering the correlation matrix of all ITL-associated genes into 100 clusters. Modules were selected from these clusters based on average absolute Pearson correlation exceeding 0.75 and cluster size exceeding five.

Comparing ITLR and ITLR-Associated Genes

To test if ITLR has additional value to ITLR-associated genes, we performed multivariate Cox regression analysis with ITLR paired with expression profile of an ITLR gene. This was performed for all of the top 100 ITLR-associated genes ranked by correlation. ITLR was dichotomised using the threshold reported in the paper, and gene expression was dichotomised into two equal-size group or three groups (25 lower, 50 middle and 25 upper percentiles). Tables with Hazard ratio, log-rank p-value and 95% interval were produced. In both analysis with two and three patient groups according to gene expression data, p-values of ITLR were consistently higher than the p-values of gene expression profiles, as well as being higher than significance level of 0.05 (−log(p) 2.99).

Other Statistical Methods

Monotone trend between ITLR and clinical parameters was tested using the Jonckheere-Terpstra trend test (Jonckheere). Survival analysis was performed with breast cancer-specific 10-year survival data. The Kaplan-Meier estimator was used for patient stratification and log-rank test was used for testing difference among groups. Cox proportional hazards regression model was fitted to the survival data and hazard ratios and 95% confidence intervals were computed to determine the correlation with disease-specific survival, where the log-rank test with p<0.05 was considered significant. Correlation between ITLR and gene expression was computed with Pearson correlation and q-values computed using False Discovery Rate (FDR) correction using 25% of the data for fitting the null model. Cut-offs for dichotomizing immune signatures were optimised stepwise from 20 to 80 percentiles at an interval of 1.5. The cut-offs that displayed the highest prognostic significance with log-rank test were selected. For consistency test in FIG. 5F, each signature was centred at 0 and scaled to standard deviation 1. Optimal cut-offs were also mapped to the new data before comparison. MSigDB gene set version 4.0 (Subramanian et al.) was used in conjunction with a hypergeometric test for enrichment analysis.

Ovarian Cancer Studies

Samples were obtained from a UK-China collaborative study which aims to study the clinical implications of immune infiltration in a set of 91 ovarian cancer patients with metastatic disease. H&E-stained slides for the primary tumours were obtained, scanned, and subjected to image analysis using CRImage. Cells in these images were classified into cancer, lymphocyte, and stromal cell categories. Once the spatial locations of these cells were obtained from image analysis, kernel density of cancer was computed for each image, and lymphocyte-to-cancer measurements were obtained for each lymphocyte. The measurements were subjected to clustering and two clusters were found, i.e. intra-tumour and non-intra tumour lymphocytes. ITLR as the ratio of intra-tumour lymphocytes to cancer cells was calculated for each patient. The 29% of patients with ITLR lower than a cut-off of 0.06085726 have significantly worst overall survival than patients with ITLR higher than the cut-off (10-year OS log-rank test p=0.024, HR=0.51, CI=0.28-0.92; 5-year OS p=0.045, HR=0.54, CI=0.29-0.99; Figs Ovarian). Overall survival was defined using death as event regardless of the cause, as this information was unavailable.

Tumours were staged according to the 1988 FIGO staging system (Prat 2013). Lymphocytic infiltration was assessed in five high-power fields, each field is scored as absent, mild, or severe: Absent if there were no lymphocytes, mild if there was a light scattering of lymphocytes, and severe if there was a prominent lymphocytic infiltrate. Median of field-based scores was taken as the score for a tumour.

Results

Statistical Modelling of the Spatial Heterogeneity of Immune Infiltration—Determination of ITLR An automated image analysis tool identified cancer, lymphocytes and stromal cells encompassing fibroblasts and endothelial cells based on their nuclear morphologies in H&E whole-tumour section slides (Yuan et al. 2012). The main component of this tool is a classifier trained by pathologists over randomly selected tumour regions and validated in 564 breast tumours with 90% accuracy (Yuan et al. 2012). As a result of image analysis, the types and spatial locations of on average 110,000 cells were recorded in every breast tumour section. Thus, this fully automated tool enabled the mapping of spatial distributions of all cancer cells and lymphocytes within a tumour section, which can be subsequently visualised as a 3D landscape (FIG. 1A). The spatial relationships of immune and cancer cells are then analysed with a statistical pipeline exemplified in FIG. 1B. First, to globally profile the spatial distribution of the cancer cells, the cancer cell density was quantified using a kernel estimate (Methods). Intuitively, this builds a 'cancer landscape' where hills indicate tumour regions densely populated with cancer cells. The height of a hill thus correlates with cancer density at a specific location in the tumour (FIG. 1B). Secondly, for every lymphocyte, its spatial proximity to cancer can be directly quantified with the cancer density landscape at its specific location. Thus a quantitative measurement of the spatial proximity to tumour cells can be efficiently obtained for every lymphocyte (FIG. 1B).

Using this approach, we quantified the spatial proximity to cancer for every lymphocyte in 181 TNBC samples in the METABRIC study (Methods, FIG. 2A). In principle, lymphocytes that differ in their spatial positioning to cancer can be differentiated based on these quantitative spatial measurements. The inventor investigated whether data-driven clustering methods based on normal distribution can be used to differentiate different classes of lymphocytes, since cell spatial distribution is a naturally emerged pattern. Unsupervised Gaussian Mixture Model clustering Fraley, 2003) was employed to identify lymphocyte clusters based on their spatial proximity to cancer using a training set of 100,000 randomly sampled lymphocytes (FIG. 2B, Methods). Subsequently, a three-cluster solution that identify three classes of lymphocytes was considered the optimal by the Bayesian Information Criterion (Schwartz, 1978) (FIG. 2B). This three-class solution is consistently the optimal 97% of the time upon 200 repeated sampling, whilst the five-class solution was considered optimal 3% of the time (Methods, FIG. 2C). In addition, the cluster structure of the three-class solutions was stable (median of cluster mean: 0.011, 0.06, 0.13; standard deviation/SD: 0.002, 0.0047, 0.0045; FIG. 2C), indicating that the same clusters were identified in each random sampling. The three classes of lymphocytes were named as Intra-Tumour Lymphocyte (ITL), Adjacent-Tumour Lymphocyte (ATL) and Distal-Tumour Lymphocyte (DTL). Subsequently, a classifier was trained based on the lymphocyte classes to predict the types of lymphocytes in all TNBC samples (Methods).

To understand the differences of the newly proposed lymphocyte classes, additional measures were derived that are based on direct physical distances. First, for each lymphocyte its distance to the nearest cancer cell can be quantified ($d_{min}$, Methods, FIG. 2D). It was shown that ITLs have a median distance of 7 μm (interquartile range 5-10) to the nearest cancer cell, whilst it is 10 μm (7-11) for ATLs, and 20 μm (14-26) for DTLs (FIG. 2E). The overlap in distance to nearest cancer cell between ITLs and ATLs suggests that this measure is not the fundamental difference between the two classes. Since the kernel density measure based on which the lymphocyte classes were derived is essentially spatial smoothing, the inventor hypothesised that the spatial arrangement of cancer cells surrounding lymphocytes differs between ATLs and ITLs. To measure spatial arrangement, the inventor examined the convex hull region formed by 5 nearest cancer cells, which is the smallest region that covers these cells (FIG. 2D, Methods). If a lymphocyte is surrounded by cancer cells, it should fall into the convex hull region formed by nearby cancer cells and has a small distance to the centroid of this region (FIG. 2D, left). In contrast, if nearby cancer cells are to one side of a lymphocyte, the distance between the lymphocyte and the centroid of the cancer convex hull region is likely to be large (FIG. 2D, right). Thus, the inventor used the distance between a lymphocyte and the centroid of the cancer convex hull region as a quantitative measure of the spatial arrangement of cancer cells surrounding a lymphocyte ($d_{centroid}$) Three lymphocyte classes displayed significant differences in $d_{centroid}$ with median $d_{centroid}$ 3.6 μm (2.2-5.1), 7.2 μm (4.5-10.6), 17.7 μm (11.0-26.6) for ITLs, ATLs, and DTLs, respectively (FIG. 2E). Therefore, $d_{mind}$ and $d_{centroid}$ together better define and aid interpretation of the lymphocyte classes (FIG. 2F). Taken together, these data demonstrated that the proposed kernel-based measure of spatial proximity to cancer can effectively account for spatial proximity and surroundings, and also that the three lymphocyte classes differ not only in the distance to the nearest cancer cell but also in the ways nearby cancer cells are arranged. A representative case showing spatial distribution of lymphocytes in these three classes is illustrated (FIG. 3A-B). For instance, the ITLs can be observed to locate within regions densely populated with cancer cells (FIG. 3C).

In the 181 TNBC samples, there are overall more ATLs than the other two types of lymphocytes (on average 47% ATLs, 32% ITLs and 21% DTLs, FIG. 4A). The changes in abundance of these three classes in 181 samples can be observed in a triangle plot (FIG. 4B). When the proportion of ITLs is low (0-20%), there are in general more DTLs (40-60%) than ATLs (30-50%). As the amount the ITLs increase (20-50%), ATLs also increase (40-60%) while DTLs decrease (10-40%). When there are large amount of ITLs (>50%), there are still certain amount of ATLs (20-40%) with very few DTLs (<10%). To summarise the degree of lymphocytic infiltration for a given tumour, we first calculated the ratio between the number of ITLs and the number of cancer cells (ITLR; see Methods above). In the 181 TNBC samples, a significant association was observed between ITLR and pathological assessment of lymphocytic infiltration of the tumours in categories of absent, mild and severe ($p=2\times10^{-33}$, FIG. 4C). In terms of other clinical parameters, there was no correlation between ITLR and tumour size, node status and TP53 mutation status (FIG. 4D). Tumour grade was not considered because 87% of the TNBC samples are Grade 3 tumours. These data support ITLR's validity as a measurement of lymphocytic infiltration and its potential value in addition to known clinical parameters for TNBC.

ITLR is a Statistical Measure of Lymphocytic Infiltration and an Independent Predictor of Disease-Specific Survival in Two TNBC Cohorts.

To investigate the clinical significance of the proposed immune measure ITL, the inventor analysed disease-specific survival as a function of ITL. The TNBC samples can be divided into two independent cohorts based on contributing hospitals (Methods, n=89 and n=92, distribution of ITLR FIG. 3E). To dichotomise the continuous ITLR, the optimal cut-off was selected to have the best prognostic value in Cohort 1 as the discovery cohort (Methods). The best cut-off was selected to be 0.011 and 20% of the patients have ITLR lower than this cut-off. These patients have significantly worse disease-specific survival compared with patients with higher ITLR in Cohort 1 (Log-rank test p=0.0063, Hazard ratio HR=0.36, 95% confidence interval CI=0.17-0.77; Table 1; FIG. 4F). This observation was verified in the validation cohort, Cohort 2 (p=0.0037, HR=0.25, CI=0.09-0.69; FIG. 4F). Significant stratification was observed upon repeated analysis with Cohort 2 as the discovery and Cohort 1 as the validation cohort (FIG. 3G). The same tests were performed for the ratio of ATLs and DTLs to cancer cells (ATLR and DTLR), but neither showed a significant correlation with disease-specific survival (Discovery and Validation cohort: ATLR p=0.064 and 0.75; DTLR p=0.43 and 0.25; FIG. 7-8). We subsequently focused on ITLR. ITLR-high TNBC patients have a survival probability of 80% five year from diagnosis versus 49% for ITLR-low patients (Kaplan-Meier survival estimates, two cohorts combined).

ITLR was compared with eight other immune signatures. These include the previously published image-based signature, lymphocyte abundance (Lym), defined as the ratio between the number of lymphocytes and the number of cancer cells (Methods) (Yuan et al. 2012). A major difference between ITLR and Lym is that Lym does not account for different classes of lymphocytes whilst ITLR considers infiltrating lymphocytes. The remainder of signatures are published gene expression-based signatures from Calabro et al. (Calabro et al.) that is predictive of ER-negative breast cancer prognosis, a 5-gene signature from Ascierto et al. (Ascierto et al. '12) that predicts recurrence-free survival across breast cancer subtypes, and the B-cell, IL8 and combined signatures to predict prognosis of TNBC (Rody et al.). CXCR3 and CXCL13 expression were also included since they have been shown to correlate with breast cancer prognosis (Ma et al., Gu-Trantien et al.).

The same cut-off selection approach was applied to test the association between these signatures and disease-specific survival (Table 2). The signatures that showed the best prognostic values are shown in FIG. 5A-E (all are provided in FIG. 9) and Table 1. None of these signatures correlated with prognosis in both cohorts. This analysis was repeated using Cohort 2 as the discovery cohort for selecting the optimal cut-offs and Cohort 1 for validation (FIG. 10, Table 3). In both experiments, only ITLR consistently stratified patients into two groups of different outcome among the nine signatures (FIGS. 7 and 8). Furthermore, the best ITLR cut-offs selected in two cohorts for all nine signatures were compared (Methods, FIG. 5F). ITLR was among the most consistent signatures in terms of optimal cut-offs in two cohorts, supporting the consistency and the potential use of ITLR as an objective measure for identifying patients with low lymphocytic infiltration.

Compared to published immune signatures, ITLR was also the only signature to show significant correlation with disease-specific survival in multivariate Cox proportional hazards model together with standard clinical parameters of nodal status and tumour size in both cohorts, whichever cohort was used as the discovery cohort (Tables 1 to 3). Using samples from both cohorts, ITLR has a log-rank p-value of $2.1 \times 10^{-4}$ and HR 0.32 (0.17-0.58). To test the robustness of the Cox model in determining the prognostic value of ITLR, we used bootstrap analysis in randomly perturbed data and repeated the univariate and multivariate regression analysis 1,000 times. In 95.6% and 94.7% of the time, ITLR remained significantly associated with prognosis in univariate and multivariate analysis, respectively. Taken together, these results show the stability and robustness of ITLR as an independent prognostic biomarker in TNBC.

ITLR Heterogeneity is Reflected on the Transcriptional Level by CTLA4 and APOBEC3G Expression To identify molecular associations of immune infiltration and to test the biological relevance of ITLR, the inventor integrated image-based ITLR with microarray gene expression data profiled for the same set of 181 TNBC tumours. The analysis identified 307 genes positively correlated and 105 genes negatively correlated with ITLR (False Discovery Rate multiple testing correction, q-value<0.05; Methods). Genes with the most significant correlations with our immune signature ITLR include kinases (SH3KBP1, LCK, MAP4K1) and receptors (FCRL3, GPR18, TNFRSF13B, SEMA4D, CXCR3, IL2RG), as well as the known immunotherapy target CTLA4 (Table 4). Thus, significant correlations between ITLR and immune-related genes demonstrate the biological relevance of the ITLR signature.

TABLE 4

Top 20 genes positively correlated with ITLR and top 10 genes negatively correlated with ITLR (underline).

| Symbol | Cytoband | Description | cor | q |
|---|---|---|---|---|
| SH3KBP1 | Xp22.12b | SH3-domain kinase binding protein 1 | 0.4 | 0.0011 |
| FCRL3 | 1q23.1d | Fc receptor-like 3 | 0.4 | 0.0011 |
| LCK | 1p35.1b | lymphocyte-specific protein tyrosine kinase | 0.4 | 0.0011 |
| GPR18 | 13q32.3a | G protein-coupled receptor 18 | 0.39 | 0.0011 |
| TNFRSF13B | 17p11.2h | tumour necrosis factor receptor superfamily, member 13B | 0.39 | 0.0011 |
| SEMA4D/ CD100 | 9q22.2a | sema domain, immunoglobulin domain (Ig), transmembrane domain (TM) and short cytoplasmic domain, (semaphorin) 4D | 0.39 | 0.0012 |
| MAP4K1 | 19q13.2a | mitogen-activated protein kinase kinase kinase kinase 1 | 0.39 | 0.0012 |
| RLTPR | 16q22.1b | RGD motif, leucine rich repeats, tropomodulin domain and proline-rich containing | 0.38 | 0.0012 |
| UBASH3A | 21q22.3b | ubiquitin associated and SH3 domain containing A | 0.38 | 0.0012 |
| IKZF3 | 17q12c | IKAROS family zinc finger 3 (Aiolos) | 0.38 | 0.0012 |
| CYFIP2 | 5q33.3a-q33.3b | cytoplasmic FMR1 interacting protein 2 | 0.38 | 0.0012 |
| CXCR3 | Xq13.1d | chemokine (C-X-C motif) receptor 3 | 0.38 | 0.0012 |
| CD3E | 11q23.3d | CD3e molecule, epsilon (CD3-TCR complex) | 0.38 | 0.0012 |
| IL2RG | Xq13.1c | interleukin 2 receptor, gamma | 0.38 | 0.0012 |
| CXCR5 | 11q23.3e | chemokine (C-X-C motif) receptor 5 | 0.38 | 0.0014 |
| CTSW | 11q13.1d | cathepsin W | 0.37 | 0.0018 |
| SH2D1A | Xq25c | SH2 domain containing 1A | 0.37 | 0.0018 |
| SEPT6 | Xq24c | septin 6 | 0.37 | 0.0018 |
| CTLA4 | 2q33.2a | cytotoxic T-lymphocyte-associated protein 4 | 0.37 | 0.0019 |
| SIRPG | 20p13e | signal-regulatory protein gamma | 0.37 | 0.0019 |
| C10orf141 | 10q26.2b | | −0.4 | 0.0011 |
| CD151 | 11p15.5c | CD151 molecule (Raph blood group) | −0.39 | 0.0011 |
| SPP1 | 4q22.1b | secreted phosohoprotein 1 | −0.39 | 0.0012 |
| ANXA2 | 15q22.2a | annexin A2 | −0.39 | 0.0012 |
| P4HA2 | 5q31.1b | prolyl 4-hydroxylase, alpha polypeptideII | −0.36 | 0.0022 |
| MUSK | 9q31.3b | muscle, skeletal, receptor tyrosine kinase | −0.36 | 0.0023 |
| POFUT2 | 21q22.3e | protein O-fucosyltransferase 2 | −0.36 | 0.0025 |

TABLE 4-continued

Top 20 genes positively correlated with ITLR and top 10 genes negatively correlated with ITLR (underline).

| Symbol | Cytoband | Description | cor | q |
|---|---|---|---|---|
| ITGB5 | 3q21.2a | integrin, beta 5 | −0.35 | 0.004 |
| MXRA7 | 17q25.1d-q25.2a | matrix-remodelling associated 7 | −0.34 | 0.0046 |
| CALN1 | 7q11.22c | calneuron 1 | −0.34 | 0.0046 |

Subsequently, enrichment analysis was performed on the positively and negatively correlated genes respectively against MSigDB gene set categories (Subramanian, 2005) including KEGG pathways (Kanehisa, 2000), canonical pathways curated by domain experts and immunologic signatures (Methods, FIG. 11). Genes positively correlated with ITLR are enriched with natural killer cell mediated cytotoxicity, T cell receptor, Antigen processing and presentation KEGG pathways, CD8 T cell, CD4 T cell and B cell up-regulated immunogenic signatures, as well as IL12 and CD8 TCR canonical pathways. Conversely, genes negatively correlated with ITLR were enriched with ECM receptor interaction and focal adhesion KEGG pathways, regulatory T cell and TGFβ related immunologic signatures as well as integrin related pathways. The molecular analysis on the pathway level suggests ITLR is positively associated with anti-tumour immune activities in TNBC.

To further dissect their interconnected relationships and discover de novo molecular modules, tightly connected gene modules were identified within ITLR-associated genes (FIG. 11; Methods). As such, seven modules of positively correlated genes (P1-7) and two modules of genes negatively correlated with ITLR (N1 and N2) were identified. Known immune-related genes in the modules include IFNG (P1), RLPTR (P3), GPR18 (P4), CXCR3 (P5), MAP4K1 (P6), CTLA4 (P7), ANXA2 (N1) and FAP (N2). Notably, two of the modules contain APOBEC3G (P2) and CTLA4 (P7), which may suggest co-regulation among APOBEC3G, NKG7 and interleukins including IL21R and IL18RAP, as well as high correlations among CTLA4, chemoattractant for B lymphocytes CXCL13 (Denkert) and TIGIT T cell immunoreceptor with Ig and ITIM domains. Furthermore, expression profiles of these genes were significantly associated with disease-specific survival in TNBC, including APOBEC3G as well as GPR18 (P4) and MAP4K1 (P6) ranked as the top ITLR-associated genes (FIG. 6B, FIG. 12). CTLA4 expression was able to stratify patients into groups with significantly different prognosis, and could further stratify the ITLR high group into two subgroups with significantly different outcome (p=0.046, FIG. 6C, FIG. 12). Comparing ITLR with ITLR-associated genes in terms of prognostic value, multivariate analysis showed that ITLR stratification has additional and in many cases superior value to ITLR-associated genes (FIG. 13, Methods).

REFERENCES

A number of publications are cited above in order to more fully describe and disclose the invention and the state of the art to which the invention pertains. Full citations for these references are provided below. The entirety of each of these references is incorporated herein.

Alexiou G A, Vartholomatos E, Voulgaris S. Prognostic value of neutrophil-to-lymphocyte ratio in patients with glioblastoma. Journal of neuro-oncology. 2013; 115:521-2.

Ancuta E, Ancuta C, Zugun-Eloae F, Iordache C, Chirieac R, Carasevici E. Predictive value of cellular immune response in cervical cancer. Romanian journal of morphology and embryology=Revue roumaine de morphologie et embryologie. 2009; 50:651-5.

Andre, F., M. V. Dieci, P. Dubsky, C. Sotiriou, G. Curigliano, C. Denkert and S. Loi (2013). "Molecular pathways: involvement of immune pathways in the therapeutic response and outcome in breast cancer." Clin Cancer Res 19(1): 28-33.

Ascierto, M. L., M. Kmieciak, M. O. Idowu, R. Manjili, Y. Zhao, M. Grimes, C. Dumur, E. Wang, V. Ramakrishnan, X. Y. Wang, H. D. Bear, F. M. Marincola and M. H. Manjili (2012). "A signature of immune function genes associated with recurrence-free survival in breast cancer patients." Breast Cancer Res Treat 131(3): 871-880.

Bambury R M, Teo M Y, Power D G, Yusuf A, Murray S, Battley J E, et al. The association of pre-treatment neutrophil to lymphocyte ratio with overall survival in patients with glioblastoma multiforme. Journal of neuro-oncology. 2013; 114:149-54

Basavanhally, A. N., S. Ganesan, S. Agner, J. P. Monaco, M. D. Feldman, J. E. Tomaszewski, G. Bhanot and A. Madabhushi (2010). "Computerized image-based detection and grading of lymphocytic infiltration in HER2+ breast cancer histopathology." IEEE Trans Biomed Eng 57(3): 642-653.

Berman, M. and P. Diggle (1989). "Estimating Weighted Integrals of the 2nd-Order Intensity of a Spatial Point Process." Journal of the Royal Statistical Society Series B-Methodological 51(1): 81-92.

Jonckheere, A. R. (1954). "A test of significance for the relation between m rankings and k ranked categories." British Journal of Statistical Psychology 7: 93-100.

Bystryn J C, Oratz R, Roses D, Harris M, Henn M, Lew R. Relationship between immune response to melanoma vaccine immunization and clinical outcome in stage II malignant melanoma. Cancer. 1992; 69:1157-64.

Calabró, A., T. Beissbarth, R. Kuner, M. Stojanov, A. Benner, M. Asslaber, F. Ploner, K. Zatloukal, H. Samonigg, A. Poustka and H. Sültmann (2009). "Effects of infiltrating lymphocytes and estrogen receptor on gene expression and prognosis in breast cancer." Breast Cancer Res Treat 116(1): 69-77.

Cheng, Yizong (August 1995). "Mean Shift, Mode Seeking, and Clustering". IEEE Transactions on Pattern Analysis and Machine Intelligence (IEEE) 17 (8): 790-799.

Clarke B, Tinker A V, Lee C H, Subramanian S, van de Rijn M, Turbin D, et al. Intraepithelial T cells and prognosis in ovarian carcinoma: novel associations with stage, tumor type, and BRCA1 loss. Modern pathology: an official journal of the United States and Canadian Academy of Pathology, Inc. 2009; 22:393-402.

Contardi, E., G. L. Palmisano, P. L. Tazzari, A. M. Martelli, F. Fala, M. Fabbi, T. Kato, E. Lucarelli, D. Donati, L.

Polito, A. Bolognesi, F. Ricci, S. Salvi, V. Gargaglione, S. Mantero, M. Alberghini, G. B. Ferrara and M. P. Pistillo (2005). "CTLA-4 is constitutively expressed on tumor cells and can trigger apoptosis upon ligand interaction." Int J Cancer 117(4): 538-550.

Curtis, C., S. P. Shah, S. F. Chin, G. Turashvili, O. M. Rueda, M. J. Dunning, D. Speed, A. G. Lynch, S. Samarajiwa, Y. Yuan, S. Graf, G. Ha, G. Haffari, A. Bashashati, R. Russell, S. McKinney, A. Langerod, A. Green, E. Provenzano, G. Wishart, S. Pinder, P. Watson, F. Markowetz, L. Murphy, I. Ellis, A. Purushotham, A. L. Borresen-Dale, J. D. Brenton, S. Tavare, C. Caldas and S. Aparicio (2012). "The genomic and transcriptomic architecture of 2,000 breast tumours reveals novel subgroups." Nature 486 (7403): 346-352.

Crane C A, Austgen K, Haberthur K, Hofmann C, Moyes K W, Avanesyan L, et al. Immune evasion mediated by tumor-derived lactate dehydrogenase induction of NKG2D ligands on myeloid cells in glioblastoma patients. Proceedings of the National Academy of Sciences of the United States of America. 2014; 111:12823-8.

Dave S S, Wright G, Tan B, Rosenwald A, Gascoyne R D, Chan W C, et al. Prediction of Survival in Follicular Lymphoma Based on Molecular Features of Tumor-Infiltrating Immune Cells. New England Journal of Medicine. 2004; 351:2159-69.

Davidsson S, Ohlson A L, Andersson S O, Fall K, Meisner A, Fiorentino M, et al. CD4 helper T cells, CD8 cytotoxic T cells, and FOXP3(+) regulatory T cells with respect to lethal prostate cancer. Modern pathology: an official journal of the United States and Canadian Academy of Pathology, Inc. 2013; 26:448-55.

DeNardo, D. G., D. J. Brennan, E. Rexhepaj, B. Ruffell, S. L. Shiao, S. F. Madden, W. M. Gallagher, N. Wadhwani, S. D. Keil, S. A. Junaid, H. S. Rugo, E. S. Hwang, K. Jirstrom, B. L. West and L. M. Coussens (2011). "Leukocyte complexity predicts breast cancer survival and functionally regulates response to chemotherapy." Cancer Discov 1(1): 54-67.

Denkert, C., S. Loibl, A. Noske, M. Roller, B. M. Muller, M. Komor, J. Budczies, S. Darb-Esfahani, R. Kronenwett, C. Hanusch, C. von Torne, W. Weichert, K. Engels, C. Solbach, I. Schrader, M. Dietel and G. von Minckwitz (2010). "Tumor-associated lymphocytes as an independent predictor of response to neoadjuvant chemotherapy in breast cancer." J Clin Oncol 28(1): 105-113.

Dieci, M. V., C. Criscitiello, A. Goubar, G. Viale, P. Conte, V. Guarneri, G. Ficarra, M. C. Mathieu, S. Delaloge, G. Curigliano and F. Andre (2014). "Prognostic value of tumor-infiltrating lymphocytes on residual disease after primary chemotherapy for triple-negative breast cancer: a retrospective multicenter study." Ann Oncol 25(3): 611-618.

Dieu-Nosjean M C, Antoine M Fau-Danel C, Danel C Fau-Heudes D, Heudes D Fau-Wislez M, Wislez M Fau-Poulot V, Poulot V Fau-Rabbe N, et al. Long-term survival for patients with non-small-cell lung cancer with intratumoral lymphoid structures.

Erdag G, Schaefer J T, Smolkin M E, Deacon D H, Shea S M, Dengel L T, et al. Immunotype and immunohistologic characteristics of tumor-infiltrating immune cells are associated with clinical outcome in metastatic melanoma. Cancer research. 2012; 72:1070-80

Failmezger H, Yuan Y, Rueda O and Markowetz F (2012). *CRImage: CRImage a package to classify cells and calculate tumour cellularity*. R package version 1.14.0.

Fiorelli V, Gendelman R, Caterina Sirianni M, Chang H-K, Colombini S, Markham P D, et al. γ-Interferon Produced by CD8+ T Cells Infiltrating Kaposi's Sarcoma Induces Spindle Cells With Angiogenic Phenotype and Synergy With Human Immunodeficiency Virus-1 Tat Protein: An Immune Response to Human Herpesvirus-8 Infection? Blood. 1998; 91:956-67.

Fraley, C. and A. E. Raftery (2003). "Enhanced model-based clustering, density estimation, and discriminant analysis software: MCLUST." Journal of Classification 20(2): 263-286.

Fridman, W. H., F. Pages, C. Sautes-Fridman and J. Galon (2012). "The immune contexture in human tumours: impact on clinical outcome." Nat Rev Cancer 12(4): 298-306.

Gannon P O, Poisson A O, Delvoye N, Lapointe R, Mes-Masson A M, Saad F. Characterization of the intraprostatic immune cell infiltration in androgen-deprived prostate cancer patients. Journal of immunological methods. 2009; 348:9-17.

Galon, J., A. Costes, F. Sanchez-Cabo, A. Kirilovsky, B. Mlecnik, C. Lagorce-Pages, M. Tosolini, M. Camus, A. Berger, P. Wind, F. Zinzindohoue, P. Bruneval, P. H. Cugnenc, Z. Trajanoski, W. H. Fridman and F. Pages (2006). "Type, density, and location of immune cells within human colorectal tumors predict clinical outcome." Science 313(5795): 1960-1964.

Galon, J., B. Mlecnik, G. Bindea, H. K. Angell, A. Berger, C. Lagorce, A. Lugli, I. Zlobec, A. Hartmann, C. Bifulco, I. D. Nagtegaal, R. Palmqvist, G. V. Masucci, G. Botti, F. Tatangelo, P. Delrio, M. Maio, L. Laghi, F. Grizzi, M. Asslaber, C. D'Arrigo, F. Vidal-Vanaclocha, E. Zavadova, L. Chouchane, P. S. Ohashi, S. Hafezi-Bakhtiari, B. G. Wouters, M. Roehrl, L. Nguyen, Y. Kawakami, S. Hazama, K. Okuno, S. Ogino, P. Gibbs, P. Waring, N. Sato, T. Torigoe, K. Itoh, P. S. Patel, S. N. Shukla, Y. Wang, S. Kopetz, F. A. Sinicrope, V. Scripcariu, P. A. Ascierto, F. M. Marincola, B. A. Fox and F. Pages (2014). "Towards the introduction of the 'Immunoscore' in the classification of malignant tumours." J Pathol 232(2): 199-209.

Gao Q, Qiu Sj Fau-Fan J, Fan J Fau-Zhou J, Zhou J Fau-Wang X-Y, Wang Xy Fau-Xiao Y-S, Xiao Ys Fau-Xu Y, et al. Intratumoral balance of regulatory and cytotoxic T cells is associated with prognosis of hepatocellular carcinoma after resection.

Gu-Trantien, C., S. Loi, S. Garaud, C. Equeter, M. Libin, A. de Wind, M. Ravoet, H. Le Buanec, C. Sibille, G. Manfouo-Foutsop, I. Veys, B. Haibe-Kains, S. K. Singhal, S. Michiels, F. Rothe, R. Salgado, H. Duvillier, M. Ignatiadis, C. Desmedt, D. Bron, D. Larsimont, M. Piccart, C. Sotiriou and K. Willard-Gallo (2013). "CD4(+) follicular helper T cell infiltration predicts breast cancer survival." J Clin Invest 123(7): 2873-2892.

Halliday G, Patel A, Hunt M, Tefany F, Barnetson R C. Spontaneous regression of human melanoma/nonmelanoma skin cancer: Association with infiltrating CD4+ T cells. World J Surg. 1995; 19:352-8.

Hastie R, Hastie, R. Tibshirani, J. Friedman, The Elements of Statistical Learning (Springer, New York, 2001).

Hegmans J P, Hemmes A, Hammad H, Boon L, Hoogsteden H C, Lambrecht B N. Mesothelioma environment comprises cytokines and T-regulatory cells that suppress immune responses. The European respiratory journal. 2006; 27:1086-95.

Hiraoka N, Onozato K Fau-Kosuge T, Kosuge T Fau-Hirohashi S, Hirohashi S. Prevalence of FOXP3+ regulatory T cells increases during the progression of pancreatic ductal adenocarcinoma and its premalignant lesions.

Huang C T, Oyang Y J, Huang H C, Juan H F. MicroRNA-mediated networks underlie immune response regulation in papillary thyroid carcinoma.

Issa-Nummer, Y., S. Darb-Esfahani, S. Loibl, G. Kunz, V. Nekljudova, I. Schrader, B. V. Sinn, H. U. Ulmer, R. Kronenwett, M. Just, T. Kuhn, K. Diebold, M. Untch, F. Holms, J. U. Blohmer, J. O. Habeck, M. Dietel, F. Overkamp, P. Krabisch, G. von Minckwitz and C. Denkert (2013). "Prospective validation of immunological infiltrate for prediction of response to neoadjuvant chemotherapy in HER2-negative breast cancer—a substudy of the neoadjuvant GeparQuinto trial." PLoS One 8(12): e79775.

Janowczyk A, S. C, Madabhushi A. Quantifying local heterogeneity via morphologic scale: Distinguishing tumoral from stromal regions. Journal of pathology informatics. 2013; 4(Suppl).

Kanehisa, M. and S. Goto (2000). "KEGG: kyoto encyclopedia of genes and genomes." Nucleic Acids Research 28(1): 27-30.

Kmiecik J, Poli A, Brons N H, Waha A, Eide G E, Enger P O, et al. Elevated CD3+ and CD8+ tumor-infiltrating immune cells correlate with prolonged survival in glioblastoma patients despite integrated immunosuppressive mechanisms in the tumor microenvironment and at the systemic level. Journal of neuroimmunology. 2013; 264: 71-83.

Kruger, J. M., C. Wemmert, L. Sternberger, C. Bonnas, G. Dietmann, P. Gancarski and F. Feuerhake (2013). "Combat or surveillance? Evaluation of the heterogeneous inflammatory breast cancer microenvironment." J Pathol 229(4): 569-578.

Kuong, K. J. and L. A. Loeb (2013). "APOBEC3B mutagenesis in cancer." Nat Genet 45(9): 964-965.

Monajemi, M., C. F. Woodworth, J. Benkaroun, M. Grant and M. Larijani (2012). "Emerging complexities of APOBEC3G action on immunity and viral fitness during HIV infection and treatment." Retrovirology 9: 35.

Kono K, Kawaida H, Takahashi A, Sugai H, Mimura K, Miyagawa N, et al. CD4(+)CD25high regulatory T cells increase with tumor stage in patients with gastric and esophageal cancers. Cancer Immunol Immunother. 2006; 55:1064-71.

Lee, H. J., J. Y. Seo, J. H. Ahn, S. H. Ahn and G. Gong (2013). "Tumor-associated lymphocytes predict response to neoadjuvant chemotherapy in breast cancer patients." J Breast Cancer 16(1): 32-39.

Liu, S., J. Lachapelle, S. Leung, D. Gao, W. D. Foulkes and T. O. Nielsen (2012). "CD8+ lymphocyte infiltration is an independent favorable prognostic indicator in basal-like breast cancer." Breast Cancer Res 14(2): R48.

Loi, S., N. Sirtaine, F. Piette, R. Salgado, G. Viale, F. Van Eenoo, G. Rouas, P. Francis, J. P. Crown, E. Hitre, E. de Azambuja, E. Quinaux, A. Di Leo, S. Michiels, M. J. Piccart and C. Sotiriou (2013). "Prognostic and predictive value of tumor-infiltrating lymphocytes in a phase III randomized adjuvant breast cancer trial in node-positive breast cancer comparing the addition of docetaxel to doxorubicin with doxorubicin-based chemotherapy: BIG 02-98." J Clin Oncol 31(7): 860-867.

McNamara M G, Lwin Z, Jiang H, Templeton A J, Zadeh G, Bernstein M, et al. Factors impacting survival following second surgery in patients with glioblastoma in the temozolomide treatment era, incorporating neutrophil/lymphocyte ratio and time to first progression. Journal of neuro-oncology. 2014; 117:147-52.

Ma, X., K. Norsworthy, N. Kundu, W. H. Rodgers, P. A. Gimotty, O. Goloubeva, M. Lipsky, Y. Li, D. Holt and A. Fulton (2009). "CXCR3 expression is associated with poor survival in breast cancer and promotes metastasis in a murine model." Mol Cancer Ther 8(3): 490-498.

Mahmoud, S. M. A., E. C. Paish, D. G. Powe, R. D. Macmillan, M. J. Grainge, A. H. S. Lee, I. O. Ellis and A. R. Green (2011). "Tumor-infiltrating CD8+ lymphocytes predict clinical outcome in breast cancer." J Clin Oncol 29(15): 1949-1955.

Mangeat, B., P. Turelli, G. Caron, M. Friedli, L. Perrin and D. Trono (2003). "Broad antiretroviral defence by human APOBEC3G through lethal editing of nascent reverse transcripts." Nature 424(6944): 99-103.

Mao, H., L. Zhang, Y. Yang, W. Zuo, Y. Bi, W. Gao, B. Deng, J. Sun, Q. Shao and X. Qu (2010). "New insights of CTLA-4 into its biological function in breast cancer." Curr Cancer Drug Targets 10(7): 728-736.

Milne K, Kobel M, Kalloger S E, Barnes R O, Gao D, Gilks C B, et al. Systematic analysis of immune infiltrates in high-grade serous ovarian cancer reveals CD20, FoxP3 and TIA-1 as positive prognostic factors. PloS one. 2009; 4:e6412.

Mittendorf et al (2014) "PD-L1 Expression in Triple Negative Breast Cancer" Cancer Immunol Res 2; 361.

Mukherji B Fau-Guha A, Guha A Fau-Loomis R, Loomis R Fau-Ergin M T, Ergin M T. Cell-mediated amplification and down regulation of cytotoxic immune response against autologous human cancer.

Natrajan, R., F. M. Mardakheh, H. Sailem, C. Bakal and Y. Yuan (In preparation). "The Ecosystem Diversity Landscape of Breast Cancer."

Ohno S, Ohno Y, Suzuki N, Kamei T, Koike K, Inagawa H, et al. Correlation of histological localization of tumor-associated macrophages with clinicopathological features in endometrial cancer. Anticancer research. 2004; 24:3335-42

Papewalis C, Kouatchoua C Fau-Ehlers M, Ehlers M Fau-Jacobs B, Jacobs B Fau-Porwol D, Porwol D Fau-Schinner S, Schinner S Fau-Willenberg H S, et al. Chromogranin A as potential target for immunotherapy of malignant pheochromocytoma.

Perou C, Sorlie T, Eisen M, van de Rijn M, Jeffrey S, Rees C, et al. Molecular portraits of human breast tumours. Nature. 2000; 406:747-52.

Prat, J., "Staging classification for cancer of the ovary, fallopian tube and peritoneum." International Journal of Gynecology and Obstetrics. 2013. (http://www.ncin.org.uk/view?rid=2515).

Pretscher D, Distel L V, Grabenbauer G G, Wittlinger M, Buettner M, Niedobitek G. Distribution of immune cells in head and neck cancer: CD8+ T-cells and CD20+B-cells in metastatic lymph nodes are associated with favourable outcome in patients with oro- and hypopharyngeal carcinoma. BMC cancer. 2009; 9:292.

Robert, C., L. Thomas, I. Bondarenko, S. O'Day, D. J. M, C. Garbe, C. Lebbe, J. F. Baurain, A. Testori, J. J. Grob, N. Davidson, J. Richards, M. Maio, A. Hauschild, W. H. Miller, Jr., P. Gascon, M. Lotem, K. Harmankaya, R. Ibrahim, S. Francis, T. T. Chen, R. Humphrey, A. Hoos and J. D. Wolchok (2011). "Ipilimumab plus dacarbazine for previously untreated metastatic melanoma." N Engl J Med 364(26): 2517-2526.

Rody, A., U. Holtrich, L. Pusztai, C. Liedtke, R. Gaetje, E. Ruckhaeberle, C. Solbach, L. Hanker, A. Ahr, D. Metzler, K. Engels, T. Karn and M. Kaufmann (2009). "T-cell metagene predicts a favorable prognosis in estrogen receptor-negative and HER2-positive breast cancers." Breast Cancer Res 11(2): R15.

Rody A, Karn T, Liedtke C, Pusztai L, Ruckhaeberle E, Hanker L, et al. A clinically relevant gene signature in triple negative and basal-like breast cancer. Breast cancer research: BCR. 2011; 13:R97

Salgardo, R. et al., (2014) "Harmonization of the evaluation of tumour infiltration lymphocytes (TILs) in breast cancer: recommendations by an international TILs-Working Group 2014. Annals of Oncology Salvi, S., V. Fontana, S. Boccardo, D. F. Merlo, E. Margallo, S. Laurent, A. Morabito, E. Rijavec, M. G. Dal Bello, M. Mora, G. B. Ratto, F. Grossi, M. Truini and M. P. Pistillo (2012). "Evaluation of CTLA-4 expression and relevance as a novel prognostic factor in patients with non-small cell lung cancer." Cancer Immunol Immunother 61(9): 1463-1472.

Schalper, K. A., V. Velcheti, D. Carvajal, H. Wimberly, J. Brown, L. Pusztai and D. L. Rimm (2014). "In Situ Tumor PD-L1 mRNA Expression Is Associated with Increased TILs and Better Outcome in Breast Carcinomas." Clin Cancer Res.

Spanos W C, Nowicki P, Lee D W, Hoover A, Hostager B, Gupta A, et al. Immune response during therapy with cisplatin or radiation for human papillomavirus-related head and neck cancer. Archives of otolaryngology—head & neck surgery. 2009; 135:1137-46.

Sjödahl G, Lovgren K, Lauss M, Chebil G, Patschan O, Gudjonsson S, et al. Infiltration of CD3+ and CD68+ cells in bladder cancer is subtype specific and affects the outcome of patients with muscle-invasive tumors. Urologic Oncology: Seminars and Original Investigations. 2014; 32:791-7.

Sorbye S W, Kilvaer T, Valkov A, Donnem T, Smeland E, Al-Shibli K, et al. Prognostic impact of lymphocytes in soft tissue sarcomas. PloS one. 2011; 6:e14611.

Stagg, J. and B. Allard (2013). "Immunotherapeutic approaches in triple-negative breast cancer: latest research and clinical prospects." Ther Adv Med Oncol 5(3): 169-181.

Subramanian, A., P. Tamayo, V. K. Mootha, S. Mukherjee, B. L. Ebert, M. A. Gillette, A. Paulovich, S. L. Pomeroy, T. R. Golub, E. S. Lander and J. P. Mesirov (2005). "Gene set enrichment analysis: a knowledge-based approach for interpreting genome-wide expression profiles." Proc Natl Acad Sci USA 102(43): 15545-15550.

Suzuki K, Kadota K, Sima C S, Nitadori J, Rusch V W, Travis W D, et al. Clinical impact of immune microenvironment in stage I lung adenocarcinoma: tumor interleukin-12 receptor beta2 (IL-12Rbeta2), IL-7R, and stromal FoxP3/CD3 ratio are independent predictors of recurrence. Journal of clinical oncology: official journal of the American Society of Clinical Oncology. 2013; 31:490-8.

The Cancer Genome Atlas Network (2012). "Comprehensive molecular portraits of human breast tumours." Nature 490(7418): 61-70.

Tjin E P, Krebbers G, Meijlink K J, van de Kasteele W, Rosenberg E H, Sanders J, et al. Immune-escape markers in relation to clinical outcome of advanced melanoma patients following immunotherapy. Cancer immunology research. 2014; 2:538-46.

Thompson R H, Dong H, Lohse C M, Leibovich B C, Blute M L, Cheville J C, et al. PD-1 is expressed by tumor-infiltrating immune cells and is associated with poor outcome for patients with renal cell carcinoma. Clinical cancer research: an official journal of the American Association for Cancer Research. 2007; 13:1757-61.

Townsend K N, Spowart J E, Huwait H, Eshragh S, West N R, Elrick M A, et al. Markers of T cell infiltration and function associate with favorable outcome in vascularized high-grade serous ovarian carcinoma. PloS one. 2013; 8:e82406.

Ueno T, Toi M, Saji H, Muta M, Bando H, Kuroi K, et al. Significance of macrophage chemoattractant protein-1 in macrophage recruitment, angiogenesis, and survival in human breast cancer. Clinical cancer research: an official journal of the American Association for Cancer Research. 2000; 6:3282-9.

Vauleon E, Tony A, Hamlat A, Etcheverry A, Chiforeanu D C, Menei P, et al. Immune genes are associated with human glioblastoma pathology and patient survival. BMC medical genomics. 2012; 5:41.

Villegas F R, Coca S, Villarrubia V G, Jimenez R, Chilion M J, Jareno J, et al. Prognostic significance of tumor infiltrating natural killer cells subset CD57 in patients with squamous cell lung cancer. Lung cancer (Amsterdam, Netherlands). 2002; 35:23-8.

Webster W S, Lohse C M, Thompson R H, Dong H, Frigola X, Dicks D L, et al. Mononuclear cell infiltration in clear-cell renal cell carcinoma independently predicts patient survival. Cancer. 2006; 107:46-53.

Welsh T J, Green R H, Richardson D, Waller D A, O'Byrne K J, Bradding P. Macrophage and mast-cell invasion of tumor cell islets confers a marked survival advantage in non-small-cell lung cancer. Journal of clinical oncology: official journal of the American Society of Clinical Oncology. 2005; 23:8959-67.

Witkin, A. P. "Scale-space filtering", Proc. 8th Int. Joint Conf. Art. Intell., Karlsruhe, Germany, 1019-1022, 1983.

Wu G, Han B I Fau-Pei X-t, Pei X T. Immune response of dendritic cells acquiring antigens from apoptotic cholangiocarcinoma cells induced by mitomycin.

Yang I, Tihan T, Han S J, Wrensch M R, Wiencke J, Sughrue M E, et al. CD8+ T-cell infiltrate in newly diagnosed glioblastoma is associated with long-term survival. Journal of clinical neuroscience: official journal of the Neurosurgical Society of Australasia. 2010; 17:1381-5.

Yong A S, Stephens N, Weber G, Li Y, Savani B N, Eniafe R, et al. Improved outcome following allogeneic stem cell transplantation in chronic myeloid leukemia is associated with higher expression of BMI-1 and immune responses to BMI-1 protein. Leukemia. 2011; 25:629-37.

Yuan, Y., H. Failmezger, 0. M. Rueda, H. R. Ali, S. Graf, S.-F. Chin, R. F. Schwarz, C. Curtis, M. J. Dunning, H. Bardwell, N. Johnson, S. Doyle, G. Turashvili, E. Provenzano, S. Aparicio, C. Caldas and F. Markowetz (2012). "Quantitative Image Analysis of Cellular Heterogeneity in Breast Tumors Complements Genomic Profiling." Science Translational Medicine 4(157): 157ra143.

Zhang Y, Wang L, Liu Y, Wang S, Shang P, Gao Y, et al. Preoperative neutrophil-lymphocyte ratio before platelet-lymphocyte ratio predicts clinical outcome in patients with cervical cancer treated with initial radical surgery. International journal of gynecological cancer: official journal of the International Gynecological Cancer Society. 2014; 24:1319-25.

The invention claimed is:
1. A computer-implemented method of measuring immune infiltration in a tumour, the method comprising:
providing an image of the tumour in which lymphocytes and cancer cells have been identified;

obtaining a lymphocyte-to-cancer measurement for each lymphocyte, comprising applying a density estimate to obtain a model of the cancer cell density; and determining the proximity of each lymphocyte to the cancer cell density;

classifying a subset of the lymphocytes as intra-tumour lymphocytes according to their lymphocyte-to-cancer measurement, wherein a lymphocyte is classified as an intra-tumour lymphocyte if it's lymphocyte-to-cancer measurement is above a threshold value;

quantifying the intra-tumour lymphocytes and the cancer cells in the tumour image;

calculating the intra-tumour lymphocyte ratio (ITLR) as the ratio of intra-tumour lymphocytes to cancer cells, wherein the ITLR is a measurement of immune infiltration in the tumour.

2. The method according to claim 1, further comprising a step of performing an automated image analysis on a first image of the tumor to provide the image of the tumour in which lymphocytes and cancer cells have been identified based on their nuclear morphologies.

3. The method according to claim 1 wherein the tumor is a tumor sample from a cancer patient having breast cancer, ovarian cancer, colorectal cancer, melanoma or non-small cell lung cancer.

4. The method of according to claim 3 wherein the cancer patient has breast cancer which is triple negative breast cancer.

5. A method of treating cancer in a cancer patient according to a therapeutic regime, the method comprising:
    measuring immune infiltration in a tumour, comprising:
        providing an image of the tumour in which lymphocytes and cancer cells have been identified;
        obtaining a lymphocyte-to-cancer measurement for each lymphocyte, comprising applying a density estimate to obtain a model of the cancer cell density; and determining the proximity of each lymphocyte to the cancer cell density;
        classifying a subset of the lymphocytes as intra-tumour lymphocytes according to their lymphocyte-to-cancer measurement, wherein a lymphocyte is classified as an intra-tumour lymphocyte if it's lymphocyte-to-cancer measurement is above a threshold value;
        quantifying the intra-tumour lymphocytes and the cancer cells in the tumour image;
        calculating the intra-tumour lymphocyte ratio (ITLR) as the ratio of intra-tumour lymphocytes to cancer cells, wherein the ITLR is a measurement of immune infiltration in the tumour; and
    treating the cancer patient according to the therapeutic regime depending on whether the ITLR is below or above a predetermined cut-off value.

6. The method of treating cancer according to claim 5, wherein the method further comprises surgically resecting a tumour from the cancer patient and measuring immune filtration in the surgically resected tumour.

7. The method of treating cancer according to claim 5, wherein the cancer patient has triple negative breast cancer, wherein the therapeutic regime comprises administration of a CTLA4 antagonist, and wherein the cancer patient is treated according to the therapeutic regime if the ITLR is above a predetermined cut-off value.

8. The method of treating cancer according to claim 5, wherein the image of a tumour is an image of a hematoxylin and eosin stained tumour section.

* * * * *

UNITED STATES PATENT AND TRADEMARK OFFICE
CERTIFICATE OF CORRECTION

PATENT NO. : 10,346,973 B2
APPLICATION NO. : 15/527284
DATED : July 9, 2019
INVENTOR(S) : Yinyin Yuan It is certified that error appears in the above-identified patent and that said Letters Patent is hereby corrected as shown below:

On the Title Page

Item (73) Please update the Assignee from "THE INSTITUTE OF CANCER RESEARCH: ROYAL CANCER HOS," with -- THE INSTITUTE OF CANCER RESEARCH: ROYAL CANCER HOSPITAL --.

Signed and Sealed this
Fifteenth Day of September, 2020

Andrei Iancu
*Director of the United States Patent and Trademark Office*